US011571473B2

(12) United States Patent
Narimatsu et al.

(10) Patent No.: US 11,571,473 B2
(45) Date of Patent: Feb. 7, 2023

(54) METHOD FOR EFFICIENTLY INDUCING ANTIBODY, ANTIBODY AND DETECTION SYSTEM FOR HEPATITIS VIRUS

(71) Applicants: NATIONAL INSTITUTE OF ADVANCED INDUSTRIAL SCIENCE AND TECHNOLOGY, Tokyo (JP); UNIVERSITY OF TOYAMA, Toyama (JP)

(72) Inventors: Hisashi Narimatsu, Tsukuba (JP); Kiyohiko Angata, Tsukuba (JP); Hiroyuki Kaji, Tsukuba (JP); Atsushi Kuno, Tsukuba (JP); Takashi Sato, Tsukuba (JP); Yasunori Chiba, Tsukuba (JP); Akira Togayachi, Tsukuba (JP); Hiroki Shimizu, Tsukuba (JP); Maki Sogabe, Tsukuba (JP); Takanori Wagatsuma, Tsukuba (JP); Masashi Mizokami, Ichikawa (JP); Masaaki Korenaga, Ichikawa (JP); Kazuto Tajiri, Toyama (JP); Tatsuhiko Ozawa, Toyama (JP)

(73) Assignees: NATIONAL INSTITUTE OF ADVANCED INDUSTRIAL, Tokyo (JP); SCIENCE AND TECHNOLOGY, Toyama (JP); UNIVERSITY OF TOYAMA, Toyama (JP)

( * ) Notice: Subject to any disclaimer, the term of this patent is extended or adjusted under 35 U.S.C. 154(b) by 0 days.

(21) Appl. No.: 16/972,367

(22) PCT Filed: Jun. 6, 2019

(86) PCT No.: PCT/JP2019/022588
§ 371 (c)(1),
(2) Date: Dec. 4, 2020

(87) PCT Pub. No.: WO2019/235584
PCT Pub. Date: Dec. 12, 2019

(65) Prior Publication Data
US 2021/0283246 A1    Sep. 16, 2021

(30) Foreign Application Priority Data
Jun. 6, 2018   (JP) ............................. JP2018-108179

(51) Int. Cl.
| A61K 39/29 | (2006.01) |
| C07K 14/005 | (2006.01) |
| A61P 31/20 | (2006.01) |
| C07K 16/08 | (2006.01) |
| G01N 33/576 | (2006.01) |
| A61K 39/00 | (2006.01) |

(52) U.S. Cl.
CPC ............ *A61K 39/292* (2013.01); *A61P 31/20* (2018.01); *C07K 14/005* (2013.01); *C07K 16/082* (2013.01); *G01N 33/5761* (2013.01); *A61K 2039/505* (2013.01); *C07K 2317/56* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS 10,175,257 B2 *    1/2019   Hryhorenko ........... G01N 33/94

FOREIGN PATENT DOCUMENTS

WO    2016/167369 A1    10/2016

OTHER PUBLICATIONS

Sugiyama et al. (Large HBV S protein BAF36035, 2006).*
Feb. 16, 2022 Extended European Search Report issued in European Patent Application No. 19814552.6.
Schmitt et al; "Structure of pre-S2 N- and O-linked glycans in surface proteins from different genotypes of hepatitis B virus," Journal of General Virology; pp. 2045-2053; 2004.
Hyakumura et al; "Modification of Asparagine-Linked Glycan Density for the Design of Hepatitis B Virus Virus-Like Particles with Enhanced Immunogenicity;" Journal of Virology; vol. 89; No. 22; pp. 11312-11322; Nov. 2015.
Singh et al; "A Recombinant Measles Virus Expressing Hepatitis B Virus Surface Antigen Induces Humoral Immune Responses in Genetically Modified Mice;" Journal of Virology; vol. 73; No. 6; pp. 4823-4828; Jun. 1999.
Angata et al; "O-glycosylated HBsAg peptide can induce specific antibody neutralizing HBV infection;" Biochimica ET Biophysica ACTA; pp. 1-12; Sep. 25, 2021.
Ito et al.; "Impairment of Hepatitis B Virus Virion Secretion by Single-Amino-Acid Substitutions in the Small Envelope Protein and Rescue by a Novel Glycosylation Site;" Journal of Virology; 2010; pp. 12850-12861; vol. 84, No. 24.
Nishiguchi; "Comparison of each HBs antigen assay and it's clinical utility;" Kanzo; 2014; pp. 310-324; vol. 55, No. 6.
Sobotta et al.; Mapping of immunodominant B-cell epitopes and the human serum albumin-binding site in natural hepatitis B virus surface antigen of defined genosubtype; Journal of General Virology; 2000; pp. 369-378; vol. 81.

(Continued)

*Primary Examiner* — Agnieszka Boesen
(74) *Attorney, Agent, or Firm* — Oliff PLC

(57) ABSTRACT

An examination system that recognizes a glycosylated antigen in Dane particles of hepatitis B virus (HBV) and a neutralizing antibody that recognizes the glycosylated antigen and that exhibits an infection-inhibiting activity. It was elucidated that Dane particles are associated with specific glycan structures, and this enabled the construction of a new detection system for infectious, i.e., nucleic acid-containing, hepatitis B virus particles and the provision of a neutralizing antibody that recognizes a glycosylated antigen and that exhibits an infection-inhibiting activity.

9 Claims, 32 Drawing Sheets

Specification includes a Sequence Listing.

(56) References Cited

OTHER PUBLICATIONS

Glebe et al.; "Pre-S1 Antigen-Dependent Infection of Tupaia Hepatocyte Cultures with Human Hepatitis B Virus;" Journal of Virology; 2003; pp. 9511-9521; vol. 77, No. 17.
Schmitt et al.; "Analysis of the Pre-S2 N- and 0-linked Glycans of the M Surface Protein from Human Hepatitis B Virus;" Journal of Biological Chemistry; 1999; pp. 11945-11957; vol. 274, No. 17.
Liu et al.; "N-linked Glycosylation at an Appropriate Position in the Pre-S2 Domain is Critical for Cellular and Humoral Immunity against Middle HBV Surface Antigen;" Tohoku J. Exp. Med; 2015; pp. 131-138; vol. 236, No. 2.
Liu et al.; "The N-Glycosylation Modification of LHBs (Large Surface Proteins of HBV) Effects on Endoplasmic Reticulum Stress, Cell Proliferation and its Secretion;" Hepatitis Monthly; 2013; pp. 1-9; vol. 13, No. 9, e12280.
Machida et al.; "A Glycopeptide Containing 15 Amino Acid Residues Derived from Hepatitis B Surface Antigen particles: Demonstration of Immunogenicity to Raise Anti-HBs in Mice;" Molecular Immunology; 1982; pp. 1087-1093 vol. 19, No. 9.
Wagatsuma et al.; Highly Sensitive Glycan Profiling of Hepatitis B Viral Particles and a Simple Method for Dane Particle Enrichment; Analytical Chemistry; 2018; pp. 10196-10203; vol. 90.
Aug. 27, 2019 Search Report issued in International Patent Application No. PCT/JP2019/022588.
Dec. 8, 2020 International Preliminary Report on Patentability issued in International Patent Application No. PCT/JP2019/022588.

\* cited by examiner

FIG.3
A
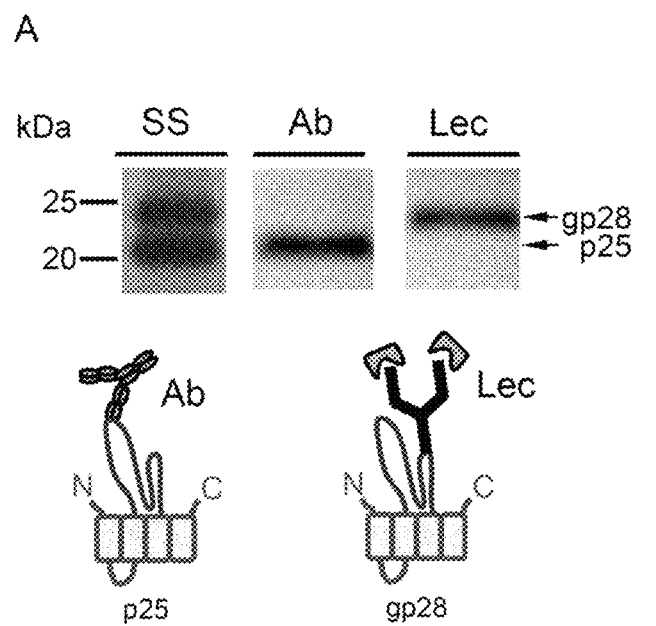
B
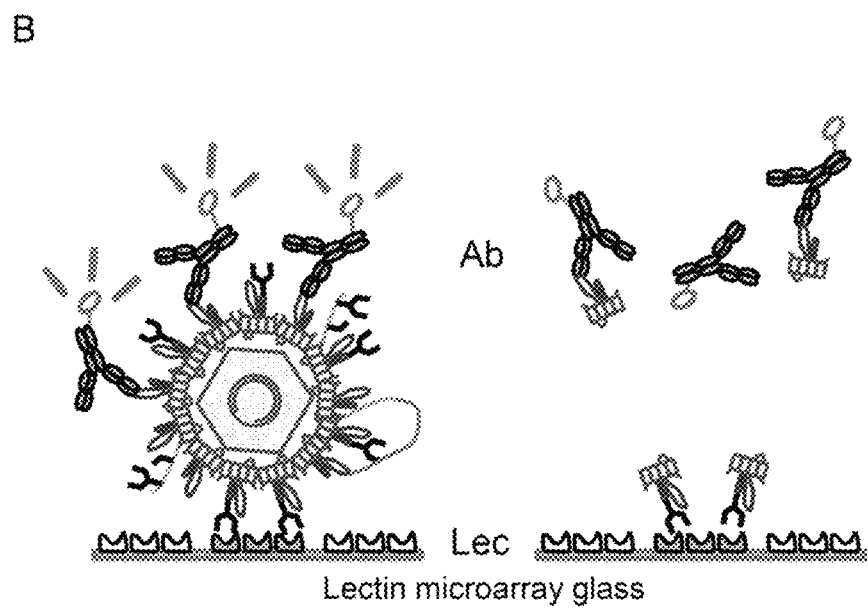
Lectin microarray glass

FIG.3 (continued)
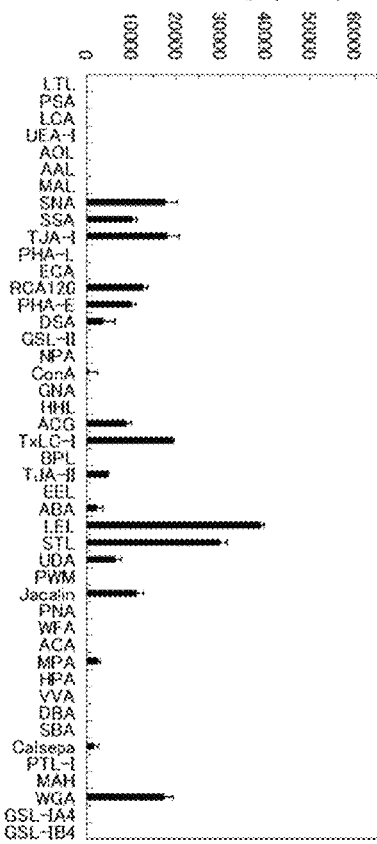
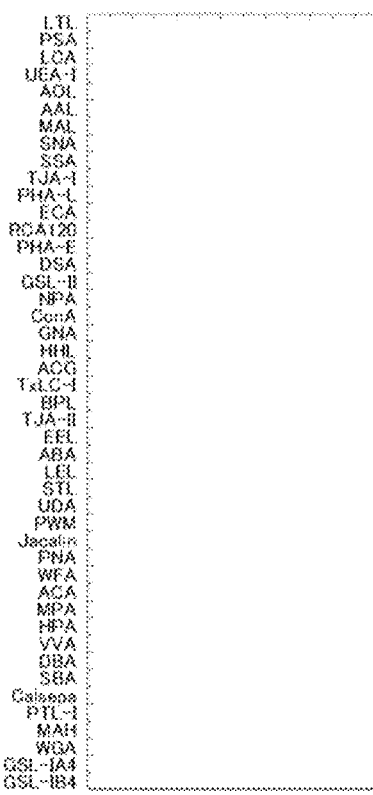

A

B

| Lectins | | SSA | ECA | Jacalin | PNA | PHA-E | WGA | WFA |
|---|---|---|---|---|---|---|---|---|
| DTT+ | Intact | + | - | + | - | - | - | - |
| | asialo | - | + | ++ | + | - | - | + |
| DTT- | Intact | ++ | - | ++ | - | - | + | - |
| | asialo | - | + | ++ | ++ | + | + | ++ |
| Specificity | | gp28 gp33 gp36 | gp28 gp33 gp36 | gp33 gp36 | gp33 gp36 | | | gp28 |

FIG.5
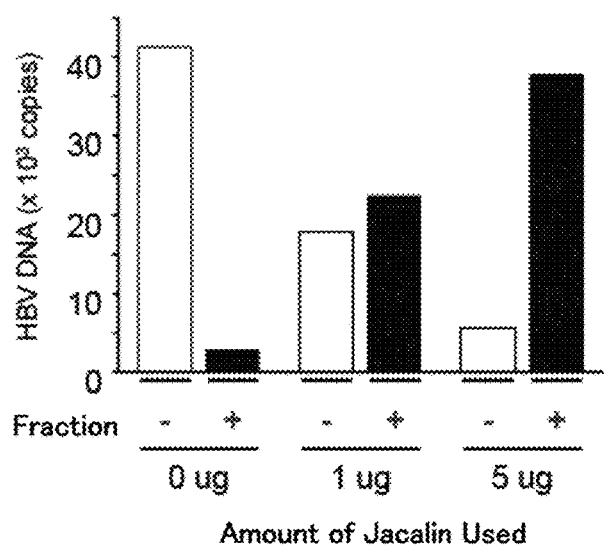
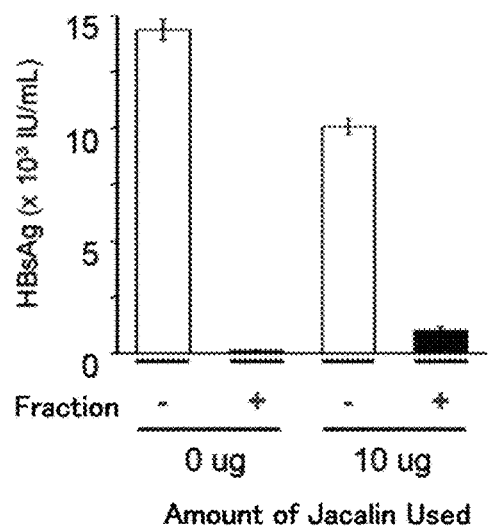

*O*-Glycosylation Site gi|77680739 138-167

GLYFPAGGSSSGTVNPVPTTASPISSIFSR (SEQ ID NO: 41)

FIG.8 gi|77680739 (SEQ ID NO: 13)

```
  1 MGGWSSKPRQ GMGTNLSVPN PLGFFPDHQL DPAFGANSNN PDWDFNPNKD
 51 HWPEANQVGA GAFGPGFTPP HGGLLGWSPQ AQGILTTLPA APPPASTNRQ
101 SGRQPTPISP PLRDSHPQAM QWNSTTFHQA LLDPRVRGLY FPAGGSSSGT
151 VNPVPTTASP ISSIFSRTGD PAPNMESTTS GFLGPLLVLQ AGFFLLTRIL
201 TIPQSLDSWW TSLNFLGGAP TCPGQNSQSP TSNHSPTSCP PTCPGYRWMC
251 LRRFIIFLFI LLLCLIFLLV LLDYQGMLPV CPLLPGTSTT STGPCRTCTI
301 PAQGTSMFPS CCCTKPSDGN CTCIPIPSSW AFARFLWEWA SVRFSWLSLL
351 VPFVQWFVGL SPTVWLSAIW MMWYWGPSLY NILSPFLPLL PIFFCLWVYI
``` gi|172045927

MGGWSSKPRKGMGTNLSVPNPLGFFPDHQLDPAFGANSENPDWDLNPHKDNWPDAHKVGVGAFGPGFTPPHGGLLGWSPQAAGGILTSVPAAPPP 400
ASTNRGSGRQPTPLSPPLRDTHPQAMQWNSTTFHQTLQDPRVRALYLPAGGSSSGTVSAISSILSTTGDPVPNMEMASGLLGPLLVLQ
AGFFSLTKILTTPQSLDSWWTSLFLGGTPVGLGQNSQSPICCGPPIGPGYRWMYLRRFIIXLCILLLGLIFLLVLLDYQGMLPVCPLIPGSSTTS
TGPCKTCTTPAQGTSMFPSGCCTKPTDGNCTCPIPSSWAFAKYLWEWASVRFSWLSLLVPFVQWFVGLSPTVWLSVWMMWYWGPSLYNILSPFM
PLLPIFFCLWVYI (SEQ ID NO: 42)

gi|138797

MGGWSSKPRQGMGTNLSVPNPLGFFPDHQLDPAFGANSNNPDWDFNPNKDGWPEANQVGAGAFGPGFTPPHGGLLGWSPQAAGGILTVVPAAPP 400
PASTNRQSGRQPTPISPPLRDSHPQAMQWNSTTFHQALLDPRVRGLYFPAGGSSSGTVNPVPTTASPISSIFSRTGDPAPNMENTTSGFLGPLLVLQ
AGFFLLTRILTIPQSLDSWWTSLNFLGGAPTCPGQNSQSPTSNHSPTSCPPICPGYRWMCLRRFIFIFLFILLCLIFLLVLLDYQGMLPVCPLLPGTSTT
STGPCKTCTIPAQGGTSMFPSCCCTKPSDGNCTCIPIPSSWAFARFLWEWASVRFSWLSLLVPFVQWFVGLSPTVWLSVWMMWYWGPSLYNILSPFLP
PLLPIFFCLWVYI (SEQ ID NO: 43)

gi|77660740

MGGWNSTTFHQALLDPRVRGLYFPAGGSSSGTVNPVPTTASPISSIFSRTGDPAPNMESTTSGFLGPLLVLQAGFFLLTRILTIPQSLDSWWTSLNFLG 281
GAPTCPGQNSQSPTSNH-SPTSCPPTCPGYRWMCLRRFIFIFLFILLCLIFLLVLLDYQGMLPVCPLLPGTSTTSTGPCRTCTIPAQGTSMFPSCCCTK
PSDGNCTCIPIPSSWAFARFLWEWASVRFSWLSLLVPFVQWFVGLSPTVWLSAIWMMWYWGPSLYNILSPFLPLLPIFFCLWVYI (SEQ ID NO: 44)

gi|82035778

MGGYSSKPRKGMGTNLSVPNPLGFLPDHQLPAFGANSNNPDWDFNPNKDPWPEAWQVGAGAFGPGFTPPHGSLLGWSPQAAGGILTVVPATPPP 400
ASTNRQSGRQPTPISPPLRDSHPQAMQWNSTTFHQAALLDPRVRGLYFPAGGSSSGTANPVPTTASPISSIFSRTGDPVPKMENTTSGFLGPLLVLQA
GFFLLTRILTIPQSLDSWWTSLNFLGGAPACPGCGNSQSPTSNHSPTSCPPIGPGYRWMCLRRFIFIFLFRILLCLIFLLVLLDYQGMLPVCPLIPGTSTTST
GPCKTCTTPAQGTSMFPSCCCTKPSDGNCTCIPIPSSWAFAKFLWEWASVRFSWLSLLAPFVQWFVGLSPTVWLSVWMMWYWGPSLYNILSPFLPL
LPIFFCLWVYI (SEQ ID NO: 45)

gi|82032961

MGGWSSKPRQGMGTNLSVPNPLGFFPDHHLDPAFGANSNNPDWDFFNPNKDHWPKANQVRAGAFGPGFTPPHQSLLGWSPQAAGGILTVVPAAPPP 400
ASSNROSGKQPTPISPPLRDSHPQAMQWNSTTFHQALLDPRVRGLYFPAGGSSSGTVNPVPTTASPISSIFSRTGIDPALNMENITSGFLGPLLVLQA
GFFLLTRILTIPQSLDSWWTSLNFLGGTTVGLGQNSQSPISNHSPTSCPPTCPGYRWMCLRRFIFIFLFILLGLIFLLVLLDYQGMLPVCPLIPGSSTTST
GPCRTCTTPAQGTSMYPSCCCTKPSDGNCTCIPIPSSWAFGKFLWEWASARFSWLSLLVPFVQWFVGLSPTVWLSVWMMWYWGPSLYSILSPFLP
LLPIFFCLWVYI (SEQ ID NO: 46)

FIG.9

| HBs | Preparation Method | Structure |
|---|---|---|
| S (-Gly) | Yeast | 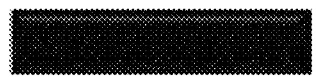 |
| M (+Gly) [Glyco-M] | HuH7 | 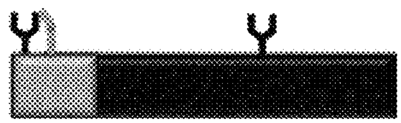 |
| L (+Gly) [Glyco-L] | Yeast | 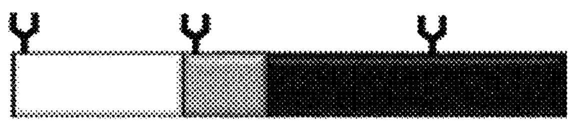 |
| PreS2 | Synthesis |  |
| PreS2+O [Glyco-PreS2] | Synthesis + Enzymatic Method | 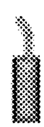 |

FIG.10
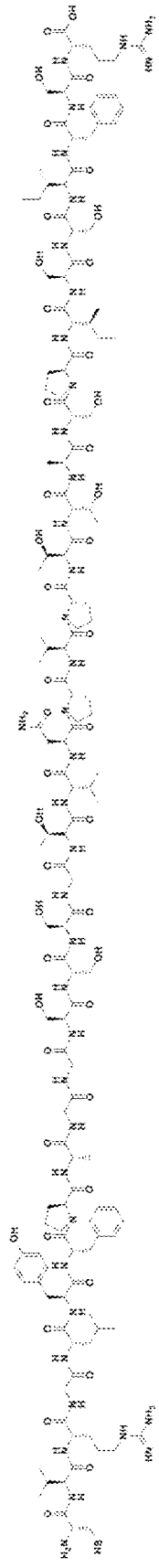
PreS2: PreS2 (Cys+V17-R48)
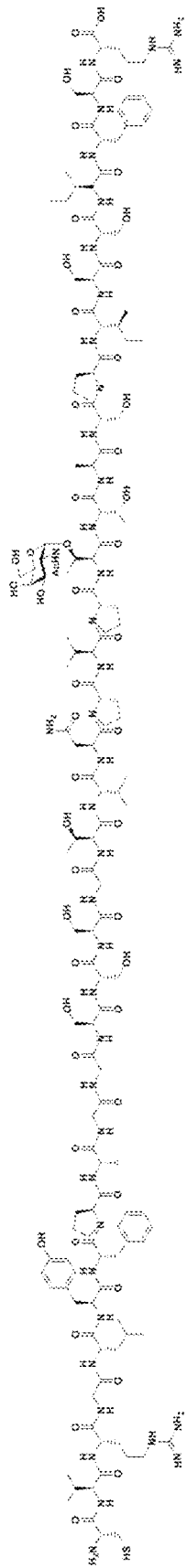
PreS2+O: PreS2 (Cys+V17-R48, T37+GalNAc)

Glyco-L Expression Vector (YEpHBVC2)

FIG.13

Culturing Method

Medium:
0.67% yeast nitrogen base
1% casamino acid
2% glucose

Host:
*S. cerevisiae* W303-1B (*MATα ura3-52 trp1Δ2 leu2-3_112 his3-11 ade2-1 can1-100*) / YEpHBVC2

120 rpm, 30°C, 120 h Culture → Collect bacteria

Purification Method

Lyse bacteria in Y-PER, dialyzable + 7.5 M Urea
↓
12000 rpm, 4°C, 30min Centrifugation
↓
Dissolve PEG precipitation product in a buffer containing 15 mM EDTA, 7.5 M Urea
↓
Density gradient centrifugation (73,000 × g, 4°C, 16h) with 10-40% KBr
↓
Density gradient centrifugation (73,000 × g, 4°C, 16h) with 5-50% sucrose
↓
Dialyze and lyophilize HBs fractions
↓
70°C, 20 min treatment, 0.45 μm UF membrane treatment
↓
Lyophilization FIG.15
A) Changes in Anti-L-HBs Antibody Titers (Temporal Changes in Antibody Levels in Blood): Day 0-Day 35
L-HBs coated ELISA
Antisera from mice immunized with antigen AIST L-HBs (YL), bimmugen (B), or none (N)
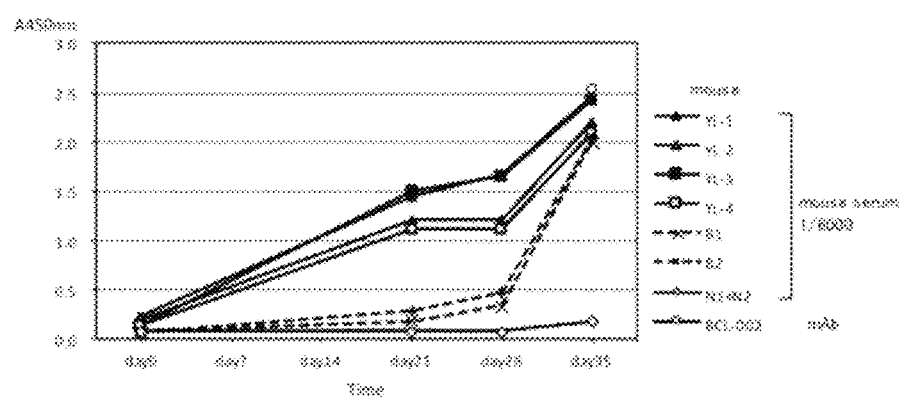
B) Changes in Anti-L-HBs Antibody Titers: Day 35
L-HBs coated ELISA
Antisera from mice immunized with antigen AIST L-HBs (YL), bimmugen (B), or none (N), serially diluted
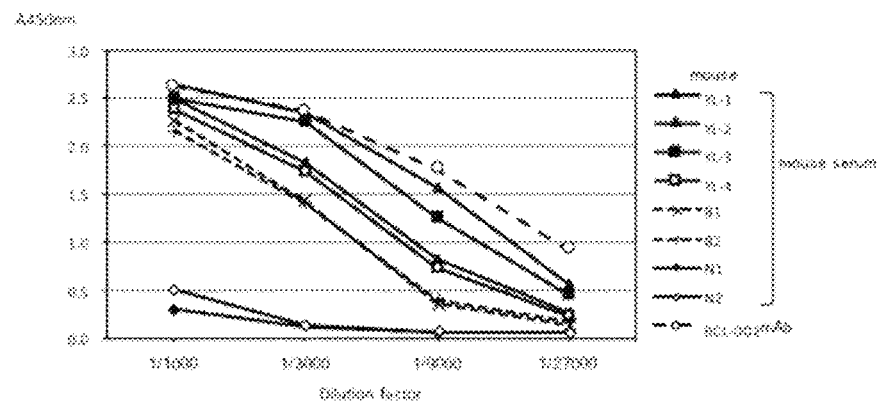

FIG.18
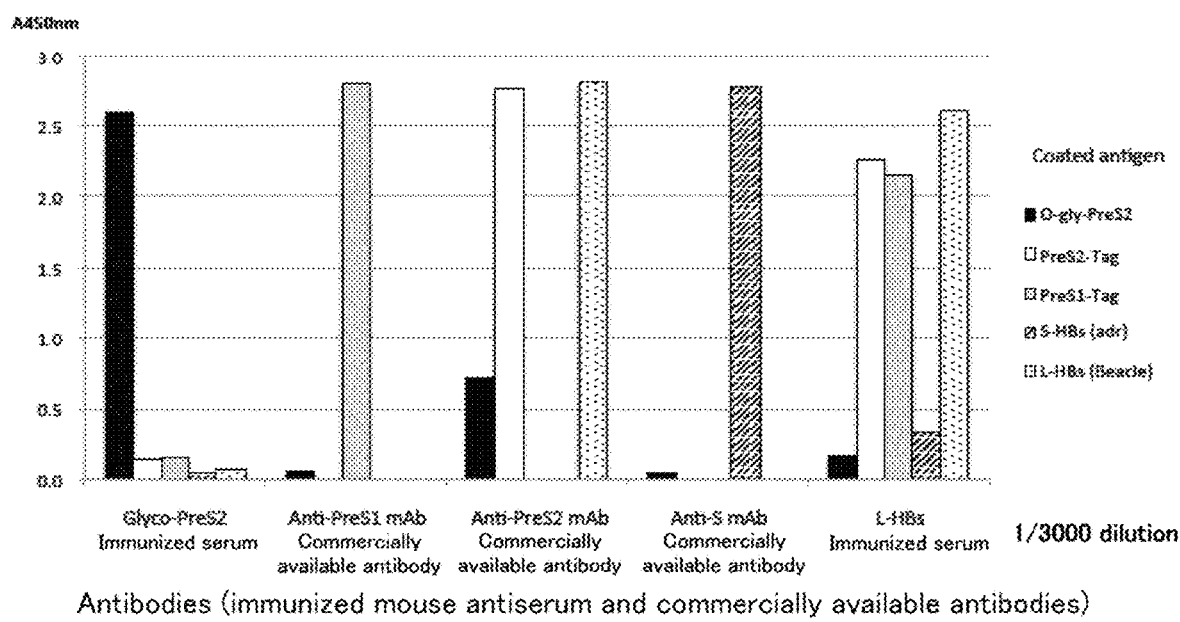
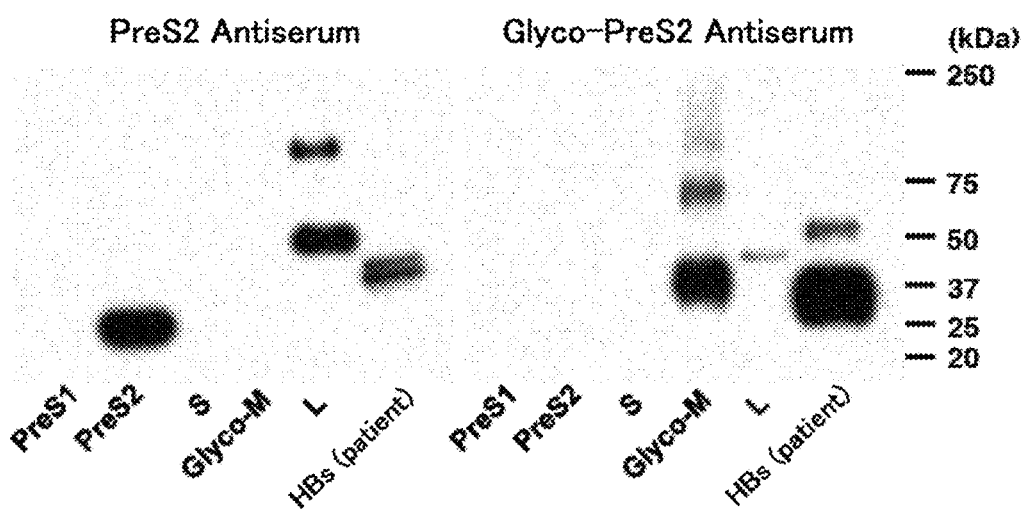

ELISA with Antisera of Mice Immunized with *O*-Glycosylated PreS2

FIG.20A

Anti-PreS1 Ig: Heavy chain amino acid sequences

PreS1-Ig heavy chain alignment

FIG.20B

Anti-PreS1 Ig: Light chain amino acid sequences

FIG.21A

Anti-Glyco-PreS2 Ig: Heavy chain amino acid sequences

```
              10        20        30        40        50        60        70        80        90
         ATGGGATGGAGATGGATCCTTCTTTTCCTCCTGTCAGGAACTGCAGGTGTCCACTGCCAGGTTCAGCTGCAGCAGTCCGGACCTGAGCTG
FS#4     M  G  W  R  W  I  L  L  F  L  L  S  G  T  A  G  V  H  C  Q  V  Q  L  Q  Q  S  G  P  E  L
F3 RNA   M  G  W  S  W  V  L  P  L  L  S  V  T  A  G  V  H  S  Q  V  Q  L  Q  Q  S  G  A  E  L
F3 RNA2  M  G  W  R  W  I  L  L  F  L  L  S  G  T  A  G  V  H  S  Q  V  Q  L  Q  Q  S  G  P  E  L 100       110       120       130       140       150       160       170       180
         GTGAAGCCTGGGGCTTTAGTGAAGATATCGTGCAAGGCTTCTGGTTACACCTTCACAAGCTACGATATAAACTGGGTGAAGCAGAGGCCT
FS#4     V  K  P  G  A  L  V  K  I  S  C  K  A  S  G  Y  T  F  T  S  Y  D  I  N  W  V  K  Q  R  P
F3 RNA   M  K  P  G  A  S  V  K  I  S  C  K  A  S  G  Y  T  F  T  S  Y  N  M  D  W  V  K  Q  R  P
F3 RNA2  V  K  P  G  A  S  V  K  M  S  C  K  A  S  G  Y  T  F  T  Y  Y  D  I  N  W  V  K  Q  R  P 190       200       210       220       230       240       250       260       270
         GGACAGGGACTTGAGTGGATTGGATGGATTTATCCTGGAGATGGTCGTACTAAGTACAATGAGAAATTCAAGGGCAAGGCCACACTGACT
FS#4     G  Q  G  L  E  W  I  G  W  I  Y  P  G  D  G  R  T  K  Y  N  E  K  F  K  G  K  A  T  L  T
F3 RNA   G  Q  G  L  E  W  I  G  W  I  Y  P  G  D  G  D  T  R  Y  N  Q  K  F  K  G  K  A  T  L  T
F3 RNA2  G  Q  G  L  E  W  I  G  W  I  Y  P  G  D  G  S  T  K  L  N  E  S  F  K  G  K  A  S  L  T 280       290       300       310       320       330       340       350       360
         GCAGACAAATCCTCCAGCACAGCCTATATGCAGCTCAGCAGCCTGACTTCTGAGAACTCTGCAGTCTATTTTTGTGTAAGATCACACGAT
FS#4     A  D  K  S  S  S  T  A  Y  M  Q  L  S  S  L  T  S  E  N  S  A  V  Y  F  C  V  R  S  H  D
F3 RNA   A  D  K  S  S  S  T  A  Y  M  Q  L  S  S  L  T  S  E  D  S  A  V  Y  Y  R  A  R        (SEQ ID NO: 89)
F3 RNA2  A  D  K  S  S  S  T  A  Y  L  H  L  S  S  L  P  S  E  N  S  A  V  Y  F  C  A  R        (SEQ ID NO: 90)

370       380       390       400       410       420       430       440       450
         AGTAATTACGGGGCCTGGTTTCCTTACTGGGGCCAAGGGACTCTGGTCACTGTCTCTGCAGCCAAAACGACACCCCCATCTGTCTATCCA
FS#4     S  N  Y  G  A  W  F  P  Y  W  G  Q  G  T  L  V  T  V  S  A  A  K  T  T  P  P  S  V  Y  P 460       470       480       490       500       510       520       530       540
         CTGGCCCCTGGATCTGCTGCCCAAACTAACTCCATGGTGACCCTGGGATGCCTGGTCAAGGGCTATTTCCCTGAGCCAGTGACAGTGACC
FS#4     L  A  P  G  S  A  A  Q  T  N  S  M  V  T  L  G  C  L  V  K  G  Y  F  P  E  P  V  T  V  T

550
         TGGAACTCTGGA (SEQ ID NO: 1)
FS#4     W  N  S  G  (SEQ ID NO: 3)
```

FIG.21B

Anti-Glyco-PreS2 Ig: Kappa chain amino acid sequences

```
          10        20        30        40        50        60        70        80        90
ATGAAGTTGCCTGTTAGGCTGTTGGTGCTGATGTTCTGGATTCCTGCTTCCAGAAGTGATGTATTGATGACCCAAACTCCACTCTCCCTG
 M  K  L  P  V  R  L  L  V  L  M  F  W  I  P  A  S  R  S  D  V  L  M  T  Q  T  P  L  S  L 100       110       120       130       140       150       160       170       180
CCTGTCAGTCTTGGAAATCAAGCCTCCATCTCTTGCAGATCTAGTCAGAACATTGTACATAGTAATGGAAACACCTATTTAGAATGGTAC
 P  V  S  L  G  N  Q  A  S  I  S  C  R  S  S  Q  N  I  V  H  S  N  G  N  T  Y  L  E  W  Y 190       200       210       220       230       240       250       260       270
CTGCAGAAACCAGGCCAGTCTCCAAAGCTCCTGATCTACAAAGTTTCTAACCGATTTTCTGGGGTCCCCGACAGGTTCAGTGGCAGTGGA
 L  Q  K  P  G  Q  S  P  K  L  L  I  Y  K  V  S  N  R  F  S  G  V  P  D  R  F  S  G  S  G 280       290       300       310       320       330       340       350       360
TCAGGGACAGATTTCACACTCAAGATCAGCAGAGTGGAGGCTGAGGATCTGGGAGTTTATTACTGCTTTCAAGGTTCACATGTTCCGCTC
 S  G  T  D  F  T  L  K  I  S  R  V  E  A  E  D  L  G  V  Y  Y  C  F  Q  G  S  H  V  P  L 370       380       390       400       410       420       430       440       450
ACGTTCGGTACTGGGACCAAGCTGGAGCTGAAACGGGCTGATGCTGCACCAACTGTATCCATCTTCCCACCATCCAGTGAGCAGTTAACA
 T  F  G  T  G  T  K  L  E  L  K  R  A  D  A  A  P  T  V  S  I  F  P  P  S  S  E  Q  L  T 460       470       480       490       500       510       520       530       540
TCTGGAGGTGCCTCAGTCGTGTGCTTCTTGAACAACTTCTACCCCAAAGACATCAATGTCAAGTGGAAGATTGATGGCAGTGAACGACAA
 S  G  G  A  S  V  V  C  F  L  N  N  F  Y  P  K  D  I  N  V  K  W  K  I  D  G  S  E  R  Q 550       560
AATGGCGTCCTGAACAGTTG  (SEQ ID NO: 2)
 N  G  V  L  N  S     (SEQ ID NO: 4)
```

METHOD FOR EFFICIENTLY INDUCING ANTIBODY, ANTIBODY AND DETECTION SYSTEM FOR HEPATITIS VIRUS

The present application contains a Sequence Listing that has been submitted electronically in ASCII format and is hereby incorporated by reference in its entirety. The ASCII copy, created on May 25, 2021, is named Substitute Sequence Listing_ST25.txt and is 66,527 bytes in size.

TECHNICAL FIELD

The present invention relates to a hepatitis B virus antigen and a manufacturing method thereof, a composition for a vaccine, containing a hepatitis B virus antigen, an anti-hepatitis B virus antibody and a nucleic acid encoding the antibody, a hepatitis B virus detection system, and a pharmaceutical composition for hepatitis B virus.

BACKGROUND

Hepatitis B virus (HBV) is a virus that belongs to the Hepadnaviridae family, has DNA that is not fully double-stranded, and specifically infects the human liver. HBV infection can lead to the development of acute hepatitis B, chronic hepatitis, cirrhosis, and hepatocellular carcinoma, which are serious health problems. It is believed that approximately 1% (approximately 1.1 to 1.4 million people) of the population in Japan are hepatitis B virus (HBV) carriers, and approximately 5% (350 million people) of the population worldwide are infected (as reported by the WHO).

Interferon (antiviral drug) immunotherapy and nucleic acid analogues (reverse transcriptase inhibitors) are used for the treatment of hepatitis B, but issues such as side effects and the occurrence of resistant viruses have been indicated, and new drugs with new targets are expected.

Meanwhile, vaccination is effective to prevent the spread of HBV infection. Although universal vaccination against HBV is currently being implemented in various countries and regions around the world, it is considered difficult to prevent the occurrence of new HBV infections, in part because universal vaccination was not performed in Japan until recently. Currently, vaccines (recombinant S-HBs antigen (S-HBsAg)) made in yeast are used, but all are used as proteins without glycosylation.

To induce an increase in antibody titers after vaccination, a plurality of doses (three doses) is required, and antibody acquisition is observed in nearly 90% of vaccinees with the current vaccines. However, the acquired antibody titers differ greatly between individuals. These issues of antibody induction efficiency also need to be improved to curb the costs of universal vaccination. Meanwhile, cases have been recently reported in which the HBV vaccine is not able to prevent HBV infection even though the vaccine can prevent the onset of hepatitis B. In addition, escape mutants and occult infections, which are not recognized by antibodies induced by HBV vaccination, are reported, and it is important to develop next-generation HBV vaccines (e.g., vaccines that are effective even with a low number of doses and have broader antiviral effects) and anti-HBV antibodies that can also accommodate these mutant HBVs.

Infectious HBV particles (Dane particles) and non-infectious subviral particles (SVPs) are present in the blood of HBV-infected individuals. The infectious Dane particles have a structure containing DNA in a core (containing HBcAg proteins) that is further enveloped (by HBsAg proteins), whereas the non-infectious subviral particles (SVPs) contain only HBsAg and no DNA (FIG. 1).

The HBs genes are composed of PreS1, PreS2, and S, and encode three membrane proteins (L-HBsAg, M-HBsAg, and S-HBsAg) starting from distinct translation-initiating methionine codons. Differences in the composition of these different HBsAgs-form the HBV particles (Dane particles and SVPs) described above. Conventional vaccines have glycan-free S-HBsAgs (S (−Gly)) expressed in yeast as the antigens and do not contain the glycan-bearing L, M, S (+Gly) glycoproteins contained in the actual HBV-particles. It has been suggested that SVP is present in patients' sera a thousand times or more than Dane particles, and it is assumed that the HBV recognized by the current HBV vaccination is predominantly the non-infectious SVP.

Although the proportion of the infectious Dane particles is only about 1/1000 of the non-infectious SVP, HBV is a highly contagious virus. To accurately measure the HBV particles (Dane particles) or to raise the HBV detection limits, one approach is to concentrate the infectious Dane particles. Moreover, in order to generate vaccines that efficiently induce antibodies, it is critical to select targets (antigens) that can distinguish between Dane particles and the non-infectious small particles (SVPs).

In addition, although the safety of blood donations is ensured by screening with nucleic acid tests (NAT), HBV infection is established at a low copy at or below the detection limit, so infectious accidents caused by blood transfusions still take place compared with HCV and HIV. That is, techniques to concentrate Dane particles are essential to increase the accuracy of HBV detection.

CITATION LIST

Patent Literature

Patent Document 1: WO 2016/167369 A

Non-Patent Literature

Non-Patent Document 1: Ito K et al. J Virol. 2010 December; 84(24):12850-61.

SUMMARY OF INVENTION

Technical Problem

It is an object of the present invention to provide techniques and products for acquiring examination systems that can recognize Dane particles without recognizing the subviral particles of hepatitis B virus (HBV), hepatitis B virus antigens that can be used as vaccines capable of inducing the production of antibodies capable of recognizing Dane particles without recognizing the subviral particles, or neutralizing antibodies that recognize Dane particles without recognizing the subviral particles and that exhibit infection-inhibiting effects, so as to provide a broad coverage of the above cases that currently need to be addressed.

Solution to Problem

The present inventors elucidated that Dane particles are associated with specific glycan structures. This led to the successful construction of a new detection system for infectious, i.e., nucleic acid-containing, hepatitis B virus particles.

In other words, the present invention relates to the following (1)-(21) and [1]-[21].

(1) A method for antibody induction and screening using an antibody and a lectin, for distinguishing between an infectious HBV particle (Dane particle) and a non-infectious subviral particle (SVP) in hepatitis B virus.

(2) A glycan-bearing hepatitis B virus antigen, for the above method for antibody induction and screening using an antibody and lectin.

(3) A glycan-bearing hepatitis B virus antigen in HBs glycoprotein encoded by a gene selected from the group consisting of PreS1, PreS2, and S regions, for the above method.

(4) A hepatitis B virus antigen from HBs glycoprotein, having a structure of formula [1], [2], or [3] below.

[Chem. 1]
(SEQ ID NO: 15)

$$\text{NeuAc}\alpha2\text{---}3\text{Gal}\beta1\text{----}3\text{GalNAc} \qquad [1]$$
$$|$$
$$\text{VRGLYLPAGGSSSGTVNPVPTTASPISSIFSR}$$

[Chem. 2]
(SEQ ID NO: 16)

$$\text{NeuAc}\alpha2\text{---}3\text{Gal}\beta1\text{----}3\text{GalNAc} \qquad [2]$$
$$|$$
$$\text{SSSGTVNPVPTTASPISSIFS}$$

[Chem. 3]
(SEQ ID NO: 17)

$$\text{NeuAc}\alpha2\text{---}3\text{Gal}\beta1\text{----}3\text{GalNAc} \qquad [3]$$
$$|$$
$$\text{TVNPVPTTASPIS}$$

(5) A hepatitis B virus antigen, having an amino acid sequence homology of at least 70% to formula [1], [2], or [3] above.

(6) A hepatitis B virus antigen, having an addition, deletion, and/or substitution of 1-3 amino acid residues in formula [1], [2], or [3] above.

(7) A hepatitis B virus antigen having a glycan structure that is attached to one and/or both of the contiguous Thr (TT in PTTA) in formula [1], [2], or [3] above, is substituted with NeuAcα2-6, is solely Galβ1-3GalNAc or GalNAc, or has an addition, deletion, and/or substitution of a mono- or di-saccharide glycan.

(8) A method for producing the hepatitis B virus antigen according to any one of (2) to (7), using a glycan synthesis technique.

(9) The production method according to (8), wherein the glycan synthesis technique is biosynthesis by yeast, chemical synthesis, enzymatic synthesis, or a combination of two or more thereof.

(10) A composition for a vaccine, comprising the hepatitis B virus antigen according to any one of (2) to (7) or a hepatitis B virus antigen produced by the production method according to (8) or (9).

(11) An antibody or a phage antibody, which recognizes the hepatitis B virus antigen according to any one of (2) to (7) or a hepatitis B virus antigen produced by the production method according to (8) or (9).

(12) The antibody according to (11), which is a mouse antibody, a rat antibody, an alpaca antibody, a horse antibody, a monkey antibody, a rabbit antibody, a goat antibody, a sheep antibody, a human antibody, a humanized antibody, a single-chain antibody (scFv), or a chimeric antibody.

(13) A nucleic acid encoding an anti-hepatitis B virus antigen antibody gene, having the nucleotide sequence represented by SEQ ID NO: 1 or 2.

(14) A nucleic acid having at least 70% homology to the nucleotide sequence represented by SEQ ID NO: 1 or 2.

(15) A nucleic acid which hybridizes to a complementary sequence of the nucleotide sequence represented by SEQ ID NO: 1 or 2 under stringent conditions.

(16) An anti-hepatitis B virus antigen antibody having the amino acid sequence represented by any one of SEQ ID NOs: 3 to 10.

(17) A protein having at least 70% homology to the amino acid sequence represented by any one of SEQ ID NOs: 3 to 10.

(18) A protein having an addition, deletion, and/or substitution of 1-10 amino acid residues in the amino acid sequence represented by any one of SEQ ID NOs: 3 to 10.

(19) A method for detecting hepatitis B virus, using an antibody or protein encoded by the nucleic acid according to any one of (13) to (15), or the antibody or protein according to any one of (16) to (18).

(20) The method according to (19), wherein the hepatitis B virus to be detected is an infectious Dane particle.

(21) A pharmaceutical composition for hepatitis B virus, using an antibody or protein encoded by the nucleic acid according to any one of (13) to (15), or the antibody or protein according to any one of (16) to (18).

[1] A hepatitis B virus antigen, which has a sequence of at least 13 contiguous amino acids comprising amino acid Asn at positions 15, 123, and/or 320 and/or amino acid Thr at positions 156 and/or 157 in the amino acid sequence (SEQ ID NO: 14) of PreS1, PreS2, and S regions, or an amino acid sequence with an addition, deletion, and/or substitution of 1-3 amino acid residues in the sequence of at least 13 contiguous amino acids, and has an N-linked glycan attached to the amino acid Asn at positions 15, 123, and/or 320 and/or an O-linked glycan attached to the amino acid Thr at positions 156 and/or 157, the O-linked glycan comprising GalNAc attached to the amino acid Thr.

[2] The hepatitis B virus antigen according to [1], wherein the hepatitis B virus antigen has the amino acid sequence set forth in SEQ ID NO:15.

[3] The hepatitis B virus antigen according to [1] or [2], wherein the O-linked glycan is NeuAcα2-3Galβ1-3GalNAc.

[4] The hepatitis B virus antigen according to [1] or [2], wherein the O-linked glycan is:
(1) NeuAcα2-6Galβ1-3GalNAc,
(2) Galβ1-3GalNAc,
(3) GalNAc, or
(4) a glycan with an addition, deletion, and/or substitution of a mono- or di-saccharide glycan in (1) to (3).

[5] A composition for a vaccine, comprising the hepatitis B virus antigen according to any one of [1] to [4].

[6] An anti-hepatitis B virus antigen antibody, which specifically binds to the hepatitis B virus antigen according to any one of [1] to [4].

[7] The anti-hepatitis B virus antigen antibody according to [6], comprising:
CDR sequences in the amino acid sequence set forth in SEQ ID NO: 3 and CDR sequences in the amino acid sequence set forth in SEQ ID NO: 4; or
CDR sequences in the amino acid sequence set forth in SEQ ID NO: 5, CDR sequences in the amino acid sequence set forth in SEQ ID NO: 7, or CDR sequences in the amino acid sequence set forth in SEQ ID NO: 9, and CDR sequences in the amino acid sequence set forth in SEQ ID NO: 6, CDR sequences in the amino acid sequence set forth in SEQ ID NO: 8, or CDR sequences in the amino acid sequence set forth in SEQ ID NO: 10.

[8] The anti-hepatitis B virus antigen antibody according to [6] or [7], having the amino acid sequences set forth in SEQ ID NOs: 3 and 4; or the amino acid sequence set forth in SEQ ID NO: 5, 7, or 9 and the amino acid sequence set forth in SEQ ID NO: 6, 8, or 10.

[9] A nucleic acid encoding an amino acid sequence of the anti-hepatitis B virus antigen antibody according to [6].

[10] The nucleic acid according to [9], comprising the nucleotide sequence set forth in SEQ ID NO: 1 or 2.

[11] An expression vector comprising the nucleic acid according to [9] or [10].

[12] An anti-hepatitis B virus pharmaceutical composition, comprising the antibody according to any one of [6] to [8].

[13] A method for detecting a Dane particle of hepatitis B virus, using the antibody according to any one of [6] to [8].

[14] The method according to [13], further comprising using a lectin.

[15] A kit for detecting a Dane particle of hepatitis B virus, comprising the antibody according to any one of [6] to [8].

[16] A method for preventing hepatitis B virus infection, comprising administering the hepatitis B virus antigen according to any one of [1] to [4].

[17] A method for treating a hepatitis B virus infection, comprising administering the antibody according to any one of [6] to [8].

[18] A method for detecting an infection by hepatitis B virus, comprising: contacting a sample obtained from a patient suspected of being infected by hepatitis B virus with the antibody according to any one of [6] to [8]; concentrating a complex containing the antibody; and detecting hepatitis B virus DNA from the obtained concentrate.

[19] A method for concentrating a Dane particle of hepatitis B virus, comprising contacting a Jacalin lectin with a sample that may comprise a Dane particle of hepatitis B virus.

[20] A method for detecting whether a sample contains a Dane particle of hepatitis B virus, comprising: contacting a Jacalin lectin with a sample; concentrating a complex of the Jacalin lectin and a Dane particle of hepatitis B virus; and detecting hepatitis B virus DNA from the obtained concentrate.

[21] A kit for detecting a Dane particle of hepatitis B virus, comprising a Jacalin lectin.

Effects of Invention

According to the present invention, techniques and products for acquiring examination systems that can recognize Dane particles without recognizing the subviral particles of hepatitis B virus (HBV), hepatitis B virus antigens that can be used as a vaccine capable of inducing the production of antibodies capable of recognizing Dane particles without recognizing the subviral particles, or neutralizing antibodies that recognize Dane particles without recognizing the subviral particles and that exhibit infection-inhibiting effects are provided.

BRIEF DESCRIPTION OF DRAWINGS

FIG. 3 shows a non-destructive glycomic analysis of HBV particles.
FIG. 5 shows HBV separation (HBV DNA) by a Jacalin lectin.

Figure 1:
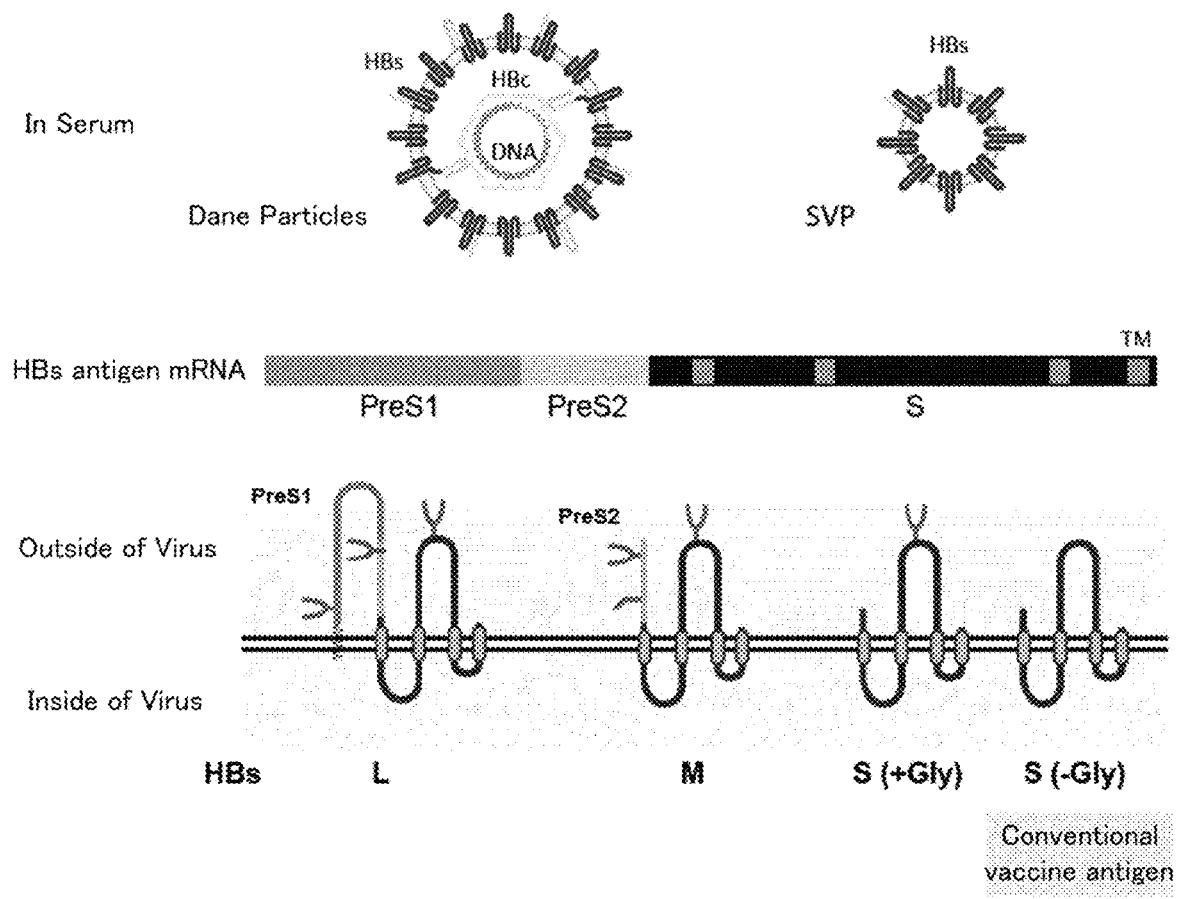
FIG. 1 shows HBV particles and the target of current vaccines.

A method for culturing a transformed host cell in a medium can be performed according to a conventional method used for culturing the host cell.

When the transformed host cell is a yeast, either a natural medium of a synthetic medium may be used as the culturing medium, as long as it contains a carbon source, a nitrogen source, an inorganic salt, etc. which can be utilized by yeast, and allows efficient culturing of the transformant. As the carbon source, any carbon source can be used as long as it can be utilized by yeast, and carbohydrates such as glucose, fructose, sucrose, and starch, organic acids such as acetic acid and propionic acid, and alcohols such as ethanol and propanol can be used. As the nitrogen source, in addition to ammonium salts of inorganic acids or organic acids, such as ammonia, ammonium chloride, ammonium sulfate, ammonium acetate, and ammonium phosphate, or other nitrogen-containing compounds, peptone, meat extracts, corn steep liquor, etc. can be used. As the inorganic salt, monopotassium phosphate, dipotassium phosphate, magnesium phosphate, magnesium sulfate, sodium chloride, ferrous sulfate, manganese sulfate, copper sulfate, calcium carbonate, etc. can be used. In addition, an antibiotic such as aureobasidin, ampicillin, or tetracycline may be appropriately added to the medium depending on the type of the selection marker, or an amino acid, which can be supplied by an auxotrophy-complementing gene (Leu, Ura, Trp, etc.), may be excluded from the medium.

When the transformed host cell, e.g., a yeast, is cultured, the medium is suitably adjusted to a pH of 4-7. Moreover, the culture temperature is 15-32° C. and is preferably about 28° C. When a protein with a complex conformation is expressed, it may be preferable to culture at low temperatures so that folding of the protein is more efficiently performed in the cell. The culture time is about 24-1000 hours, and culturing can be performed by batch culture, continuous culture, etc. under static, shaking, stirring, or aerated conditions.

The expression product of the glycoprotein gene from the above culture (culture supernatant, cultured bacteria, etc.) can be confirmed by silver staining or protein staining following SDS-PAGE, Western analysis, ELISA, etc.

In order to isolate and purify the produced glycoprotein, a conventional method for isolating and purifying a glycoprotein may be used. After culturing, when the target glycoprotein is produced inside a bacterium or a cell, the target glycoprotein is collected by homogenizing the bacterium or the cell by an ultrasonic homogenizer, a French press, a Manton-Gaulin homogenizer, a dynomill, or the like. In addition, when the target glycoprotein is produced outside the bacterium or outside the cell, the culture solution is used as-is or is subjected to centrifugation or the like to remove the bacterium or the cell. The target glycoprotein may be subsequently collected by, e.g., extraction with an organic solvent, and isolated and purified, as necessary, by using techniques such as various chromatographies (hydrophobic chromatography, reverse phase chromatography, affinity chromatography, ion exchange chromatography, etc.), gel filtration using a molecular sieve, electrophoresis using a polyacrylamide gel or the like, alone or in combination.

The culture method and purification method are illustrated in the examples above but are not limited thereto. Moreover, the amino acid sequence of the purified gene product can be confirmed by a known amino acid analysis, e.g., automatic amino acid sequencing by Edman degradation, or the like.

(Chemical synthesis)

Peptides which are part of the HBs glycoproteins of the present invention can be very easily synthesized by chemical techniques such as solid phase methods and liquid phase methods commonly used for peptide synthesis. Peptides can also be obtained by asking a manufacturing company that provides peptide synthesis services.

(Enzymatic synthesis)

It is possible to obtain a hepatitis B virus antigen derived from a glycosylated HBs glycoprotein by using any type of glycosyltransferase on a peptide that is part of the HBs glycoprotein of the present invention. In the present invention, the enzymatic synthesis method preferably used is a method involving chemically synthesizing a glycopeptide with N-acetylgalactosamine attached to the threonine residue at positin 37 and/or 38 from the N-terminus of PreS2 (SEQ ID NO: 11), attaching a galactose to the N-acetylgalactosamine using a recombinant Glycoprotein-N-acetylgalactosamine 3-beta-galactosyltransferase 1 (C1GALT1), and attaching sialic acid to the galactose using a recombinant ST3 beta-galactoside alpha-2,3-sialyltransferase 1 (ST3Gal1).

Further, an antigen can also be obtained by hydrolyzing an obtained HBs glycoprotein by an enzymatic treatment or the like according to conventional enzymatic treatment or the like with a proteolytic enzyme, and separating and purifying a glycopeptide from the hydrolysates.

[Hepatitis B Virus]

The term "HBV" herein refers to a virus with the ability to cause the onset of hepatitis B. HBV is currently known to include genotypes A to H, and all of the genotypes are included in the HBV to be treated and suppressed in the pharmaceutical composition for HBV infections of the present invention.

Moreover, the "HBV infection" mentioned in the present invention is typically hepatitis B, classified as chronic hepatitis, acute hepatitis, or fulminant hepatitis. If there are symptoms induced by HBV infection of organisms including humans, not only hepatitis B but also cirrhosis, liver fibrosis, and liver cancers such as hepatocellular carcinoma are included. Whether it is an HBV infection can be determined, for example, by detecting HBsAg in the blood, detecting HBe antigen in the blood, measuring HBV-DNA content in the blood, and measuring the DNA polymerase content of HBV in the blood, and a combination thereof.

The "treatment of HBV infection" mentioned herein refers to HBV elimination, reduction of symptoms due to HBV infection, hepatitis relief, and inhibition and reduction of the progression from hepatitis to cirrhosis, liver fibrosis, and liver cancer. In addition, the expression "treatment or suppression of HBV infection" may be used to clarify the inclusion of aspects in which the symptoms and progression of an HBV infection are reduced though remission of the HBV infection is not achieved. Moreover, "prevention of HBV infection" refers to preventing the onset of an HBV infection such as hepatitis B before or after infection by HBV.

[Dane Particles]

As mentioned above, HBV in the body is present with a much greater proportion of non-infectious (nucleic acid free) subviral particles than infectious (nucleic acid-containing) virus particles (also referred to as Dane particles), and the current HBsAg measurement systems cannot accurately measure only the infectious Dane particles. However, in the present invention, it was elucidated that Dane particles are associated with specific glycan structures, leading to the successful construction of a new detection system using the same.

Further, as mentioned above, although the safety of blood donations is ensured by screening with nucleic acid tests (NAT), HBV infection is established at a low copy at or below the detection limit, so infectious accidents caused by blood transfusions still take place compared with HCV and HIV. That is, techniques to concentrate Dane particles are essential to increase the accuracy of HBV detection.

Using a technique concentrating Dane particles, infection by hepatitis B virus can be detected with higher sensitivity by concentrating Dane particles in the sample and detecting the DNA of hepatitis B virus from the resulting concentrate. Moreover, this technique may enable detection of occult infection by hepatitis B virus.

As shown below, it is possible to concentrate Dane particles by using an antibody of the present invention and a Jacalin lectin.

[HBs Glycoprotein]

HBsAg are envelope glycoproteins of HBV, which start from different methionine (Met) codons from one HBs gene and exist in three species: L-HBs, M-HBs, and S-HBs, based on their sizes.

HBsAgs undergo glycan modifications in the endoplasmic reticulum and Golgi after ribosomal translation in the cells. The core (HBc) that encapsulates HBV DNA (RNA) is incorporated into the envelope containing HBsAgs in the endoplasmic reticulum to form infectious HBV particles (see Schaedler S et al, Viruses. 2009 September; 1(2):185-209, Grimm D et al, Hepatol Int. 2011 June; 5(2): 644-53).

This glycan modification of HBsAgs is an essential, critical step for the formation/secretion of infectious HBV particles (Non-Patent Document 1).

Unless otherwise indicated, the HBs proteins or peptides, or HBs glycoproteins or peptides herein encompass envelope proteins or peptides of HBV of all genotypes A to H.

The hepatitis B virus antigens of the present invention are glycopeptides derived from envelope (HBs) glycoproteins of HBV particles (Dane particles). The hepatitis B virus antigens of the present invention are useful for concentrating infectious Dane particles, for specific detection, and for diagnosing infection by said detection, and are also useful as active ingredients in vaccines for preventing infection by hepatitis B virus.

The hepatitis B virus antigen have a sequence of at least 13 contiguous amino acids comprising amino acid Asn at positions 15, 123 and/or 320 and/or amino acid Thr at positions 156 and/or 157 in the amino acid sequence (SEQ ID NO: 14) of PreS1, Pres2 and S regions. Here, the amino acid sequence of the hepatitis B virus antigen is not limited as long as it can exert its function as an antigen according to the application of the hepatitis B virus antigen, and may be an amino acid sequence of at least 13 contiguous amino acids, with an addition, deletion, and/or substitution of 1-3 amino acid residues, but preferably has the amino acid sequence of SEQ ID NO: 14, more preferably the amino acid sequence of SEQ ID NO: 11, still more preferably the amino acid sequence of SEQ ID NO: 12, and most preferably the amino acid sequence of SEQ ID NO: 15.

The hepatitis B virus antigen may have an O-linked glycan attached to the amino acid Thr at positions 156 and/or 157 in a peptide having the above amino acid sequence, and the O-linked glycan may include a GalNAc attached to the amino acid Thr. Here, the O-linked glycan preferably contains GalNAc and may be a glycan with an addition, deletion, and/or substitution of a mono- or di-saccharide glycan in the GalNAc as long as the hepatitis B virus antigen can exert the function as an antigen according to its application. Moreover, the O-linked glycan more preferably contains Galβ1-3GalNAc, and may be a glycan with an addition, deletion, and/or substitution of a mono- or di-saccharide glycan in the Galβ1-3GalNAc as long as the hepatitis B virus antigen can exert the function as an antigen according to its application. The O-linked glycan is even more preferably NeuAcα2-3Galβ1-3GalNAc, and may be a glycan with an addition, deletion, and/or substitution of a mono- or di-saccharide glycan in NeuAcα2-6Galβ1-3GalNAc or Galβ1-3GalNAc as long as the hepatitis B virus antigen can exert the function as an antigen according to its application.

The hepatitis B virus antigen may have an N-linked glycan attached to amino acid Asn at positions 15, 123 and/or 320 in a peptide having the above amino acid sequence. Here, the N-linked glycan is preferably $(Hex)_2(HexNAc)_2(NeuAc)_2+(Man)_3(GlcNAc)_2$, $(Hex)_2(HexNAc)_2(NeuAc)_1+(Man)_3(GlcNAc)_2$, or $(Hex)_2(HexNAc)_2+(Man)_3(GlcNAc)_2$, and may be a glycan with an addition, deletion, and/or substitution of a mono- or di-saccharide glycan in said glycan as long as the hepatitis B virus antigen can exert the function as an antigen according to its application.

[Composition for Vaccine]

An immunogenic composition such as a vaccine can be produced by mixing an immunoadjuvant and an antigen. It is possible to utilize an inorganic immunoadjuvant as the immunoadjuvant. For example, it is possible to utilize aluminum hydroxide, aluminum phosphate, or calcium phosphate, etc. as the inorganic immunoadjuvant. Since calcium phosphate also functions as a carrier, calcium phosphate can also carry a second immunostimulatory factor.

Alternatively, immunization is also possible by encapsulation in a drug delivery system (DDS), such as nanoparticles targeting antigen-presenting cells such as dendritic cells.

[Antibody]

Antibodies of the present invention are antibodies that specifically bind to at least any one of the hepatitis B virus antigens of the present invention.

The antibodies of the present invention can be made according to conventional methods using a glycosylated hepatitis B virus antigen in HBs glycoprotein (PreS1, PreS2, or S region), or a hepatitis B virus antigen derived from HBs glycoprotein, having a structure of formula [1], [2], or [3] above, or a hepatitis B virus antigen as described in the section "HBs Glycoprotein" above, and can include both polyclonal antibodies and monoclonal antibodies.

An antibody of the present invention is preferably an antibody comprising CDR sequences having amino acid sequences respectively having at least 80%, 85%, 90%, 95%, 98%, or 99% sequence identity to the three heavy chain CDR sequences in the amino acid sequence set forth in SEQ ID NO: 3 and the three light chain CDR sequences in the amino acid sequence set forth in SEQ ID NO: 4, and more preferably contains the three heavy chain CDR sequences in the amino acid sequence set forth in SEQ ID NO: 3 and the three light chain CDR sequences in the amino acid sequence set forth in SEQ ID NO: 4.

A separate antibody of the present invention is preferably an antibody comprising CDR sequences having amino acid sequences respectively having at least 80%, 85%, 90%, 95%, 98%, or 99% A sequence identity to the three heavy chain CDR sequences in the amino acid sequence set forth in SEQ ID NO: 5, CDR sequences having amino acid sequences respectively having at least 80%, 85%, 90%, 95%, 98%, or 99% sequence identity to the three heavy chain CDR sequences in the amino acid sequence set forth in SEQ ID NO: 7, or CDR sequences having amino acid sequences respectively having at least 80%, 85%, 90%, 95%, 98%, or 99% sequence identity to the three heavy chain CDR sequences in the amino acid sequence set forth in SEQ ID NO: 9, and CDR sequences having amino acid sequences respectively having at least 80%, 85%, 90%, 95%, 98%, or 99% sequence identity to the three light chain CDR sequences in the amino acid sequence set forth in SEQ ID NO: 6, CDR sequences having amino acid sequences respectively having at least 80%, 85%, 90%, 95%, 98%, or 99% sequence identity to the three light chain CDR sequences in the amino acid sequence set forth in SEQ ID NO: 8, or CDR sequences having amino acid sequences respectively having at least 80%, 85%, 90%, 95%, 98%, or 99% sequence identity to the three light chain CDR sequences in the amino acid sequence set forth in SEQ ID NO: 10. The antibody is more preferably an antibody comprising the three heavy chain CDR sequences in the amino acid sequence set forth in SEQ ID NO: 5, the three heavy chain CDR sequences in the amino acid sequence set forth in SEQ ID NO: 7, or the three heavy chain CDR sequences in the amino acid sequence set forth in SEQ ID NO: 9, and the three light chain CDR sequences in the amino acid sequence set forth in SEQ ID NO: 6, the three light chain CDR sequences in the amino acid sequence set forth in SEQ ID NO: 8, or the three light chain CDR sequences in the amino acid sequence set forth in SEQ ID NO: 10.

Moreover, examples of combinations of heavy chain CDR sequences and light chain CDR sequences include: the heavy chain CDR and light chain CDR sequences in the amino acid sequences set forth in SEQ ID NO: 5 and SEQ ID NO: 8, the heavy chain CDR and light chain CDR sequences in the amino acid sequences set forth in SEQ ID NO: 5 and SEQ ID NO: 9, the heavy chain CDR and light chain CDR sequences in the amino acid sequences set forth in SEQ ID NO: 5 and SEQ ID NO: 10, the heavy chain CDR and light chain CDR sequences in the amino acid sequences set forth in SEQ ID NO: 6 and SEQ ID NO: 8, the heavy chain CDR and light chain CDR sequences in the amino acid sequences set forth in SEQ ID NO: 6 and SEQ ID NO: 9, the heavy chain CDR and light chain CDR sequences in the amino acid sequences set forth in SEQ ID NO: 6 and SEQ ID NO: 10, the heavy chain CDR and light chain CDR sequences in the amino acid sequences set forth in SEQ ID NO: 7 and SEQ ID NO: 8, the heavy chain CDR and light chain CDR sequences in the amino acid sequences set forth in SEQ ID NO: 7 and SEQ ID NO: 9, and the heavy chain CDR and light chain CDR sequences in the amino acid sequences set forth in SEQ ID NO: 7 and SEQ ID NO: 10. Moreover, the CDR sequences may have amino acid sequences respectively having at least 80%, 85%, 90%, 95%, 98%, or 99% sequence identity to these heavy chain CDR sequences and light chain CDR sequences.

This other antibody is an antibody comprising CDR sequences having amino acid sequences respectively having at least 80%, 85%, 90%, 95%, 98%, or 99% sequence identity to the three heavy chain CDR sequences in the amino acid sequence set forth in SEQ ID NO: 5 and CDR sequences having amino acid sequences respectively having at least 80%, 85%, 90%, 95%, 98%, or 99% sequence identity to the three light chain CDR sequences in the amino acid sequence set forth in SEQ ID NO: 6; more preferably an antibody comprising CDR sequences having amino acid sequences respectively having at least 80%, 85%, 90%, 95%, 98%, or 99% sequence identity to the three heavy chain CDR sequences in the amino acid sequence set forth in SEQ ID NO: 7 and CDR sequences having amino acid sequences respectively having at least 80%, 85%, 90%, 95%, 98%, or 99% sequence identity to the three light chain CDR sequences in the amino acid sequence set forth in SEQ ID NO: 8, or CDR sequences having amino acid sequences respectively having at least 80%, 85%, 90%, 95%, 98%, or 99% sequence identity to the three heavy chain CDR sequences in the amino acid sequence set forth in SEQ ID NO: 9 and CDR sequences having amino acid sequences respectively having at least 80%, 85%, 90%, 95%, 98%, or 99% sequence identity to the three light chain CDR sequences in the amino acid sequence set forth in SEQ ID NO: 10. The antibody is more preferably an antibody comprising the three heavy chain CDR sequences in the amino acid sequence set forth in SEQ ID NO: 5 and the three light chain CDR sequences in the amino acid sequence set forth in SEQ ID NO: 6, an antibody comprising the three heavy chain CDR sequences in the amino acid sequence set forth in SEQ ID NO: 7 and the three light chain CDR sequences in the amino acid sequence set forth in SEQ ID NO: 8, or an antibody comprising the three heavy chain CDR sequences in the amino acid sequence set forth in SEQ ID NO: 9 and the three light chain CDR sequences in the amino acid sequence set forth in SEQ ID NO: 10.

The antibodies of the present invention may be low molecular weight antibodies, and antibody fragments in which a portion of the full-length antibody is lacking are also acceptable, i.e., the antibodies may be antigen-binding fragments, as long as they bind to the hepatitis B virus antigen of the present invention.

Examples of monoclonal antibodies include antibodies that can be produced from hybridomas obtained by fusing a myeloma cell and an antibody-producing cell immunized with the antigen, antibodies that can be produced in hosts transformed with expression vectors containing an antibody gene by genetic engineering techniques, and antibodies that specifically bind to the same epitope as these antibodies of the present invention. The antibody may be a chimeric antibody, a humanized antibody, a human antibody, or an antibody from a library. The species from which the antibody is derived is not particularly limited.

Further, the antibody may be a bispecific antibody. A bispecific antibody refers to an antibody having, in the same antibody molecule, variable regions that recognize different epitopes, but the epitopes may be present in different molecules or may be present in the same molecule. Methods for producing bispecific antibodies are known. For example, two antibodies recognizing different antigens can be conjugated to produce a bispecific antibody. The antibodies to be conjugated may be half antibody molecules each having a heavy chain and a light chain, or may be quarter antibody molecules consisting only of a heavy chain. Alternatively, hybridomas producing different monoclonal antibodies can be fused to generate bispecific antibody-producing fused cells. In addition, bispecific antibodies can be made by genetic engineering techniques.

[Preparation of Antibody]

The monoclonal antibodies of the present invention can be generated, for example, by methods (hybridoma method, phage display method, etc.) known to those skilled in the art, as described below.

Hybridomas can be generated by obtaining antibody-producing B cells from the spleens, lymph nodes, or peripheral blood of antigen-immunized mice, or antibodies can be generated from cDNAs obtained from immunized mice.

Specifically, monoclonal antibodies against a glycosylated hepatitis B virus antigen in HBs glycoprotein (PreS1, PreS2, or S region), or a hepatitis B virus antigen derived from HBs glycoprotein, having the structure of formula [1], [2], or [3] above, or a hepatitis B virus antigen as described in the "HBs Glycoprotein" section above can be made by administering to a mammal the glycosylated hepatitis B virus antigen in HBs glycoprotein (PreS1, PreS2, or S region), the hepatitis B virus antigen derived from HBs glycoprotein, having the structure of formula [1], [2], or [3] above, or the hepatitis B virus antigen as described in the "HBs Glycoprotein" section above, i.e., by administering the antigen itself or together with a carrier or diluent to a site capable of antibody production. As a carrier, an antigenicity-stimulating carrier protein, e.g., keyhole limpet hemocyanin (KLH), bovine serum albumin (BSA), bovine thyroglobulin, ovalbumin (OVA), etc. can be used. The mix ratio of the carrier to the antigen peptide may be any ratio so long as antibodies can be efficiently made against the immunized antigen peptide crosslinked to the carrier, and for example, a method in which the carrier is conjugated at a ratio, by weight, of about 0.1 to 20, preferably about 1 to 5, relative to 1 antigen is used. Various condensing agents can be used for the conjugation of the antigen and the carrier, and glutaraldehyde, carbodiimide, maleimide active ester, thiol group-, dithiopyridyl group-containing active ester reagents, etc. can be used.

Various adjuvants (antigenicity enhancers), such as complete Freund's adjuvant or incomplete Freund's adjuvant, may be administered to enhance antibody production upon administration. Administration is usually carried out once every 2-6 weeks for a total of about 2-10 times. Examples of mammals used include monkeys, rabbits, dogs, guinea pigs, mice, rats, alpacas, sheep, goats, and hamsters, but selection is preferably made in consideration of the mammal's compatibility with myeloma cells used for cell fusion, and generally, mice, rats, hamsters, etc. are preferably used.

In the generation of monoclonal antibody-producing cells, monoclonal antibody-producing hybridomas can be prepared by selecting individuals with confirmed antibody titers from antigen-immunized mammals, e.g., mice, harvesting spleens or lymph nodes 2-5 days after the final immunization, and fusing the antibody-producing cells contained therein with myeloma cells. Measurement of antibody titers in antisera can be performed according to methods well known to those skilled in the art, such as ELISA. For example, mention may be made of methods involving adding an antiserum to a solid phase (e.g., microplate) to which an antigen peptide used as an immunogen is adsorbed directly or together with a carrier, then adding an anti-immunoglobulin antibody (when a mouse cell is used for cell fusion, an anti-mouse immunoglobulin antibody is used) labeled with a radioactive substance, an enzyme, etc., or Protein A or Protein G, and detecting a monoclonal antibody bound to the solid phase. Fusion manipulations can be carried out according to known methods, e.g., the method of Köhler and Milstein [Nature, 256, 495 (1975)]. Examples of fusion promoters include polyethylene glycol (PEG) and Sendai virus, and PEG is preferably used.

Examples of myeloma cells include NS-1, NS0, P3U1, and SP2/0, and SP2/0 is preferably used. The ratio of the number of antibody-producing cells (spleen cells) used to the number of myeloma cells is preferably about 1:1 to 20:1, and PEG (preferably PEG1000 to PEG6000) is added at a concentration of about 10-80%, and cell fusion can be efficiently performed by incubating at about 20-40° C., preferably about 30-37° C., for about 1-10 minutes.

Various methods can be used in the screening of monoclonal antibody-producing hybridomas, and examples thereof include methods involving adding a hybridoma culture supernatant to a solid phase (e.g., microplate) to which an antigen used as an immunogen is adsorbed directly or together with a carrier, then adding an anti-immunoglobulin antibody (when a mouse cell is used for cell fusion, an anti-mouse immunoglobulin antibody is used) labeled with a radioactive substance, an enzyme, etc., or Protein A or Protein G, and detecting a monoclonal antibody bound to the solid phase, and methods involving adding a hybridoma culture supernatant to a solid phase to which an anti-immunoglobulin antibody or Protein A is adsorbed, adding an antigen peptide labeled with a radioactive substance, an enzyme, etc., and detecting a monoclonal antibody bound to the solid phase.

Screening of monoclonal antibodies can be performed according to known or equivalent methods, but usually can be performed in media for animal cells, etc. to which HAT (hypoxanthine, aminopterin, thymidine) is added. As the medium for screening and growth, any medium can be used as long as it allows hybridomas to grow. For example, RPMI 1640 medium containing 1-20%, preferably 10-20% fetal bovine serum, GIT medium (Wako Pure Chemical Industries, Ltd.) or serum-free medium for culturing hybridomas (SFM 101, Nissui Pharmaceutical Co, Ltd.) containing 1-10% fetal bovine serum, serum-free medium for culturing hybridomas (Hybridoma-SFM, Invitrogen) containing 10-20% fetal bovine serum, etc. may be used. The culture temperature is usually 20-40° C. and is preferably about 37° C. The culture time is usually 5 days to 3 weeks and is preferably 1-2 weeks. Culturing can usually be carried out in 5% carbon dioxide gas. The antibody titer of the hybridoma culture supernatant can be measured in the same manner as in the above measurement of antibody titers in antisera.

Further, hybridoma clones tested positive with ELISA against the antigen peptide can be subjected to secondary culture and assessment of their capability to produce antibodies that recognize the antigen by Western blotting by using culture supernatants from the individual clones. Examining whether or not the antigen is detected can-sort out hybridomas producing monoclonal antibodies that specifically recognize the antigen.

The separation and purification of the monoclonal antibody can be carried out according to usual methods for separating and purifying immunoglobulins in the same manner as in the separation and purification of polyclonal antibodies, such as specific purification methods involving using, e.g., salting-out, alcohol precipitation, isoelectric precipitation, electrophoresis, adsorption and desorption with an ion exchanger (e.g., DEAE), ultracentrifugation, gel filtration, an antigen-bound solid phase, or an active adsorbent such as Protein A or Protein G to collect only antibodies, and dissociating the binding to obtain the antibodies.

The monoclonal antibodies of the present invention can also be generated by genetically engineering, by analyzing nucleotide sequences encoding antibodies produced by the above hybridomas and using the sequences to generate antibody-producing plasmids. In addition, the monoclonal antibodies of the present invention can also be genetically engineered, by extracting spleens from animals such as mice immunized with a hepatitis B virus antigen derived from a glycosylated hepatitis B virus antigen in HBs glycoprotein (PreS1, PreS2, or S region), or a hepatitis B virus antigen derived from HBs glycoprotein, having a structure of formula [1], [2], or [3] above, or a hepatitis B virus antigen as described in the section "HBs Glycoprotein," obtaining antibody-producing B cells, using antibody gene-specific primers to determine the nucleotide sequences encoding the antibodies, and generating antibody-producing plasmids.

Polyclonal antibodies against the glycosylated hepatitis B virus antigen in HBs glycoprotein (PreS1, PreS2, or S region), or the hepatitis B virus antigen derived from HBs glycoprotein, having a structure of formula [1], [2], or [3] above, or the hepatitis B virus antigen as described in the section "HBs Glycoprotein" can be made in accordance with known or equivalent methods. Specifically, similar to the above methods for generating monoclonal antibodies, antibodies can be made by administering a glycosylated hepatitis B virus antigen in HBs glycoprotein (PreS1, PreS2, or S region) or a hepatitis B virus antigen derived from HBs glycoprotein, having a structure of formula [1], [2], or [3] to mammals or chickens at a site capable of antibody production, the antigen being administered by itself or together with a carrier or diluent. A complete Freund's adjuvant or incomplete Freund's adjuvant may be administered to increase antibody production capacity upon administration. Administration can usually be carried out once every 2-6 weeks for a total of about 3-10 times.

Polyclonal antibodies can be collected from the blood, ascites, breast milk, etc., preferably the blood, of mammals immunized in the manner described above, and in the case of chickens, can be collected from the blood and egg yolk.

The measurement of polyclonal antibody titers in antisera, assessment of reactivity to the glycosylated hepatitis B virus antigen in HBs glycoprotein (PreS1, PreS2, or S region), or the hepatitis B virus antigen derived from HBs glycoprotein, having a structure of formula [1], [2], or [3] above, or the hepatitis B virus antigen as described in the section "HBs Glycoprotein," separation and purification of polyclonal antibodies, etc. can be carried out in accordance with the above methods for generating monoclonal antibodies.

An "antigen-binding fragment" of an antibody of the present invention includes a portion of a monoclonal antibody of the present invention, preferably an antigen binding region or a variable region thereof, and exhibits binding to the glycosylated hepatitis B virus antigen in HBs glycoprotein (PreS1, PreS2, or S region), or the hepatitis B virus antigen derived from HBs glycoprotein, having a structure of formula [1], [2], or [3] above, or the hepatitis B virus antigen as described in the section "HBs Glycoprotein." Specific examples of the fragment include, for example, Fv, scFv, Fab, F(ab')$_2$, Fab', Fd, dAb, CDR, scFv-Fc fragments, nanobodies, affibodies, diabodies, avimers, minibodies, and versabodies.

These fragments can be obtained using methods well known to those skilled in the art, and specifically, an antibody can be treated with an enzyme, e.g., papain, pepsin, etc. to produce an antibody fragment, or genes encoding these antibody fragments may be constructed, introduced into expression vectors, and then expressed in suitable host cells. The obtained fragment can be assessed for reactivity, specificity, etc. with the antigen in the same manner as the antibody of the present invention.

Moreover, antibodies that are used in the present invention are preferably mouse antibodies, rat antibodies, alpaca antibodies, horse antibodies, monkey antibodies, rabbit antibodies, goat antibodies, sheep antibodies, human antibodies, humanized antibodies, single chain antibodies (scFv), or chimeric antibodies.

[Lectin Array]

A lectin array has multiple discriminant (probe) lectins of different specificities anchored (arrayed) on one substrate in parallel, allowing simultaneous analysis of which lectin interacted with the glycoconjugate subjected to the analysis and how strong the interaction is. By using a lectin array, information necessary for glycan structural estimation can be obtained in a single analysis, and the operation process from sample preparation to scanning can be quickly and conveniently performed. Glycoproteins cannot be analyzed directly by glycan profiling systems such as mass spectrometry, and must be processed into the glycopeptide or free glycan state in advance. Meanwhile, in lectin microarrays, there is an advantage that, for example, the introduction of a fluorophore directly into a core protein portion is enough to allow analysis as-is.

Lectins used in lectin arrays include those shown in Tables 1 and 2 below.

TABLE 1

| | Lectins | Origin | Binding specificity (Carbohydrate-binding specificity) |
|---|---|---|---|
| 1 | LTL | Lotus tetragonolobus | Fucα1-3GlcNAc, Sia-Le$^x$ and Le$^x$ |
| 2 | PSA | Pisum sativum | Fucα1-6GlcNAc and α-Man |
| 3 | LCA | Lens culinaris | Fucα1-6GlcNAc and α-Man, α-Glc |
| 4 | UEA-I | Ulex europaeus | Fucα1-2LacNAc |
| 5 | AOL | Aspergillus oryzae | Terminal αFuc and ±Sia-Le$^x$ |
| 6 | AAL | Aleuria aurantia | Terminal αFuc and ±Sia-Le$^x$ |
| 7 | MAL | Maackia amurensis | Siaα 2-3Gal |
| 8 | SNA | Sambucus nigra | Siaα 2-6Gal/GalNAc |
| 9 | SSA | Sambucus sieboldiana | Siaα 2-6Gal/GalNAc |
| 10 | TJA-I | Trichosanthes japonica | Siaα 2-6Galβ1-4GlcNAcβ-R |
| 11 | PHA(L) | Phaseolus vulgaris | Tri- and tertra-antennary complex oligosaccharides |
| 12 | ECA | Erythrina cristagalli | Lac/LacNAc |
| 13 | RCA120 | Ricinus communis | Lac/LacNAc |
| 14 | PHA(E) | Phaseolus vulgaris | NA2 and bisecting GlcNAc |
| 15 | DSA | Datura stramonium | (GlcNAc)$_n$, polyLacNAc and LacNAc (NA3, NA4) |
| 16 | GSL-II | Griffonia simplicifolia | Agalactosylated N-glycan |
| 17 | NPA | Narcissus pseudonarcissus | non-substituted α1-6Man |
| 18 | ConA | Canavalia ensiformis | α-Man (inhibited by presence of bisecting GlcNAc) |
| 19 | GNA | Galanthus nivalis | non-substituted α1-6Man |
| 20 | HHL | Hippeastrum hybrid | non-substituted α1-6Man |
| 21 | BPL | Bauhinia purpurea alba | Galβ1-3GalNAc and NA3, NA4 |
| 22 | TJA-II | Trichosanthes japonica | Fucα1-2Gal, β-GalNAc > NA3, NA4 |
| 23 | EEL | Euonymus europaeus | Galα1-3[Fucα1-2Gal] > Galα1-3Gal |
| 24 | ABA | Agaricus bisporus | Galβ1-3GalNAcα-Thr/Ser (T) and sialyl-T |
| 25 | LEL | Lycopersicon esculentum | (GlcNAc)$_n$ and polyLacNAc |
| 26 | STL | Solanum tuberosum | (GlcNAc)$_n$ and polyLacNAc |
| 27 | UDA | Urtica dioica | (GlcNAc)$_n$ and polyLacNAc |
| 28 | PWM | Phytolacca americana | (GlcNAc)$_n$ and polyLacNAc |
| 29 | Jacalin | Artocarpus integrifolia | Galβ1-3GalNAcα-Thr/Ser (T) and GalNAcα-Thr/Ser (Tn) |
| 30 | PNA | Arachis hypogaea | Galβ1-3GalNAcα-Thr/Ser (T) |
| 31 | WFA | Wisteria floribunda | Terminal GalNAc (e.g., GalNAcβ1-4GlcNAc |
| 32 | ACA | Amaranthus caudatus | Galβ1-3GalNAcα-Thr/Ser (T) |

TABLE 2

| | Lectins | Origin | Binding specificity (Carbohydrate-binding specificity) |
|---|---|---|---|
| 33 | MPA | Maclura pomifera | Galβ1-3GalNAcα-Thr/Ser (T) and |

TABLE 2-continued

| | Lectins | Origin | Binding specificity (Carbohydrate-binding specificity) |
|---|---|---|---|
| 34 | HPA | Helix pomatia | GalNAcα-Thr/Ser (Tn) Terminal GalNAc |
| 35 | VVA | Vicia villosa | α-, β-linked terminal GalNAc and GalNAcα-Thr/Ser (Tn) |
| 36 | DBA | Dolichos biflorus | GalNAcα-Thr/Ser (Tn) and GalNAcα1-3GalNAc |
| 37 | SBA | Glycine max | Terminal GalNAc (Especially GalNAcα1-3Gal) |
| 38 | GSL-I mixture | Griffonia simplicifolia | α-GalNAc, GalNAcα-Thr/Ser α-Gal |
| 39 | PTL-I | Psophocarpus tetragonolobus | α-GalNAc and Gal |
| 40 | MAH | Maackia amurensis | Siaα 2-3Galβ1-3[Siaα2-6GalNAc] α-R |
| 41 | WGA | Triticum unigaris | (GlcNAc)n and multivalent Sia |
| 42 | GSL-IA$_4$ | Griffonia simplicifolia | α-GalNAc, GalNAcα-Thr/Ser (Tn) |
| 43 | GSL-IB$_4$ | Griffonia simplicifolia | α-Gal |

For example, lectin arrays with 45 lectins immobilized to a substrate (LecChip made by GlycoTechnica Ltd.) are already commercially available.

Lectin arrays have now developed into practical technologies that allow quantitative differential glycan profiling of not only purified preparations but also mixed samples such as sera and cell lysates. Development in the differential glycan profiling of cell-surface glycans is particularly remarkable (Ebe, Y. et al. *J Biochem* (2006) 139, 323-327; Pilobello, K. T. et al. *Proc Natl Acad Sci USA* (2007) 104, 11534-11539; Tateno, H. et al. *Glycobiology* (2007) 17, 1138-1146).

Moreover, data mining by statistical analysis of glycan profiles can be carried out by methods shown in e.g., Kuno A, et al. *J Proteomics Bioinform.* (2008) 1, 68-72, or "The Japanese Society of Carbohydrate Research, 2008/8/18 Development of Applied Technology of Lectin Microarray—Differential Glycan Profiling and Statistical Analysis of Biological Samples—Atsushi Kuno, Atsushi Matsuda, Yoko Itakura, Hideki Matsuzaki, Hisashi Narimatsu, and Jun Hirabayashi," and "Matsuda A, et al *Biochem Biophys Res Commun.* (2008) 370, 259-263".

[Nucleic Acid]

In the present invention, an antibody encoded by an antibody gene cloned from an antibody-producing cell may also be utilized. The cloned antibody gene can be expressed as an antibody by incorporating the gene into a suitable vector and introducing it into a host. Methods for the isolation of antibody genes, introduction into vectors, and transformation of host cells have already been established (see, e.g., Vandamme, A. M. et al, *Eur. J. Biochem.* (1990) 192, 767-775).

For example, a cDNA encoding a variable region (V region) of an antibody of the present invention can be obtained from a hybridoma cell producing the antibody of the present invention. To do so, total RNA is usually extracted first from the hybridoma. As the method for extracting total RNA from cells, for example, guanidine ultracentrifugation (Chirgwin, J. M. et al, *Biochemistry* (1979) 18, 5294-5299), AGPC (Chomczynski, P. et al, *Anal. Biochem.* (1987) 162, 156-159), etc. can be used. The extracted total RNA can be further purified using mRNA Purification Kit (made by GE Healthcare Bioscience), etc. Alternatively, kits for extracting total mRNA directly from cells, such as QuickPrep mRNA Purification Kit (made by GE Healthcare Bioscience), are also commercially available. Such kits can also be used to obtain total mRNA from hybridomas. From the obtained mRNA, cDNA encoding the antibody V-region can be synthesized using a reverse transcriptase. cDNA can be synthesized by AMV Reverse Transcriptase First-strand cDNA Synthesis Kit (made by Seikagaku Corporation), etc. Moreover, 5'-Ampli FINDER RACE Kit (made by Clontech) and 5'-RACE using PCR (Frohman, M. A. et al., *Proc. Natl. Acad. Sci. USA* (1988) 85, 8998-9002; Belyaysky, A. et al., *Nucleic Acids Res.* (1989) 17, 2919-2932) can be used to synthesize and amplify cDNA. Further, in this cDNA synthesis process, appropriate restriction enzyme sites, as described below, can be introduced at both ends of the cDNA.

Target cDNA fragments are purified from the obtained PCR product and then ligated with vector DNA. After such a recombinant vector has been generated and introduced into *E. coli*, etc., and colonies have been selected, a desired recombinant vector can be prepared from *E. coli* that formed the colonies. Whether or not the recombinant vector has a nucleotide sequence of the target cDNA can be confirmed by known nucleotide sequencing methods, e.g., dideoxynucleotide chain termination, etc.

Further, examples of nucleic acids having homology to the nucleotide sequence represented by SEQ ID NO: 1 or 2 include nucleic acids comprising a nucleotide sequence having at least 70%, preferably at least 80%, more preferably at least 90%, and still more preferably at least 95% homology to the nucleotide sequence represented by SEQ ID NO: 1 or 2.

Further, a nucleic acid having homology to the nucleotide sequence represented by SEQ ID NO: 1 or 2 includes a nucleic acid encoding a protein consisting of an amino acid sequence having at least 70%, preferably at least 80% homology to the amino acid sequence represented by SEQ ID NO: 3 or 4, a nucleic acid encoding a protein consisting of a sequence with an addition, deletion, and/or substitution of 1-10 amino acid residues in the amino acid sequence represented by SEQ ID NO: 3 or 4, and a nucleic acid that hybridizes, under a stringent condition, to a complementary nucleotide sequence of the nucleotide sequence represented by SEQ ID NO: 1 or 2.

In addition, the term "stringent condition" described above refers to a condition in which a so-called specific hybrid is formed and a non-specific hybrid is not formed. Examples of such conditions include those in which complementary strands of DNA with high homology, i.e., DNA comprising a nucleotide sequence having at least 70%, preferably at least 80%, more preferably at least 90%, and still more preferably at least 95% homology to the nucleotide sequence represented by SEQ ID NO: 1, hybridize and complementary strands of DNA with a lower homology do not hybridize. More specific conditions for hybridization include conditions having a sodium concentration of 150-900 mM, preferably 600-900 mM, and a temperature of 60-68° C., preferably 65° C.

Introduction of the above mutation (addition, deletion, and/or substitution) can be performed by known or equivalent techniques in the relevant technical field, such as Kunkel or Gapped duplex methods. For example, mutagenesis kits utilizing site-directed mutagenesis (e.g., Mutant-K (made by Takara Bio Inc.) or Mutant-G (made by Takara Bio Inc.)) or kits of the LA PCR in vitro Mutagenesis series of Takara Bio Inc. can be used.

[Protein]

A "protein having at least 70% homology to the amino acid sequence represented by SEQ ID NO: 3 or 4" is a protein having an amino acid sequence having at least 70%, preferably at least 80%, more preferably at least 90%, and most preferably at least 95% homology. Protein homology searches can be performed, for example, in the DNA Databank of JAPAN (DDBJ) using a program such as FASTA or BLAST.

The number of amino acid residues to be added, deleted, and/or substituted in the above "protein having an addition, deletion, and/or substitution of 1-10 amino acid residues in the amino acid sequence represented by SEQ ID NO: 3 or 4" is not particularly limited, but is preferably 10 or fewer, more preferably 7 or fewer, even more preferably 5 or fewer, and still more preferably 3 or fewer.

[Method for Detecting Hepatitis B Virus]

A method for detecting hepatitis B virus in the present invention is characterized in that an antibody induced by a hepatitis B virus antigen of the present invention, or an antibody or a protein encoded by a nucleic acid of the present invention, and/or an antibody or a protein of the present invention is used. The detection system for hepatitis B virus is preferably Western blot, ELISA, etc., but is not particularly limited as long as the system can detect hepatitis B virus.

Dane particles, which are infectious hepatitis B virus (HBV) particles, have been very difficult to detect because they are present in only about $\frac{1}{1000}$ the level of non-infectious SVP, despite being very infectious. According to the method for detecting hepatitis B virus of the present invention (hereinafter, also referred to as a detection method), it is possible to specifically detect HBV Dane particles. Infection testing of HBV Dane particles in transfusions, in which there were constantly infection incidents due to their low levels and high infectivity, can be performed with higher accuracy.

Detection samples in the present detection method include the blood, serum, saliva, semen, vaginal secretions, wound exudates, and other body fluids or tissue extracts of subjects suspected of being infected with hepatitis B virus. Considering the convenience of sample acquisition and handling, blood, serum, and saliva are preferred.

These samples are contacted with the antibody or protein of the present invention according to a conventional method and after appropriate treatment. The antibody or protein of the present invention specifically binds to at least any one of the hepatitis B virus antigens of the invention and thus specifically binds to HBV Dane particles. In the detection method of the present invention, HBV Dane particles thus bound to the antibody or protein, can be directly detected by Western blotting, ELISA, etc., and for example, HBV Dane particles may be detected by further applying PCR, etc. to a sample concentrated by binding to the antibody or protein. This is particularly effective when the sample amount is small or when the concentration of HBV Dane particles in the sample is low.

[Method for Detecting Hepatitis B Virus Using Jacalin]

A method for concentrating Dane particles of the present invention (hereinafter, also referred to as a concentration method) includes a step of contacting an O-linked glycan-binding lectin with the above-described detection sample. The present concentration method may include a step of concentrating a complex of an O-linked glycan-binding lectin and an HBV Dane particle. This step can be carried out, for example, using an O-linked glycan-binding lectin bound to a carrier such as a bead. It is possible to thus concentrate Dane particles in the sample. Here, the O-linked glycan-binding lectin only needs to be a lectin that specifically binds to at least any one of the hepatitis B virus antigens of the present invention, but is preferably a Jacalin lectin.

HBV Dane particles can be detected by further applying PCR, etc. to a sample containing HBV Dane particles concentrated using the present concentration method. O-linked glycan-binding lectins, including Jacalin, can be made into kits for detecting Dane particles of hepatitis B viruses containing the same.

[Diagnosis]

Using the hepatitis B virus detection method of the present invention, the presence or absence of infection by infectious Dane particles can be diagnosed with greater accuracy than conventional methods. This allows the diagnosis to be made even in the earlier stages with mild symptoms, allowing early initiation of treatment and prevention of the spread of infection to others.

[Pharmaceutical Composition]

One of the main embodiments of the pharmaceutical compositions of the present invention is a pharmaceutical composition for the treatment and prevention of HBV infections comprising an antibody or protein as an active ingredient and optionally a pharmaceutically acceptable carrier and/or excipient. In doing so, the antibody or protein of the active ingredient may be incorporated into a known vector capable of liver-specific delivery. Moreover, liposomal delivery, such as pH-sensitive liposomes capable of endoplasmic reticulum-specific delivery, is also preferably used.

The formulation of mainly an antibody, a protein, etc. and specific methods for administration, doses, etc. will be described below.

The route of administration may be either oral or parenteral, and for parenteral administration, it is preferably subcutaneous or intravenous injection, and administration may be by nasal administration such as a nasal spray, transdermal administration, inhalation, suppository, etc. Antibodies or proteins, after being administered to patients by intravenous injection, subcutaneous injection, oral delivery, liposomal delivery, or intranasal delivery, can accumulate in the patient's whole body, liver, or hepatocytes.

"Pharmaceutically acceptable carriers and/or excipients" are known to those skilled in the art and include any type of encapsulant material or formulation auxiliary such as non-toxic solid, semi-solid, or liquid fillers, diluents, liposomes.

Pharmaceutical compositions for parenteral injection may comprise pharmaceutically acceptable sterile aqueous or non-aqueous solutions, dispersions, suspensions, or emulsions, plus sterile powders for reconstitution into sterile injectable solutions or dispersions immediately prior to use. Examples of suitable aqueous and non-aqueous carriers, diluents, solvents, or media include water, polyols such as ethanol, glycerol, propylene glycol, and polyethylene glycol, carboxymethylcellulose and suitable mixtures thereof, vegetable oils such as olive oil, and injectable organic esters such as ethyl oleate. Suitable fluidity can be maintained by blending a coating material such as lecithin, a surfactant, etc. Other agents may also be included, e.g., auxiliaries such as preservatives, wetting agents, emulsifying agents, and dispersing agents, antibacterial agents and antifungal agents, and isotonic agents such as sugars and sodium chloride.

Depot injectable formulations may also be prepared by forming a microcapsule matrix with a biodegradable polymer such as polylactide-polyglycolide or enclosing the pharmaceutical composition within a liposome or microemulsion compatible with body tissue. Injectable formulations can be sterilized, for example, by filtration through a bacterial retention filter or by incorporating a sterilizing agent which takes the form of a sterile solid composition which can be dissolved or dispersed in sterile water or other sterile injectable media immediately prior to use.

Solid dosage forms for oral administration include, but are not limited to, capsules, tablets, pills, powders, and granules. In such solid dosage forms, the active ingredient is mixed with at least one member pharmaceutically acceptable excipient or carrier such as sodium citrate or dicalcium phosphate and/or (a) a filler or bulking agent such as starch, lactose, sucrose, glucose, mannitol, and silicic acid, (b) a binder such as carboxymethylcellulose, arginate, polyvinylpyrrolidone, sucrose, and gum arabic, (c) a wetting agent such as glycerol, (d) a disintegrating agent such as agar, calcium carbonate, potato or tapioca starch, alginic acid, certain silicate, and sodium carbonate, (e) a solution retardant such as paraffin, (f) an absorption enhancer such as a quaternary ammonium compound, (g) a wetting agent such as acetyl alcohol and glycerol monostearate, (h) an absorber such as kaolin and bentonite clay, and (i) a lubricant such as talc, calcium stearate, magnesium stearate, solid polyethylene glycol, sodium lauryl sulfate, and a mixture thereof. In the case of capsules, tablets, and pills, the dosage form may also include buffers.

Other than inert diluents, oral compositions can also include auxiliaries such as wetting agents, emulsifying agents and suspending agents, sweetening agents, flavoring agents, and fragrances, and suspensions may include, in addition to the active compound, for example, suspending agents such as ethoxylated isostearyl alcohols, polyoxyethylene sorbitol, and sorbitan esters, microcrystalline cellulose, aluminum metahydroxide, bentonite, agar, and tragacanth, and mixtures thereof.

Compositions for oral administration may comprise a compressed gas, such as nitrogen or a liquefied gas propellant, comprising a liquid or solid nonionic surfactant to such an extent that the active ingredient does not dissolve, or a solid anionic surfactant.

If the active ingredient is an antibody or protein, it is preferable that the active ingredient rapidly reach HBV-infected cells in the liver by applying liposomal delivery such as pH-sensitive liposomes containing phosphatidylinositol (PI) lipids or cationic liposomes capable of liver-specific delivery.

When other delivery vehicles are used, they are also preferably administered in the form of liposomes. As is known in the relevant technical field, liposomes are generally composed of phospholipids or other lipid substances. Liposomes are formed by monolayered or multilayered hydrate liquid crystals dispersed in an aqueous medium. Any non-toxic, physiologically acceptable and metabolizable lipid capable of forming liposomes can be employed. The present compositions in the form of liposomes can include, in addition to the active ingredient of the present invention, stabilizers, preservatives, excipients, etc. Preferred lipids are phospholipids as well as phosphatidylcholine (lecithin), both natural and synthetic. Methods for forming liposomes are known in the relevant technical field.

EXAMPLES

Below, the present invention will be described in more detail with reference to examples, but the present invention is not limited by these examples.

Figure 2:
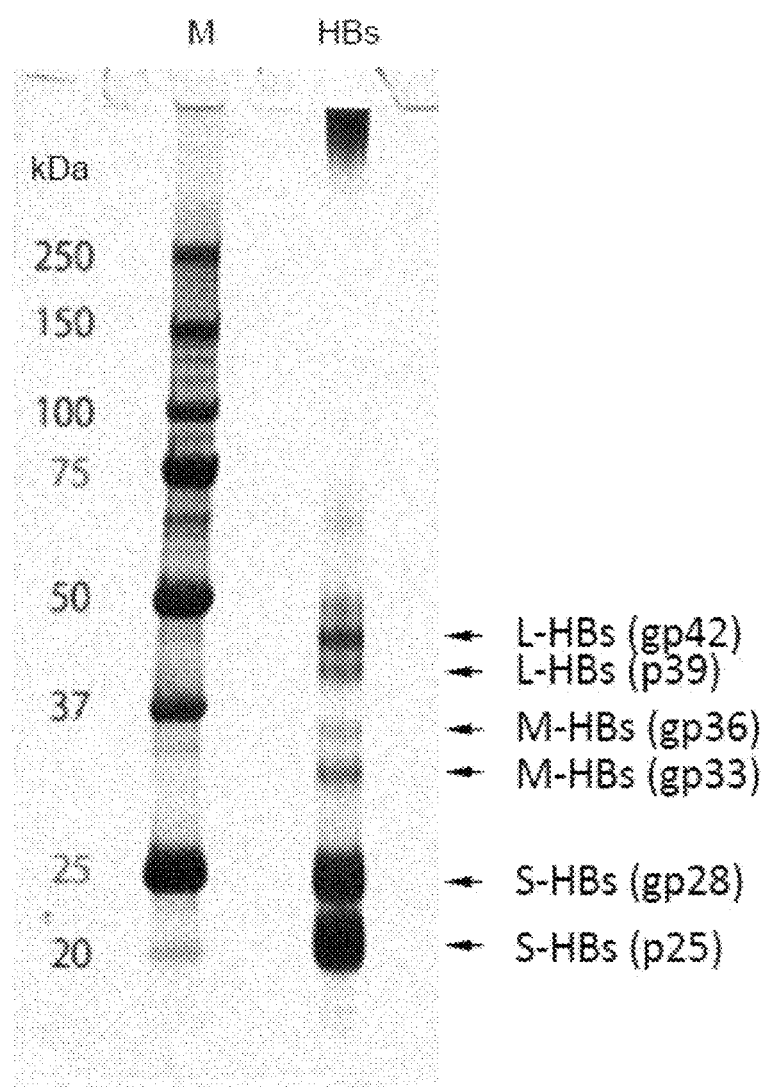
FIG. 2 shows an SDS-PAGE (silver staining) of HBsAg.

To distinguish between Dane particles and SVP, glycosylation and glycan structure analyses were first performed for each HBsAg, focusing on the glycan modification on HBV particles. Particle fractions containing HBV particles were prepared from pooled sera of HBV-infected patients using an ultracentrifugal concentration method. Particle fractions were inactivated by heat treatment at 60° C. overnight and then used for various studies. The concentrated HBV particles were heat-treated at 95° C. for 5 minutes in the presence of 0.4% SDS and a reducing agent (0.2 M dithiothreitol; DTT), then separated with SDS-PAGE (FUJIFILM Wako Pure Chemical Corporation, SuperSep™ Ace, 10-20%) and silver-stained after fixing (FIG. 2).

HBV (HBs) antigens from HBV-infected patients were similarly separated with SDS-PAGE and then transferred onto PVDF membranes (BIO-RAD Inc. Trans-Blot® Turbo™). After blocking (DS Pharma Biomedical Co., Ltd., Block Ace) at 37° C. for 1 hour, an anti S-HBsAg monoclonal antibody (HB0116 antibody, University of Toyama, Jin A. and Muraguchi A. et. al., *Nat Med* (2009) 15(9):1088-1092; Tajiri et. al., *Antiviral Res.* (2010) 87 (1):40-49.) was used to perform Western blotting. Moreover, some were subjected to lectin blotting after having been transferred to PVDF membranes, and the presence or absence of glycan modification was analyzed. In lectin blotting, detection was made by using a biotinylated lectin, performing a secondary reaction with HRP-labeled streptavidin, and using a fluorescence detection reagent. Commercially available biotinylated lectins from Vector (Funacoshi), J-CHEMICAL, Inc. (COSMO BIO), EY-Laboratories (COSMO B10), etc. were used.

Figure 4:
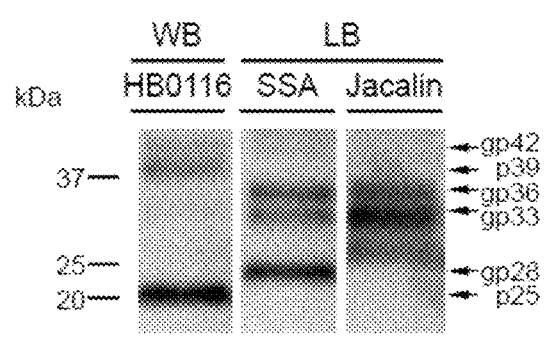
FIG. 4 shows the differences in binding reactivity of lectins with HBV particles.

Further, an immunoprecipitation system was constructed to purify HBV particles present in sera using the HB0116 antibody and to perform glycan structure analysis. An HBV infected model serum (spiked serum) was made by spiking 2.5 µL of a commercially available healthy individual's serum (Kohjin Bio Co., Ltd.) with 250 ng of HBV particles. Immunoprecipitation was performed on 2.5 µL of the spiked serum using 1 µg of the HB0116 antibody, followed by thermal elution at 95° C. for 5 minutes using an eluent (0.2% SDS in TBS). At this time, elution was performed under conditions with 0.2 M DTT (reduction elution) and conditions without the same (non-reduction elution) in the eluent. Lectin microarray analysis was performed using the immunoprecipitated samples and HBsAgs equivalent of 5 ng (FIGS. 3 and 4). The lectin chip (lectin microarray chip) in the lectin microarray analysis used LecChip Ver 1.0 of GlycoTechnica Ltd.

[SDS-PAGE of HBsAgs (Silver Staining) (FIG. 2)]

Particle fractions containing HBV particles prepared from sera of HBV-infected patients were heat-treated in the presence of SDS and a reducing agent and separated with SDS-PAGE. Silver staining after fixation detected S-HBsAg, M-HBsAg, and L-HBsAg bands. The glycosylated and unglycosylated S-HBsAg species (corresponding to gp28 and p25) were present at nearly 1 to 1 and were most abundantly contained.

Antibodies induced after vaccination need to bind to HBV in the blood. Accordingly, glycan analysis was carried out, with the glycoproteins (HBsAg proteins), which constitute the HBV outer shell, as they are in a native or undestroyed state.

[Non-Destructive Glycomic Analysis of HBV Particles (FIG. 3)]

FIG. 3A shows the probe reactivity for the S-HBsAg (gp28 and p25), which is one of the HBsAgs constituting the surface of HBV particles. The figure shows a silver staining image (SS) after electrophoresis, an antibody blot image (Ab) with an antibody (HB0116) having an epitope in a peptide portion of a loop region of S, and a lectin blot image (Lec) with a lectin (SSA) recognizing a terminal sialic acid of a glycan attached to the loop region of S.

FIG. 3B shows an image of non-destructive HBV particle-specific glycan profiling by an antibody-overlaid lectin array using the HB0116 antibody. As mentioned above, there are two S-HBsAg species in HBV particles: gp28 with one N-glycan and p25 without any glycans, existing in a ratio of about 1:1. If HBV particles are obtained without destruction and applied to a lectin array, the glycan on the glycoprotein containing gp28 first binds to the lectin on the chip substrate. After the binding reaction, overlaying the detection antibody HB0116 will result in the antibody reacting to p25 on the particle. In these conditions, a signal can be detected (left panel), but when the HBV particle is destroyed by a surfactant, etc. and there is no protein association, even if the glycoprotein containing gp28 binds to the lectin, the detection antibody will not be able to react, so no signal will be detectable (right panel). In other words, it is possible to profile only the glycans on undestroyed HBV particles by using this approach.

FIG. 3C shows the results of antibody-overlaid lectin arrays of HBV particles separated by ultracentrifugation from HBV patient sera. The figure shows a lectin array analysis of virus particles heat-treated and inactivated under mild conditions after centrifugation (left panel) and a lectin array analysis of destroyed particles by heat-treating obtained particles in the presence of SDS and DTT (right panel). As explained in connection with B, binding signal patterns unique to the glycans on HBV particles are obtained only when the particle shape is retained.

As clearly shown in FIG. 3, lectin blotting performed with lectins presented by the lectin array and an antibody recognizing the HBsAg revealed a clear difference in the molecule species recognized by the antibody and by the lectins. For example, the HBsAg primarily recognized by the monoclonal antibody HB0116 obtained from vaccinees is not recognized by lectin blotting, indicating a recognition of an unglycosylated S-HBsAg. Moreover, the location of the antigenic epitope recognized by HB0116 is thought to be in the C1 region according to reference (Jin A, and Muraguchi A, et al. *Nat Med.* 2009 September; 15(9):1088-92).

From the experimental results of the present application, it is believed that recognition (which is influenced by the binding of the antibody) is not possible due to glycosylation.

[Differences in Binding Reactivity of Lectins to HBV Particles (FIG. 4)]

Lectin blotting was performed using some of the lectins found to bind to HBV particles. SSA recognizing the terminal sialic acid of N-linked glycans showed the strongest binding to gp28, whereas Jacalin recognizing O-linked glycans showed strong binding to gp33.

The lectins were thus found to each exhibit a selective reactivity to a distinct protein component constituting HBV particles, and therefore comparisons were attempted with seven lectins (FIG. 4B). In the selection of these lectins, among the group of lectins which showed a positive signal in the lectin array analysis, seven types of lectins were selected, upon consideration of (1) the overlap of similar specificities of lectins and (2) the minimum combination to provide a range of specificity types for grasping the overall glycan structure of HBV particles. As a result of comparisons with these seven lectins, it was revealed that Jacalin exhibited the highest reactivity to the M proteins gp33 and gp36.

In order to concentrate infectious Dane particles, attempts were made to collect HBV particles using the lectin Jacalin that exhibits a selective reactivity to the M protein among HBsAg proteins.

The sera of patients infected with HBV genotype C were used to construct a collection system for Jacalin reactive HBV particles. Biotin labeled Jacalin (Vector Laboratories) at 5 µg and 10 µg was bound to streptavidin-conjugated magnetic beads (Dynabeads MyOne Streptavidin T1; Life Technologies) at 100 µL, after which serum samples were added and allowed to react by stirring overnight at 4° C. After the reaction, the supernatant was collected as a Jacalin unbound fraction (−), and then a competitor sugar (1 M methyl-α-D-galactopyranoside) was added to Jacalin bound magnetic beads containing HBV particles and allowed to react by stirring overnight at 4° C. The obtained competitor sugar eluate was collected, without heating, as a Jacalin bound fraction (+). In this series of systems, Jacalin unbound magnetic beads (Jacalin, 0 µg) were also prepared as controls in the reaction system. After fractionation into a Jacalin unbound fraction (−) and a Jacalin bound fraction (+) using patient sera at 0.625 µL, HBV DNA was purified from both fractions using QIAamp viral DNA Mini Kit (QIAGEN). Real-time quantitative PCR (Light Cycler 480; Roche Diagnostics) and a Taq polymerase (Eagle Taq Master Mix with ROX; Roche Life Science) were used to quantify the amount of HBV DNA. After thermally denaturing DNA by thermal cycling at 95° C. for 10 minutes, measurements were made in 45 amplification cycles (95° C. for 15 seconds; 60° C. for 1 minute).

The target sequence was amplified using HBV-SF2 (5'-CTTCATCCTGCTGCTATGCCT-3') (SEQ ID NO: 18) and HBV-SR2 (5'-AAAGCCCAGGATGATGGGAT-3') (SEQ ID NO: 19) within the S-HBsAg, and then fluorescently detected using a TaqMan probe and HBV-SP2 (FAM-ATGTTGCCCGTTTGTCCTCTAATTCCAG-TAMRA (SEQ ID NO: 20). Moreover, using 2.5 µL of patient sera, after reacting with Jacalin in the same manner, the amount of HBsAgs present in the two fractions obtained without heating was measured by CLIA (HBsAg QT; Abbott Laboratories) (FIG. 5).

[Separation of HBV by Jacalin Lectin (HBV DNA) (FIG. 5)]

FIG. 5 shows the results of performing affinity chromatography of HBV-infected patient serum components with a carrier with immobilized Jacalin exhibiting a selective reactivity to the M proteins among HBsAg proteins, separating and fractioning HBV particles into a bound fraction (+) and an unbound fraction (−) respectively, obtaining the HBV particles contained in each fraction by immunoprecipitation, and examining their characteristics. Interestingly, it was found that particle-encapsulated HBV DNA retained by infectious Dane particles was predominantly contained in the Jacalin bound fraction (B), but HBsAg that binds to Jacalin takes up only about 5% of the total amount of HBsAg in serum components (C). This means that Jacalin fractionation can enrich Dane particles and can allow for estimation of the total amount of infectious particles.

In order to generate vaccines and antibodies that recognize infectious HBV particles, the glycan structures and glycosylation sites on HBV particles were identified by glycoproteomic analysis using a mass spectrometer as follows.

HBV particles (subviral particle fraction) prepared from HBV-infected patient sera were separated by SDS-PAGE, and HBsAg proteins were detected by silver-staining, then gel pieces of S-, M-, and L-type HBsAg were excised for the respective number of N-glycosylations (S: p25, gp28, M: gp33, gp36, L: p39, gp42, FIG. 2). The gel pieces of the bands were each subjected to a reductive alkylation treatment, then impregnated with trypsin to digest the proteins in the gel, and the resulting peptides were extracted. This was subjected to hydrophilic interaction chromatography (HILIC: using an amide 80 column) and separated into a bound fraction (N-glycopeptide) and a through fraction. A portion of the former was treated with PNGaseF (peptide N glycanase F) in water (buffer) labeled with a stable isotope $^{18}O$ to cleave the glycans and simultaneously label the glycosylation sites (IGOT treatment). Each was subjected to LC/MS analysis. The glycans released from S-HBs gp28 were subjected to an exhaustive methylation treatment followed by compositional analysis of the glycans with MALDI-TOF MS (matrix-assisted LASER desorption ionization-time-of-flight mass spectrometry) (FIG. 6).

[Glycans on HBsAgs (MS and Structure) (FIG. 6)]

Figure 6:
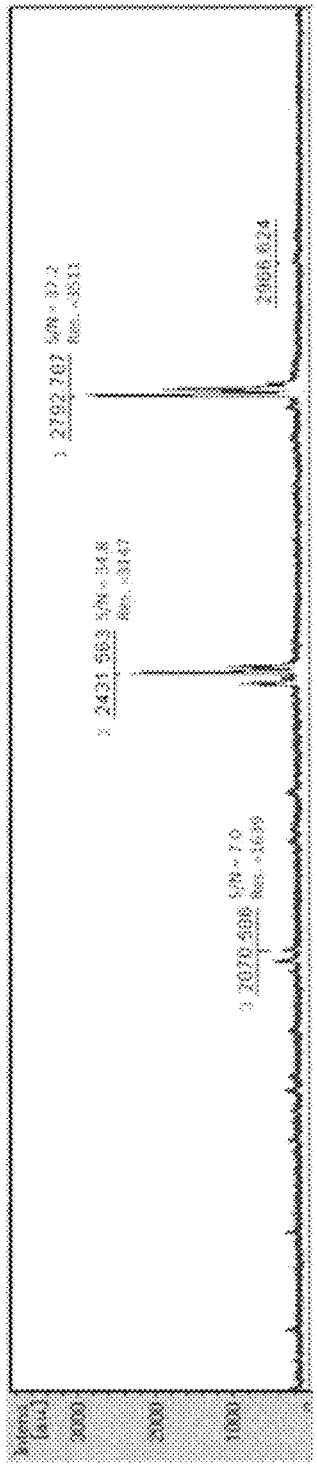
FIG. 6 shows glycans (M expressing genes encoding HBs glycoproteins by known methods, harvesting from the culture, and purifying the glycoproteins. "Culture" means a culture supernatant, as well as any of a cultured cell, a cultured bacterium, or a cell or bacterial homogenate.

FIG. 6 shows the results of analysis using a mass spectrometer to analyze in detail the glycan structures and modifications on HBsAg proteins.

HBV particles (subviral particle fraction) prepared from HBV-infected patient sera were denatured, reductive alkylated, and then digested with trypsin. Glycopeptide fractions collected by HILIC from this digest were subjected to IGOT treatment, which was analyzed by liquid chromatography/mass spectrometry (LC/MS) to identify N-glycosylation sites. The glycopeptides of the respective bands separated by gel electrophoresis and fractionated were also identified by LC/MS spectrometry after IGOT treatment.

The main structures of the N-glycans (FIG. 6) and the N-glycosylation sites (Table 3) were elucidated, and N-glycans on PreS1 and PreS2 were confirmed in addition to the glycan on S-HBs. As shown below, it has been revealed that N-linked glycans are attached to the amino acid Asn at positions 15, 123, and 320 in the amino acid sequence (SEQ ID NO: 14) of PreS1, PreS2, and S regions.

TABLE 3

N-Glycosylation Site

| protein | protein accession | peptide position from | peptide position to | peptide sequence | modified site (sequon) |
|---|---|---|---|---|---|
| L (PreS1. PreS2) | gi\|172045927 | 10 | 35 | KGMGTNLSVPNPLGFFPDHQLDPAFK (SEQ ID NO: 21) | 15(NLS)/ |
| | gi\|172045927 | 11 | 35 | GMGTNLSVPNPLGFFPDHQLDPAFK (SEQ ID NO: 22) | 15(NLS)/ |
| | gi\|138797 | 14 | 135 | DSHPQAMQWNSTTFHQALLDPR (SEQ ID NO: 23) | 123 NST)/ |
| | gi\|138797 | 114 | 137 | DSHPQAMQWNSTTFHQALLDPRVR (SEQ ID NO: 24) | 123(NST)/ |
| M(PreS2) | gi\|77680740 | 1 | 16 | MQWNSTTFHQALLDPR (SEQ ID NO: 25) | 4(NST)/ |
| | gi\|77680740 | 1 | 16 | MQWNSTTFHQALLDPR (SEQ ID NO: 25) | 4(NST)/ |
| | gi\|77680740 | 1 | 16 | MQWNSTTFHQALLDPR (SEQ ID NO: 25) | 4(NST)/ |
| S/M/L | gi\|172045927 | 316 | 334 | PTDGNCTCIPIPSSWAFAK (SEQ ID NO: 26) | 320(NCT)/ |
| | gi\|82035778 | 316 | 334 | PSDGNCTCIPIPSSWAFAK (SEQ ID NO: 27) | 320(NCT)/ |
| | gi\|182032961 | 316 | 334 | PSDGNCTCIPIPSSWAFGK (SEQ ID NO: 28) | 320(NCT)/ |
| | gi\|777680740 | 178 | 215 | TCTIPAQGTSMFPSCCCTKPSDGNCT CIPIPSSWAFAR (SEQ ID NO: 29) | 201(NCT)/ |
| | gi\|77680740 | 197 | 215 | PSDGNCTCIPIPSSWAFAR (SEQ ID NO: 30) | 201(NCT)/ |

The glycans released from HBsAgs were measured by a mass spectrometer, and the mass of the identified peaks and the inferred glycan structures are shown in FIG. 6.

Based on the results of FIGS. 4 and 5, the tryptic digests of HBV sample proteins were subjected to lectin (Jacalin)-immobilized columns, and the obtained glycopeptides were subjected to LC/MS analysis. MS/MS spectra were obtained using collision-induced dissociation (CID) and electron-transfer dissociation (ETD) as the fragmentation methods for selected ions, and the compositions and glycosylation sites were identified. Similarly, HILIC unadsorbed fractions of peptide extracts prepared by excision according to type were subjected to LC/MS analysis to detect the glycopeptides (FIG. 7).

[O-Glycans and Sites on HBsAgs (FIG. 7)]

An analysis was carried out using a mass spectrometer in order to elucidate the attachment sites of O-glycans to which Jacalin binds. Comparisons with known amino acid sequences indicated the presence of an O-glycan in one or two threonines (Thr, T) present in the PreS2 region (FIG. 7).

Figure 7:

An Ms/Ms analysis was performed with a mass spectrometer on the glycopeptides in the PreS2 region, and the mass of the identified peaks and the inferred glycan structures are shown in FIG. 7.

HBsAgs present in HBV-infected individuals' sera were digested with a protease and then analyzed by LC/MS. For the obtained MS/MS spectra, searches were performed using a protein sequence database generated to contain previously reported amino acid sequences of HBs of various genotypes and using a database search engine (Mascot). (FIG. 8)

[Sequences (genotype C) of Identified HBsAg (FIG. 8)]

Figure 8:
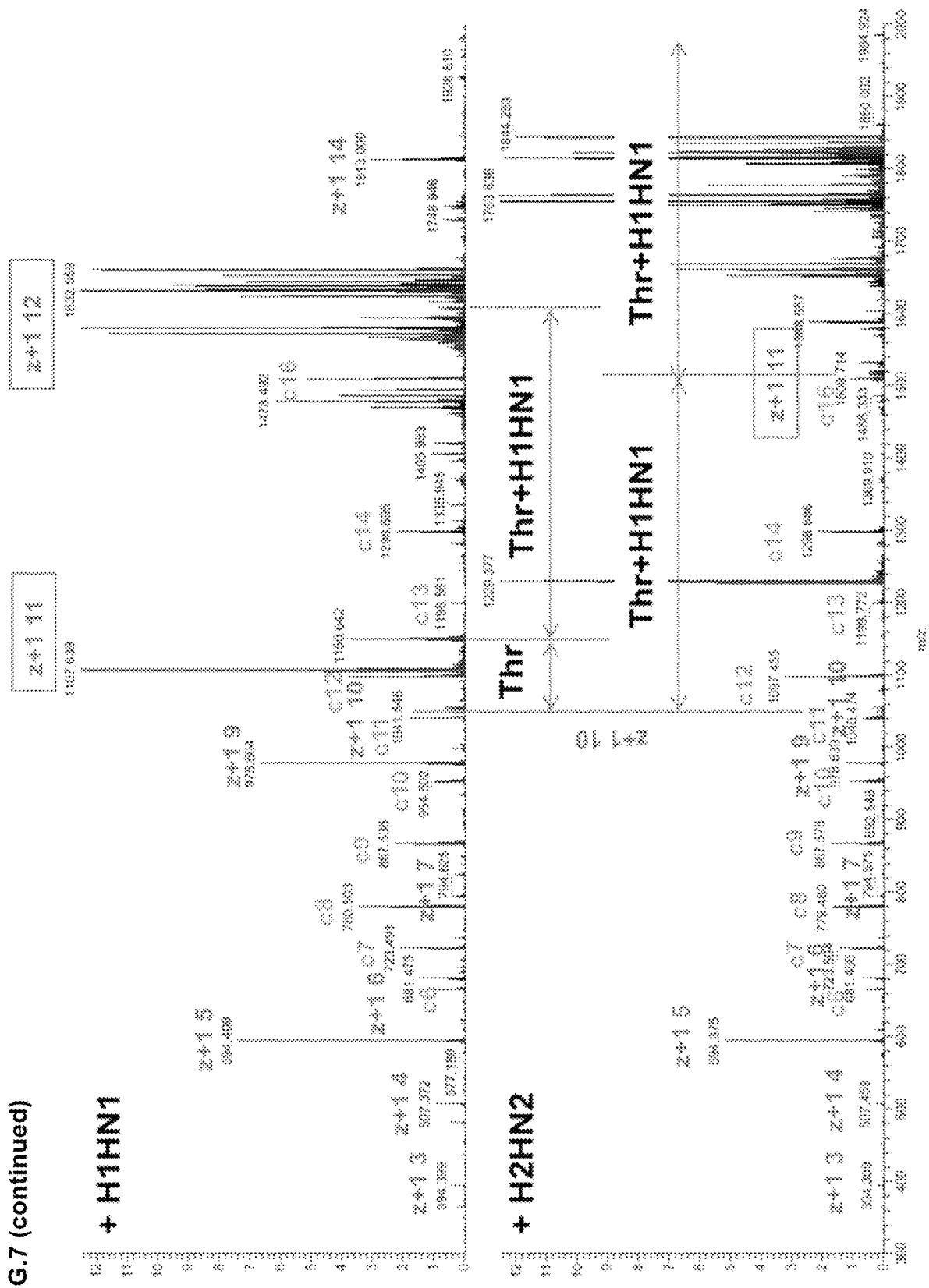

FIG. 8 relates to the sequences of HBsAgs-identified using a mass spectrometer by extracting HBsAgs present in the sera of HBV-infected individuals and treating with a peptidase, and the glycosylation sites and structures (glycan compositions). Shown are the results mapped against genotype C HBsAgs in the HBV database for the identified peptides.

The sequences that were analyzed and identified by the mass spectrometer for HBsAgs in this analysis are shown in FIG. 8.

[List of Antigens (S, M, L, PreS2, PreS2+O) (FIG. 9)]

The recombinant S-HBsAg, which is generated in yeast and is currently used as a vaccine, is not glycosylated. was expressed in Huh7 cells, which are hepatic cancer cells, and the antigen is N- and O-glycosylated. Further, an O-glycan and a binding peptide thereof, which are Jacalin recognition sites on HBV, were prepared and used as antigens (FIG. 9).

A schematic diagram of the vaccine candidates (antigens) used in the present development is shown in FIG. 9. The conventional vaccine antigen (S (−Gly)) is an unglycosylated S-HBsAg (black), which is expressed in yeast and prepared. The M-HBsAg (PreS2 (gray)+S) expressed and prepared in Huh7 cells is glycosylated (M (+Gly)). The L-HBsAg (PreS1 (white)+PreS2+S) generated using a *S. cerevisiae* strain is N-glycosylated (L (+Gly)). PreS2 peptides were chemically synthesized. An O-glycosylated PreS2 peptide was generated by chemical synthesis followed by glycan modification by a glycosyltransferase (PreS2+O).

The PreS2 sequence used in the present development is from genotype C and has an addition of a cysteine residue at the N' terminus of a peptide from V17 to R48. Further, as antibody-inducing peptides (antigen candidates), PreS2 and PreS1 of genotypes A to D were also synthesized.

Table 4 shows a list of the synthetic peptides (PreS1, PreS2).

TABLE 4

List of Synthetic Peptides (PreS1, PreS2)

| Name (Peptide) | Genotype | Sequence | Modification |
|---|---|---|---|
| PreS2 | C | C-VRGLYFPAGGSSSGTVNPVPTTASPISSIFSR (SEQ ID NO: 31) | — |
| PreS2 + O | C | C-VRGLYFPAGGSSSGTVNPVPTTASPISSIFSR (SEQ ID NO: 31) | GalNAc-Gal-SA |
| A-PreS2 | A | C-VRGLYFPAGGSSSGTVNPAPNIASHISSISAR (SEQ ID NO: 32) | |
| C-PreS2 + 2GalNAc | C (JPNAT) | C-VRGLYLPAGGSSSGTVNPVPTTASPISSIFSR (SEQ ID NO: 15) | GalNAc x2 |
| C-PreS2 + GalNAc | C (JPNAT) | C-VRGLYLPAGGSSSGTVNPVPTTASPISSIFSR (SEQ ID NO: 15) | GalNAc |
| D-PreS2 + GalNAc | D | C-VRGLYLPAGGSSSGTVNPVPTTVSHISSIFSR (SEQ ID NO: 33) | GalNAc |
| B-PreS2 | B | C-VRALYFPAGGSSSGTVSPAQNTVSAISSILSK (SEQ ID NO: 34) | |
| C-PreS1 | C | C-PDHQLDPAFGANSNNPDWDFNPNKDHWPEANQVG (SEQ ID No: 35) | |
| A-PreS1 | A | C-PDHQLDPAFGANSNNPDWDFNPIKDHWPAANQVG (SEQ ID NO: 36) | |
| D-PreS1 | D | C-PDHQLDPAFRANTANPDWDFNPNKDTWPDANKVG (SEQ ID NO: 37) | |
| B-PreS1 | B | C-PDHQLDPAFKANSENPDWDLNPHKDNWPDAHKVG (SEQ ID NO: 38) | |

However, in our study, glycans are present in the HBsAgs on HBV, which indicates the possibility of concentrating HBV particles with Jacalin. Next, in order to induce or generate antibodies that recognize infectious HBV particles, it is necessary to synthesize large amounts of HBsAg proteins close to the native HBV. A glycosylated HBsAg peptide was generated based on the results of mass spectrometry. We successfully prepared an N-glycosylated L-HBsAg (Glyco-L) using a *Saccharomyces cerevisiae* strain. The M-HBsAg Methods for synthesizing the above genotype C PreS2 peptides and glycopeptides are shown. A solid phase carrier (H-Arg(Pbf)-HMPB-ChemMatrix) was used to synthesize the peptides by solid phase synthesis with the Fmoc method. A swollen solid phase carrier treated with a solution of relevant Fmoc amino acid (5 equivalents) or Fmoc glycoamino acid (1.5 equivalents), a condensing agent COMU (1 equivalent relative to the Fmoc amino acid or Fmoc glycoamino acid), and a base DIEA (2 equivalents relative to the Fmoc amino acid or Fmoc glycoamino acid) was stirred in 0.8 ml of DMF (0.5 ml for glycoamino acid condensation reaction) for 30 minutes (3 hours in the case of glycoamino acid) at room temperature, and then washed with DMF. An acetyl-capping reaction was then carried out using 13 mM HOBt/(Ac$_2$O/DIEA/DMF) (4.75/2.25/93.0 v/v/v) for 2 minutes at room temperature and washed with DMF. Subsequently, a 20% piperidine/DMF solution was added and stirred at room temperature for 5 minutes for deprotection of the Fmoc group, and then washed with DMF. This operation was repeated to extend the peptide chain sequentially. The obtained peptidyl resin was washed with methylene chloride, dried, and then to which a cleavage cocktail (TFA/H$_2$O/EDT/TIS=94/2.5/2.5/1) was added and stirred at room temperature for 2 hours for cleavage from the carrier and deprotection of the side chain. After the filtrate was collected, ice-cold ether was added to obtain a crude peptide as a precipitate. The compound obtained by purification with HPLC was dissolved in methanol, to which 1 N NaOH was added to deprotect the acetyl group of the carbohydrate moiety. After neutralizing and concentrating the reaction mixture, it was purified again by HPLC to obtain target products (FIG. 10).

COMU:
(1-cyano-2-ethoxy-2-oxoethylidenaminooxy)dimethyl-amino-morpholino-carbenium hexafluorophosphate
HOBt: 1-hydroxybenzotriazole
DIEA: N,N-diisopropylethylamine
DMF: N,N-dimethylformamide
TFA: Trifluoroacetic acid
EDT: 1,2-ethanedithiol
TIS: Triisopropylsilane

[Chemical Synthesis of Glyco-PreS2 (FIG. 10)]

FIG. 10 shows the chemical formulae of PreS2 (PreS2 (Cys+V17-R48 (SEQ ID NO: 31)), upper panel and PreS2+O (PreS2 (Cys+V17-R48, T37+GalNAc), lower panel) shown in Table 4).

Figure 11:
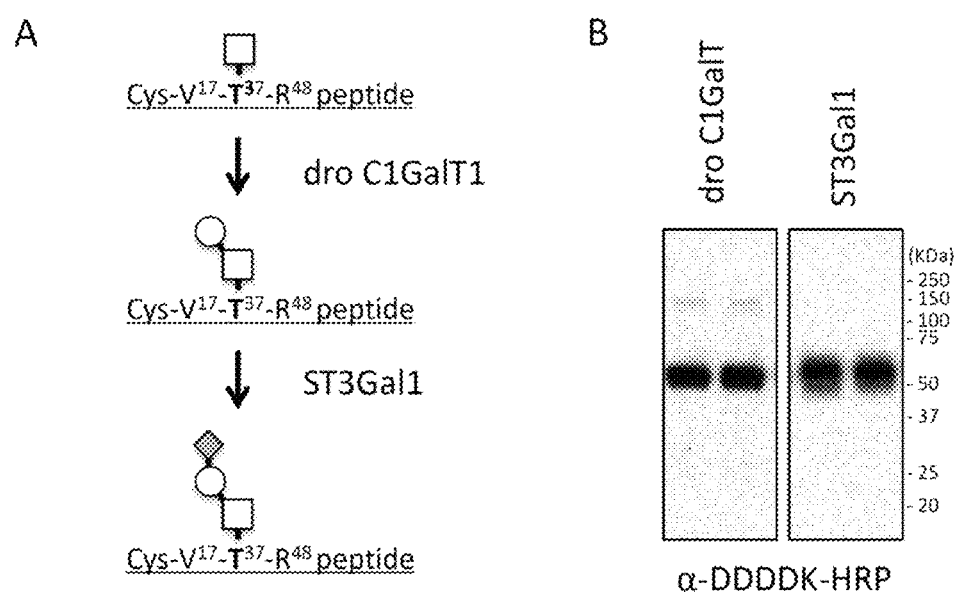
Figure 11:
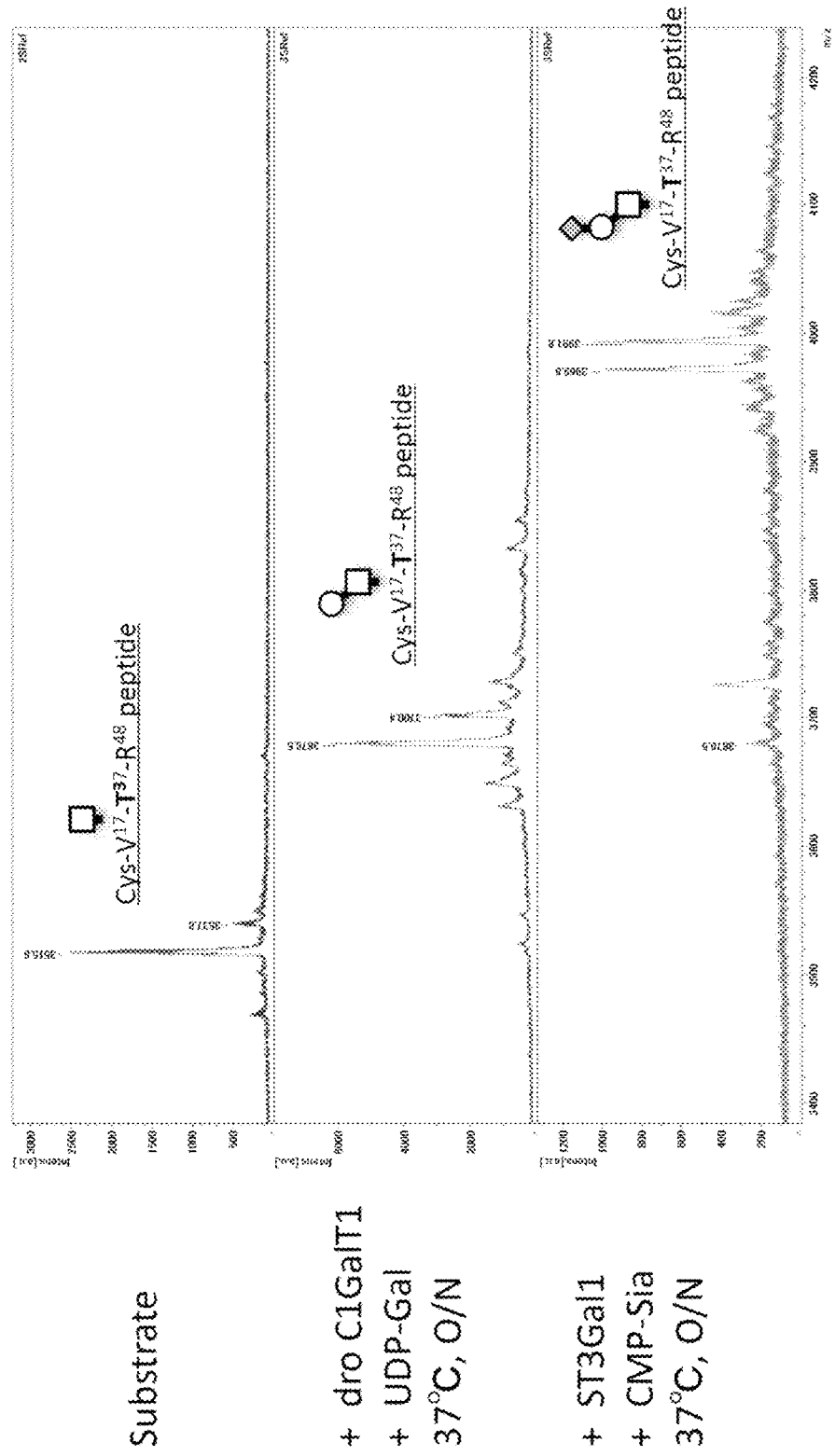

For the preparation of the Glyco-PreS2 glycopeptide, PreS2 (Cys+V17-R48, T37+GalNAc) was synthesized, and glycan elongation was carried out using a glycosyltransferase. The glycosyltransferases (*Drosophila*-derived Gal transferase [dro C1GalT1] and sialic acid [Sia] transferase [ST3Gal1]) used for the elongation reaction were produced using HEK293T cells. Enzyme proteins were purified from the culture supernatants of HEK293T cells transfected with the respective glycosyltransferase expression vectors using an anti-DDDDK-tag antibody (MBL, #M185-7, clone: FLA-1). After a portion of the purified protein was separated by SDS-PAGE, Western blot analysis was performed using an HRP-labeled anti-DDDDK-tag antibody (MBL). The detected bands were confirmed to be capable of producing the enzymes (dro C1GalT1 and ST3Gal1) at the expected molecular weights. The addition of Gal on T37+GalNAc was performed using dro C1GalT1 and a substrate (UDP-Gal), and further Sia was added using ST3Gal1 and a substrate (CMP-Sia) as described below. The addition reaction of Gal onto T37+GalNAc was carried out using the dro C1GalT enzyme and UDP-Gal (YAMASA CORPORATION, YM7213) as a donor substrate in a reaction solution containing 25 mM HEPES (pH 7.0), 10 mM MnCl$_2$, UDP-Gal, T37+GalNAc peptide, dro C1GalT at 37° C. overnight. After the reaction, a portion of the reaction solution was analyzed by MALDI-TOF-MS (Ultrafrex, BRUKER), and the addition reaction was confirmed to have proceeded to 100%. Subsequently, a ST3Sial enzyme and CMP-NeuAc (YAMASA CORPORATION, YM7215) were added to the reaction solution, and allowed to further react overnight at 37° C. The final product was separated and purified using COSMOSIL 5C18-AR-II Packed Column (Nacalai Tesque Inc., 38145), and the mass was confirmed with MALDI-TOF-MS (FIG. 11).

[Glycan Modification of Glyco-PreS2 (FIG. 11)]

A) A scheme of the glycan elongation reaction is shown. The addition of Gal was carried out using dro C1GalT1 and the addition of Sia was carried out using ST3Gal1 with a GalNAc-PreS2 peptide as a substrate. Squares represent GalNAc, circles represent Gal, and diamonds represent Sia. B) The glycosyltransferase used for the elongation reaction was produced using HEK293T cells. The enzyme proteins were purified from the culture supernatants of HEK293T cells transfected with the respective glycosyltransferase expression vectors using an anti-DDDDK-tag antibody (anti-FLAG tag antibody). After a portion of the purified protein was separated by SDS-PAGE, it was confirmed by Western blotting using an anti-DDDDK-tag antibody that the enzymes could be produced at the expected molecular weights. C) Confirmation of reaction products by a mass spectrometer. The products of the enzymatic reaction were purified by HPLC and were then each measured for its mass with a mass spectrometer.

Mass spectrometry results suggested that multiple N-glycans are attached to patient-derived L-HBsAgs. Accordingly, a glycosylated L-HBsAg (L (+Gly)) was expressed in a *S. cerevisiae* strain and prepared as a vaccine candidate.

Information on the amino acid sequence encoding HBsAg of genotype C (C_JPNAT) is shown in SEQ ID NO: 14. Based on this amino acid sequence information, gene sequences were designed to use codons that are frequently used in *S. cerevisiae* and total synthesis of the gene sequences was carried out. The signal sequence used was a pre-pro sequence of *S. cerevisiae* α-factor, and a gene sequence in which the signal sequence was immediately followed by the L-region (preS1+preS2+S regions) of HBsAg is designated as SEQ ID NO: 64. Gene synthesis was outsourced.

The obtained synthetic genes were cleaved with EcoRI and SalI, and a YEp352GAPII vector was cleaved with commercially available EcoRI and SalI, then each was subjected to agarose gel electrophoresis, and the bands corresponding to the respective fragments were excised from the gel. DNA fragments were extracted and purified from the excised gel pieces using Wizard SV DNA and PCR Clean-Up System from Promega Corporation. After DNA concentrations were measured with NanoDrop Lite (Thermo Fisher Scientific), the respective fragments at 50 ng each were mixed and made up with H$_2$O to 7.5 µL, to which 3.75 µL of Ligation High Ver. 2 (TOYOBO) were added, and reaction was carried out at 16° C. for 30 minutes. Using 2 µL of which, an *E. coli* strain, Competent *E. coli* DH5α, was transformed. Culturing was carried out on a LB agar medium containing 50 µg/mL ampicillin at 37° C. for 16 hours to obtain transformants.

The resulting colonies were cultured in a LB liquid medium containing 50 µg/mL ampicillin at 37° C. for 16 hours. The YEpHBVC2 vector (FIG. 12) was purified from the bacterial cells using Wizard Plus SV Minipreps DNA Purification System from Promega Corporation. Sequence analysis was performed to confirm that there was no mistake in the nucleotide sequence.

This vector (YEpHBVC2) was used to transform a *Saccharomyces cerevisiae* W303-1B strain (MATα ura3-52 trp1Δ2 leu2-3_112 his3-11 ade2-1 can1-100) according to conventional methods.

The transformed bacterial suspension was applied to a casamino acid-Ura agar medium (0.67% yeast nitrogen base w/o amino acid, 1% casamino acid, 2% glucose, 40 µg/ml tryptophan, 40 µg/ml adenine ½ sulfate, 2% agar) and cultured at 30° C. for 2 days to obtain transformant colonies. The colonies were scraped from the plates, chromosomal integration was confirmed by simplified PCR by suspension in a PCR reaction solution, and this yeast was set as an HBV L-HBsAg (Glyco-L)-expressing S. cerevisiae strain.

The Glyco-L-expressing yeast was pre-cultured and then inoculated in 1 L of 1× casamino acid-Ura medium (0.67% yeast nitrogen base w/o amino acid, 1% casamino acid, 2% glucose, 40 µg/ml tryptophan, 40 µg/ml adenine ½ sulfate) and cultured at 120 rpm at 30° C. for 120 hours. After the bacterial cells were isolated by centrifugation, a portion of the supernatant was subjected to SDS-PAGE and transferred to a PVDF membrane, followed by confirmation of expression by Western blot analysis. A commercially available anti-HBsAg antibody (anti-PreS1 monoclonal antibody (mouse); Institute of Immunology Co., Ltd., or Hepatitis B surface Antigen A, Goat Antibody; PROSPEC) was used as the primary antibody, and an anti-mouse IgG antibody-peroxidase or an anti-goat Ig antibody-peroxidase was used as the secondary antibody. Detection was performed using ECL Western Blotting Detection Reagents (GE) with an image analyzer (GE LAS-1000).

Purification was then performed. The cultured bacterial cells were suspended at 1 g in 5 ml of Y-PER™ Plus Dialyzable Yeast Protein Extraction Reagent (Thermo Fisher Scientific) containing 7.5 M urea and 0.1 M DTT, and extracted at room temperature for 20 minutes. After this extraction, residues were removed by centrifugation at 2000×g at 4° C. for 5 minutes, centrifugation was further carried out at 12,000×g at 4° C. for 5 minutes, and the obtained precipitate was collected. This precipitate was dissolved in 3 mL of a 0.1 M phosphate buffer (pH 7.2) containing 7.5 M Urea, 15 mM EDTA to serve as a crude extract of Glyco-L.

Then, a 4.55 mL density gradient with 10-40% potassium bromide (KBr) was set, 0.45 mL of the crude extract was added to the top layer, and ultracentrifugation was performed on a Beckman SW 55 T1 rotor at 73,000×g at 4° C. for 16 hours. Solutions were collected from the upper layers of the tubes in 0.3 ml increments, and Western blot analysis using an anti-PreS1 antibody was performed for each fraction. Fractions positively reacted to the antibody were collected, except for fractions with relatively high contaminating proteins (light KBr density). This solution was PEG-precipitated, and this precipitate was dissolved in a 0.1 M phosphate buffer (pH 7.2) containing 7.5 M urea, 15 mM EDTA and subjected to subsequent ultracentrifugation.

For the next step, a 4.8 mL 5-50% sucrose density gradient was set, 0.48 mL of the sample was added to the top layer, and ultracentrifugation was carried out under the same conditions as described above. Solutions were collected in 0.3-ml increments from the upper layers of the tubes, and each fraction was subjected to SDS-PAGE, followed by Oriole stain (Bio-Rad) and Western blot analysis using an anti-PreS1 antibody. Fractions positively reacted to the antibody were collected, dialyzed against distilled water, and then subjected to lyophilization.

The lyophilized samples (Glyco-L), after PBS addition, were sonicated and thawed for observation under an electron microscope. Simple purification was performed using a 30K Amicon Ultra 0.5 mL Centrifugal Filter (Millipore). The sample at a concentration of 0.1 mg/mL was observed and photographed at 25,000×, 50,000×, and 100,000× magnification on a grid for electron microsopic observation with the sample mounted thereon.

Figure 14:
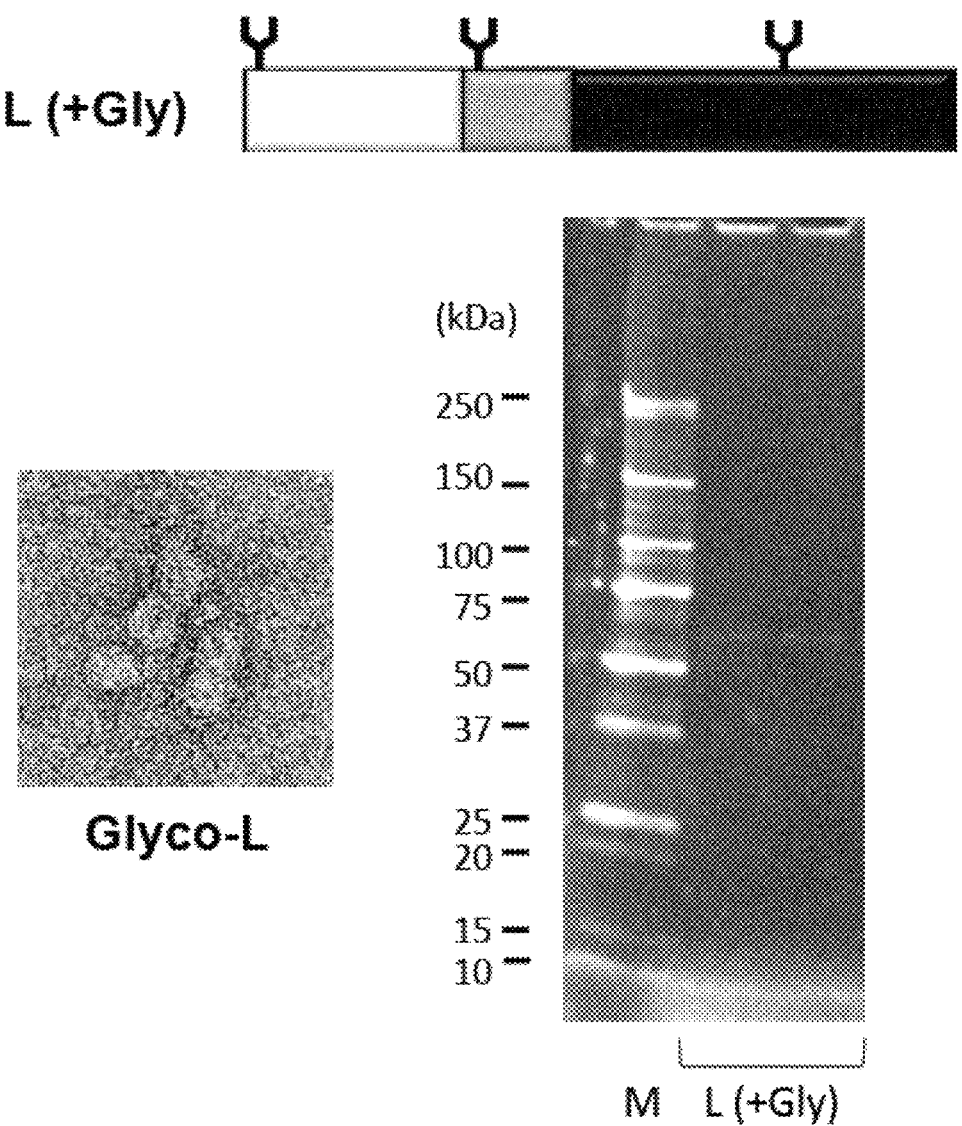

In order to express full-length HBsAgs from genotype_C in S. cerevisiae, an expression vector (YEpHBVC2) was constructed (FIG. 12) by codon optimization, full synthesis, and cloning. The S. cerevisiae strain W303-1B was transformed with YEpHBVC2 and clones expressing L (+Gly) were screened. When some of the cultures were subjected to Western blot analysis to verify expression, signals were confirmed both in the bacterial cells and in the culture medium. Since the molecular weight of Glyco-L whose expression was confirmed in the culture supernatant was about 60 kDa and was considerably larger than the expected molecular weight of about 45 kDa, glycan cleavage by Endo-Hf was performed to confirm the presence or absence of glycosylation. The results showed that the molecular weight of Glyco-L after Endo-Hf treatment was about 50 kDa, suggesting that at least one N-glycan was added. Moreover, since this Glyco-L expressed in the culture supernatant was also detected by the anti-pre-S1 antibody, it was confirmed that this Glyco-L was expressed in a form containing the N-terminus of the L region. After transformation and culturing for 120 hours, the bacteria were collected, lysed in the presence of 7.5 M urea, and subjected to density gradient centrifugation in potassium bromide and sucrose. Fractions that were dialyzed and purified were set as Glyco-L (FIG. 13). Observation by electron-microscopy was made to confirm the structure of Glyco-L. It was confirmed that an unglycosylated L-HBsAg likewise formed particles. Further, after the purified Glyco-L was subjected to SDS-PAGE on a 5-20% gradient gel, Oriole fluorescent gel staining was performed, confirming a single band (FIG. 14).

[Generation of a Vector for Glyco-L Expression in Yeast (FIG. 12)]

Figure 12:
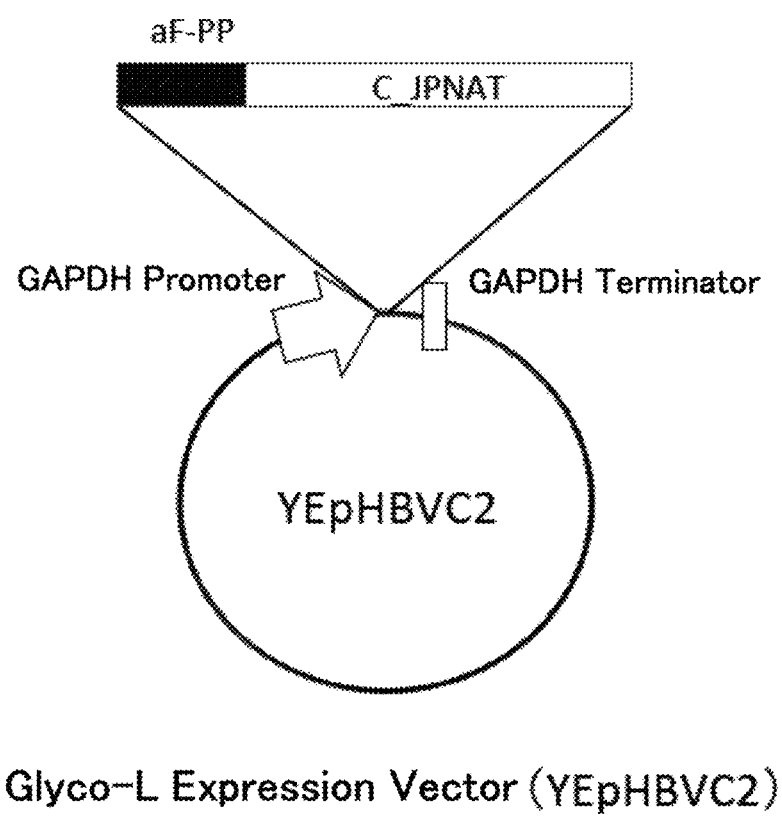

FIG. 12 shows a synthetic gene encoding C_JPNAT: HBV Genotype_C, in which GAPDH refers to a S. cerevisiae glyceraldehyde-3-phosphate dehydrogenase and aF-PP refers to a gene encoding the pre-pro sequence of S. cerevisiae α-factor.

[Generation Method/Purification Method (Yeast) of Glyco-L (FIG. 13)]

The S. cerevisiae strain W303-1B was transformed with YEpHBVC2 and clones expressing L (+Gly) were screened. After 120 hours of culturing, bacteria were collected, lysed in the presence of 7.5 M urea, and subjected to density gradient centrifugation with potassium bromide and sucrose. Fractions that were dialyzed and purified were set as Glyco-L. FIG. 13 shows protocols on the culture method, host, and purification method.

[Putative Structure of Glyco-L expressed in Yeast (FIG. 14)]

L (+Gly) was expressed in yeast and purified. It was confirmed with an electron microscope that the prepared fraction (Glyco-L) formed particles (FIG. 14, lower left panel). After Glyco-L was subjected to SDS-PAGE on a 5-20% gradient gel, Oriole fluorescent gel staining was performed (FIG. 14, lower right panel).

Observation of Glyco-L: L (Gly) with an electron microscope revealed particle formation. Further, when L (+Gly) was separated with SDS-PAGE to confirm the molecular weight, it was also confirmed that L (+Gly) was about 65 kDa, larger than unglycosylated L-HBsAg (Beacle), and that an N-glycan was attached to L (+Gly) by enzymatic treatment (M: molecular weight marker, G-L: purified Glyco-L).

[Generation of Anti-HBs Antibody]
(Immunization of mice with HBs protein)

Mice (Balb/c mice, 8-week-old females) were immunized with a commercially available recombinant HBs-protein (S-HBs: bimmugen) or the glycosylated recombinant HBs proteins we generated (Glyco-L and Glyco-M). For various peptide antigens, those conjugated with keyhole limpet hemocyanin (KLH) were used. A 0.2 mg portion of each antigen peptide was bound (conjugated) to KLH using Thermo Fisher's Imject Maleimide Activated mcKLH Spin Kit (#77666). These various HBs proteins (KLH-conjugated peptides) dissolved in saline were mixed with complete Freund's adjuvant (PIERCE, Imject Alum Adjuvant also usable), and immunization was carried out by intraperitoneal injection at a dose of 1 µg on the first day (Day 0), 0.5 µg on Day 4, and 0.5 µg on Day 10. Mice were subjected to regular orbital blood sampling and immunization was performed while monitoring for increases in antibody titers to the antigen in serum. In addition, because of the expected increase in antibody titers, boosting was performed by administering (about 0.1-1 µg) an immunogen (glycopeptide or glycoprotein) to the tail vein 2-7 days before serum and immune B cell collection.

Antibody-producing cells were collected from the immunized mice that were confirmed to have sufficiently increased antibody titers. Collection was made 3 days later, because it was more preferable to collect 2-5 days after the date of the last immunization. Antibody-producing cells include splenocytes, lymph node cells, peripheral blood cells, etc., but splenocytes or local lymph node cells are preferred. Methods for collecting antibody-producing cells from mice may be performed according to techniques known in the relevant field. Specifically, antibody-producing hybridoma cells can usually be obtained by collecting splenocytes and performing a fusion operation, which will be further described below. It is also possible to obtain a recombinant antibody protein by the method described below.

[Antibody-Antibody ELISA Measurement System Using Anti-HBs Antibody Obtained in the Present Invention]
(Detection of Total HBs Molecules by an Antibody-Antibody ELISA Measurement System)

Detection was performed by an ELISA measurement system for reactivity (binding) to the various HBsAgs, using antisera (containing antibodies against the antigen) against the various HBsAgs obtained from mice immunized as described above. The various HBsAgs were each immobilized to ELISA plates, and examination with the ELISA measurement system was performed using antisera or commercially available anti-HBs antibodies on the side of detection.

First, each HBsAg (commercially available recombinant HBs proteins (yeast-derived S-HBs: MyBioSource; yeast-derived L-HBs: Beacle; *E. coli*-derived PreS1 peptide: Beacle; *E. coli*-derived PreS2 peptide: Beacle) or the recombinant HBs protein we generated (glycosylated PreS1 peptide, PreS2 peptide, and L-HBs or M-HBs)) was diluted with PBS to 0.5 µg/mL, added to an ELISA microplate (ThermoFisher Immobilizer Amino) at 100 µL/well, and covalently bound via an amino group. After each antibody was allowed to adsorb (immobilize) to the plate at 4° C. overnight, the solutions were discarded, and the wells were washed with PBS-T (PBS, 0.05% Tween-20). Next, the solutions of a serial dilution of the antisera were added to each well at 100 µL. After reacting for 2 hours at 37° C., the solutions in the wells were discarded, the wells were washed with PBS-T, and then allowed to react for 1 hour at room temperature with a 4000-fold diluted horseradish peroxidase (HRP)-labeled anti-mouse IgG antibody (Jackson, 115-035-062). Thereafter, the reaction solution was discarded, washing was performed, and then color development by a 1StepUltra TMB substrate solution (Pierce) was measured at an absorbance of 450 nm (FIG. 15).

Balb/c mice were immunized with the glycosylated PreS2 peptides and L-HBs or M-HBs listed in Table 4, and the reactivity to the various antigens (L-HBs, M-HBs, S-HBs, PreS1 peptide, PreS2 peptide) was comparatively analyzed with an anti-S-HBs antibody, which resulted in the acquisition of mouse sera with different antigen reactivities.

The reactivity to L-HBsAg was examined in antisera obtained by immunizing mice with an L-HBsAg (yeast-derived glycosylated L-HBs made by AIST), an S-HBsAg (Bimmugen), or PBS only (without an immunizing antigen) as the immunizing antigen.

[Comparison of Changes in Antibody Titers (Glyco-L and S-HBs Bimmugen) (FIG. 15)]

FIG. 15 shows the ELISA results (A) against L-HBs using sera over time (Day 0, 21, 28, 35) from mice (YL-1 to YL-4) immunized with the glycosylated L-HBsAg (Glyco-L), mice (B1 and B2) immunized with the S-HBsAg (Bimmugen), and control mice (N1+N2), and a commercially available anti-PreS1 antibody (BCL-002). FIG. 15 also shows the ELISA results (B) obtained in a similar manner by diluting the Day 35 sera (1/1000, 1/3000, 1/9000, 1/27000).

As shown in FIG. 15(A), antibody titers were confirmed to be increased in mice (YL) immunized with the L-HBsAg (Glyco-L) from an earlier stage (as of Day 21, fewer days post-immunization) compared with mice immunized with the S-HBsAg (Bimmugen) (B). Meanwhile, for immunization with the S-HBsAg, the antibody titer remained low until Day 28 and was confirmed to increase on Day 35. In addition, as a result of diluting and subjecting the obtained Day 35 sera to ELISA to examine antibody titers, it was confirmed that the reactivity of many L-HBs antisera decreased at a 1/27000 dilution rate. However, it was found that the reactivity of the S-HBs antisera already decreased remarkably at 1/9000 dilution (FIG. 15(B)). These results are believed to indicate the possibility that the L-HBsAgis superior as an immunogen and a wide range of antibodies can be acquired in a small number of doses based on an improvement of the immunization method because of the differences in antibody titers and antibody populations that increase due to immunization with the L-HBsAg and S-HBsAg.

These results indicate that the Glyco-L-HBsAg is more immunogenic than the S-HBsAg, but the differences in reactivity to sites other than those used as antigens are unknown. Accordingly, we compared the cross-reactivity of antisera obtained by immunization with the Glyco-L-HBsAg (Glyco-L-HBs antisera) and commercially available antibodies against each antigen by ELISA and Western blot analysis. The reactivity for an unglycosylated L-HBsAg was almost equal between the antisera from immunization with the unglycosylated L-HBsAg and the antisera from immunization with the glycosylated L-HBsAg (Glyco-L-HBs). Meanwhile, the reactivity for the glycosylated L-HBsAg (Glyco-L-HBs) was found to be decreased in the antisera from immunization with the unglycosylated L-HBsAg. This suggests that antisera (antibodies) obtained by immunization with an unglycosylated antigen differ in their recognition (reactivity) for glycosylated antigens. Moreover, the Glyco-L-HBs antisera were shown to be more reactive to PreS1 and PreS2 regions than to the S region and like FIG. 15, the high immunogenicity of the L-HBsAg is believed to be attributed to the PreS1 and Pre-S regions.

Figure 16:
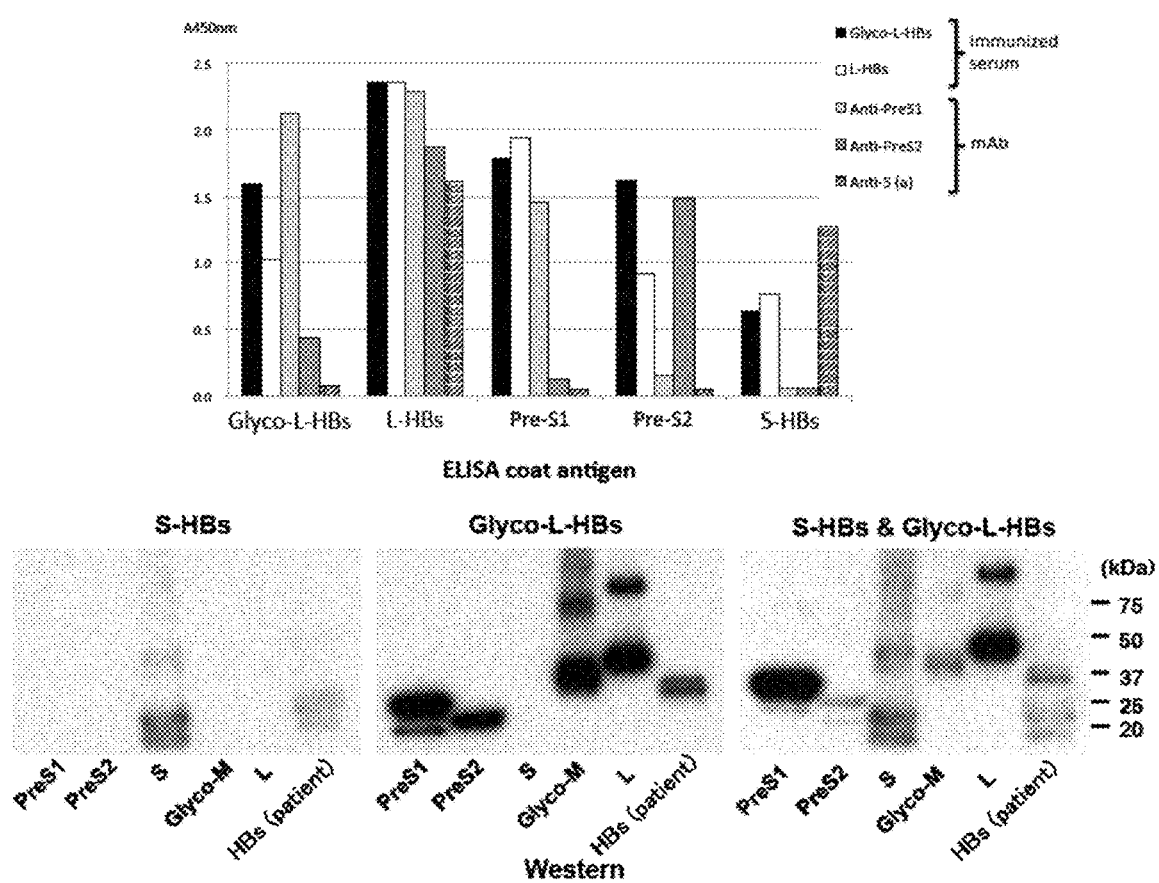

Mouse antisera obtained from mice immunized with the various HBsAgs (Glyco-L-HBs antiserum, L-HBs antiserum) or commercially available anti-HBs antibodies from hybridomas obtained as previously described (anti PreS1 antibody: Beacle BCL-AB-002; anti-PreS2 antibody: Institute of Immunology Hyb-5520; anti-S antibody: Institute of Immunology Hyb-824) were used to carry out ELISA measurements in the same manner as described above with plates coated with each HBsAg(glycosylated L-HBsAg: Glyco-L-HBs, unglycosylated L-HBsAg, PreS1 peptide, PreS2 peptide, S-HBsAg Bimmugen). Western blotting of the molecule was performed according to a general method. First, the PreS1 peptide (produced in $E.\ coli$), PreS2 peptide (produced in $E.\ coli$), (produced in yeast), Glyco-M-HBsAg (produced in HEK293), L-HBsAg (produced in yeast), and HBsAg (patient serum) were electrophoresed using 12.5% SDS-PAGE gel under reducing conditions and transferred onto PVDF membranes. After blocking with PBS containing 5% skim milk, the membranes were allowed to react with sera after HBsAg immunization (antiserum from immunization with the S-HBsAg, antiserum from immunization with the Glyco-L-HBsAg, and antiserum from simultaneous immunization with the S-HBsAg and the Glyco-L-HBsAg) for 1 hour at room temperature. After the PVDF membranes were washed, they were allowed to react with a secondary antibody (0.5 µg/mL of an HRP-labeled anti-mouse IgG antibody) for 1 hour at room temperature. These PVDF membranes were washed and then detected by chemiluminescence with Western blotting detection reagents (Perkin Elmer) (FIG. 16). The ELISA results indicate that the Glyco-L-HBs antiserum contained more antibodies against the PreS1 and PreS2 regions than the S region, and similar results were also confirmed by Western blotting. However, when immunization was performed with the S-HBsAg, only antibodies against the S-region were induced. When Western blotting was performed using the antiserum obtained by simultaneous immunization with the Glyco-L-HBsAg and the S-HBsAg, it could be confirmed from the results that an antibody population recognizing all of the S region, PreS1 region, and PreS2 region was induced (FIG. 16, lower panel).

[ELISA and Western Blot (Sera, L- & S-HBs Mix) (FIG. 16)]

The upper panel of FIG. 16 shows the results of the reactivity for each HBsAg (glycosylated L-HBsAg: Glyco-L-HBs, unglycosylated L-HBsAg, PreS1 peptide, PreS2 peptide, S-HBsAg: Bimmugen) using the obtained antisera (Glyco-L-HBs antiserum, L-HBs antiserum) and commercially available anti-HBs antibodies (anti-PreS1 antibody: Beacle BCL-AB-002; anti-PreS2 antibody: Institute of Immunology Hyb-5520; anti-S antibody: Institute of Immunology Hyb-824).

The lower panels of FIG. 16 show Western blotting performed using the antiserum from immunization with the S-HBsAg (left), the antiserum from immunization with the Glyco-L-HBsAg antigen (middle), and the antiserum from simultaneously immunization with the S-HBsAg and the Glyco-L-HBsAg(right). The figure shows the results obtained by separating a PreS1 peptide ($E.\ coli$), a PreS2 peptide ($E.\ coli$), an S-HBsAg (yeast), Glyco-M-HBsAg (HEK293), an L-HBsAg (yeast), and HBsAg (patient serum) by SDS-PAGE and comparing the reactivities of the respective antisera.

The antiserum after immunization with a conventional vaccine (S-HBsAg) recognizes the S-HBsAg but has a low reactivity for other HBsAg components. Meanwhile, the antiserum from immunization with the Glyco-L-HBsAg was excellent in the reactivity for components other than the S-HBsAg. The antiserum from simultaneous immunization with the S-HBsAg and the Glyco-L-HBsAg recognized all of the above main components, suggesting its efficacy as a vaccine for mixed immunization.

The above results suggest that the L-HBsAg induces more PreS1, PreS2 antibodies than antibodies of the S-HBsAg, and co-immunization of S- and L-HBsAgs results in the acquisition of broad-coverage antibodies at one time. This, in other words, suggests that the PreS1 and PreS2 regions have a higher antigenicity (immunogenicity) than the S region, revealing a higher efficacy than the main S region vaccine conventionally used. That is, although it is necessary to develop next-generation vaccines in preparation for the problems to be solved toward universal vaccination (such as the costs of three-dose vaccination, non-responders, and the appearance of escape mutants by glycosylation), it is possible to develop combinations or mixed vaccines of both L-HBsAg and S-HBsAg as an improvement of the vaccination method.

The reactivity for various HBsAgs (Glyco-PreS2 peptide, PreS2 peptide, PreS1 peptide, S-HBsAg) was examined using antisera (sera on Day 49 after immunization) obtained by immunizing mice with an O-glycosylated PreS2 peptide (KLH-conjugated Glyco-PreS2, Genotype C made by AIST) or an L-HBsAg(yeast-derived Glyco-L-HBs made by AIST) as the immunizing antigen.

Each HBsAg (Glyco-PreS2 peptide, PreS2 peptide (produced in $E.\ coli$), PreS1 peptide (produced in $E.\ coli$), S-HBsAg (adr, produced in yeast)) was diluted with PBS to 0.5 µg/m L, and added to ELISA microplates (ThermoFisher Immobilizer Amino) at 100 µL/well, and covalently bound via an amino group. After each antibody was adsorbed (immobilized) to the plates overnight at 4° C., the solutions were discarded, and the wells were washed with PBS-T (PBS, 0.05% Tween-20). Next, the solutions of a serial dilution of antisera (Glyco-PreS2 immunized F1 mice at Day 0 and at Day 49, Glyco-L-HBs immunized YL3 mice at Day 35) and antibodies (anti-PreS1 antibody (Anti-PreS1), anti-PreS2 antibody (Anti-PreS2), and anti-S antibody (Anti-S(a)) were added at 100 µL to each well. After reacting for 2 hours at 37° C., the solutions in the wells were discarded, the wells were washed with PBS-T, and then allowed to react for 1 hour at room temperature with a 4000-fold diluted horseradish peroxidase (HRP)-labeled anti-mouse IgG antibody (Jackson, 115-035-062). Thereafter, the reaction solution was discarded, washing was performed, and then color development by a 1StepUltra TMB substrate solution (Pierce) was measured at an absorbance of 450 nm (FIG. 17).

[Comparison of Changes in Antibody Titers (Glyco-PreS2, ELISA) (FIG. 17)]

Antisera (F1 or YL3) obtained by immunization of mice with the Glyco-PreS2 peptide or the Glyco-L-HBsAg were analyzed by ELISA for reactivity to A) an O-glycosylated PreS2 peptide, B) a PreS2 peptide, C) a PreS1 peptide, and D) an S-HBsAg. Antibodies recognizing proteins used in ELISA plate immobilization were measured as controls.

Figure 17:
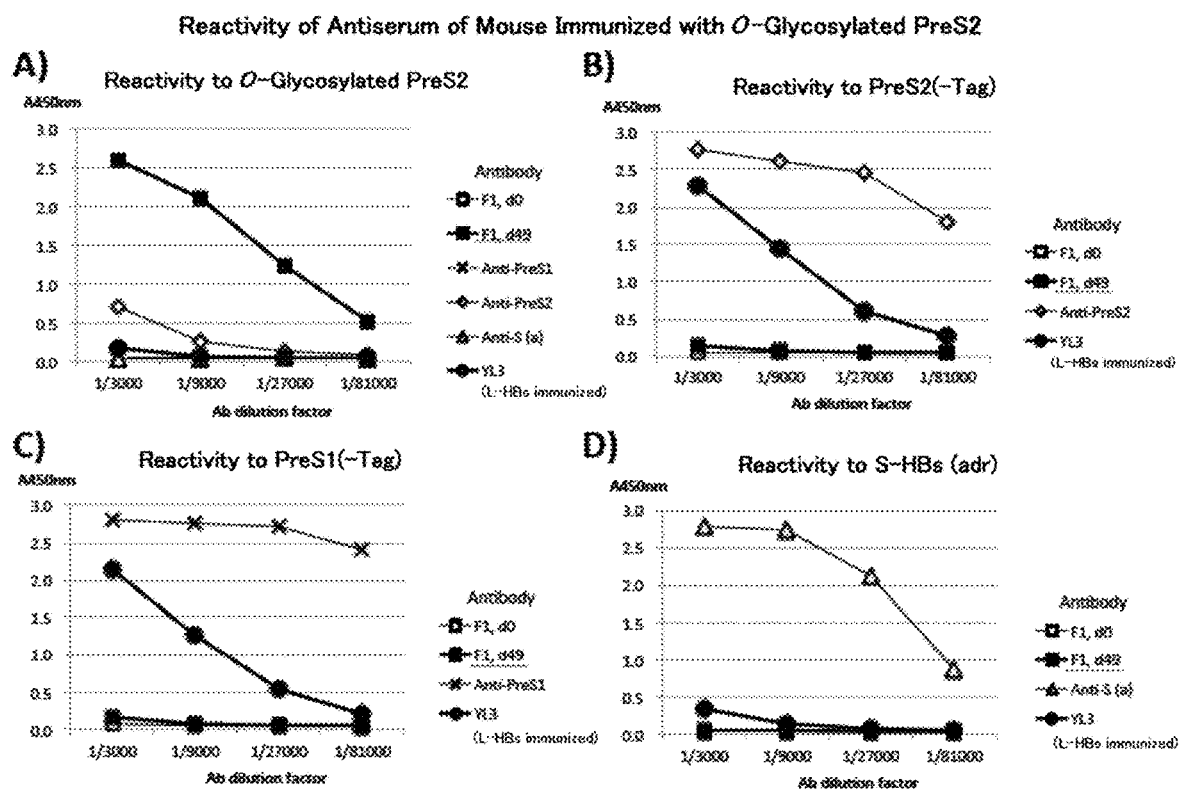

As shown in FIG. 17(A), a reactivity (increase in antibody titer) to the immunogen was confirmed in the mouse antiserum F1 (serial dilution) immunized with the Glyco-PreS2 peptide. However, in the same serum, no reactivity to antigens other than the immunogen (PreS2 peptide, PreS1 peptide, and S-HBsAg) was observed as shown in FIG. 17 (B) to (D). This confirmed a specific activity against the glycosylated PreS2 antigen.

In addition, although a reactivity to the PreS2 peptide and PreS1 peptide was observed in the L-HBs immune antiserum (YL3), little activity was observed for the S-region (S-HBsAg). This again suggests that the PreS2 region is more immunogenic than the PreS1 region as immunogens.

The reactivity for each HBsAg (O-glycosylated PreS2 peptide, PreS2 peptide, PreS1 peptide, S-HBsAg (adr, My BioSource) and unglycosylated L-HBsAg (Beacle) was compared using the obtained antiserum (Glyco-PreS2 antiserum) and commercially available anti-HBs monoclonal antibodies (anti-PreS1 antibody: Beacle anti-PreS1 mAb-2 Cat No. BCL-AB-002; anti-PreS2 antibody: Institute of Immunology Hyb-5520; anti-S-HBs antibody: Institute of Immunology Hyb-824) (FIG. 18 upper panel).

Western blotting with a PreS2 antiserum and a Glyco-PreS2 antiserum was performed to confirm the differences in antibodies induced by the difference in the presence or absence of glycans.

The reactivity for each HBsAg (O-glycosylated PreS2 peptide, PreS1 peptide (*E. coli*), PreS2 peptide (produced in *E. coli*), S-HBsAg (produced in yeast, adr, My BioSource)) and an unglycosylated L-HBsAg (yeast, Beacle) was compared by ELISA as described above, using the Glyco-PreS2 antiserum and commercially available anti-HBs monoclonal antibodies (anti-PreS1 antibody: Beacle anti-PreS1 mAb-2 Cat No. BCL-AB-002; anti-PreS2 antibody: Institute of Immunology Hyb-5520; anti-S-HBs antibody: Institute of Immunology Hyb-824). Western blotting was also performed in the same manner as in FIG. 16 described above. The PreS1 peptide (produced in *E. coli*), PreS2 peptide (produced in *E. coli*), S-HBsAg (produced in yeast), Glyco-M-HbsAg (produced in HEK293), L-HBsAg (produced in yeast), and HBsAg (patient serum) were electrophoresed using 12.5% polyacrylamide gel under SDS-PAGE reducing conditions and transferred onto PVDF membranes. After blocking with PBS containing 5% skim milk, the membranes were allowed to react with sera after HBsAg immunization (antiserum from immunization with the S-HBsAg, antiserum from immunization with the Glyco-L-HBsAg, and antiserum from simultaneous immunization with the S-HBsAg and the Glyco-L-HBsAg) for 1 hour at room temperature. After the PVDF membranes were washed, they were allowed to react with a secondary antibody (0.5 µg/mL of an HRP-labeled anti-mouse IgG antibody) for 1 hour at room temperature. These PVDF membranes were washed and then detected by chemiluminescence with Western blotting detection reagents (Perkin Elmer) (FIG. 18).

The Glyco-PreS2 antiserum showed a specific response only to the glycosylated Glyco-PreS2 peptide. Meanwhile, although a reactivity to the peptide of each region was observed in the commercially available anti-HBs antibodies (anti-PreS1 antibody, anti-PreS2 antibody), hardly any reaction was observed for the glycosylated, O-glycosylated PreS2 antigen.

Western blotting with the PreS2 antiserum and the Glyco-PreS2 antiserum was performed to confirm the differences in antibodies induced by the difference in the presence or absence of glycans. The PreS2 antiserum did not show any reaction to the glycosylated PreS2 antigen-containing Glyco-M and patient-derived HBsAg. Meanwhile, it was confirmed that the Glyco-PreS2 antiserum showed a low reactivity to PreS2 (including PreS2 for other genotypes) and L-HBs which do not contain these glycans, but reacted strongly to Glyco-M and patient-derived HBsAg. These results suggest that the presence or absence of glycosylation affects antigen recognition (reactivity) of the obtained antibodies (antisera).

[ELISA and Western Blot Analysis (Sera, Glyco-PreS2, PreS2) (FIG. 18)]

The upper panel of FIG. 18 shows the confirmation results by ELISA of the reactivity for each HBsAg (O-glycosylated PreS1, PreS1 peptide (*E. coli*), PreS2 peptide (*E. coli*), S-HBsAg (yeast), L-HBsAg (yeast)) using the obtained antisera (Glyco-L-HBs antiserum, L-HBs antiserum) and commercially available anti-HBs antibodies (anti-PreS1 antibody, anti-PreS2 antibody, anti-S antibody).

The lower panel of FIG. 18 shows the results of developing the PreS1 peptide (*E. coli*), PreS2 peptide (*E. coli*), S-HBsAg (yeast), Glyco-M-HBsAg (HEK293), L-HBsAg (yeast), and HBsAg (patient serum) by SDS-PAGE and Western blotting with a PreS2 antiserum (left) and a Glyco-PreS2 antiserum (right).

It was shown that the Glyco-PreS2 antiserum does not recognize the unglycosylated PreS2 peptide (*E. coli*) and recognize the Glyco-M-HBsAg (HEK293). Moreover, it became clear that there existed a Glyco-M-HBsAg-which is recognized more strongly by the Glyco-PreS2 antiserum than the PreS2 antiserum, in the HBsAg (patient serum).

Immunization was examined again, including a confirmation of the reproducibility. The reactivity to the immunizing antigen (O-glycosylated PreS2 peptide) was examined using antisera obtained by immunizing mice with the O-glycosylated PreS2 peptide as the immunizing antigen (sera on Day 43 after immunization).

The HBsAg (Glyco-PreS2 peptide) was diluted with PBS to 0.5 µg/mL, added to ELISA microplates (Thermo Fisher Scientific Immobilizer Amino) at 100 µL/well, and covalently bound via an amino group. After each antibody was adsorbed (immobilized) to the plates overnight at 4° C., the solutions were discarded, and the wells were washed with PBS-T (PBS, 0.05% Tween-20). Next, the solutions of a serial dilution of the Glyco-PreS2-immunized antisera (F1, F2, F3 mice on Day 0 and Day 49) were added at 100 µL to each well. After reacting for 2 hours at 37° C., the solutions in the wells were discarded, the wells were washed with PBS-T, and then allowed to react for 1 hour at room temperature with a 4000-fold diluted horseradish peroxidase (HRP)-labeled anti-mouse IgG antibody (Jackson, 115-035-062). Thereafter, the reaction solution was discarded, washing was performed, and then color development by a 1StepUltra TMB substrate (Pierce) was measured at an absorbance of 450 nm (FIG. 19).

Figure 19:
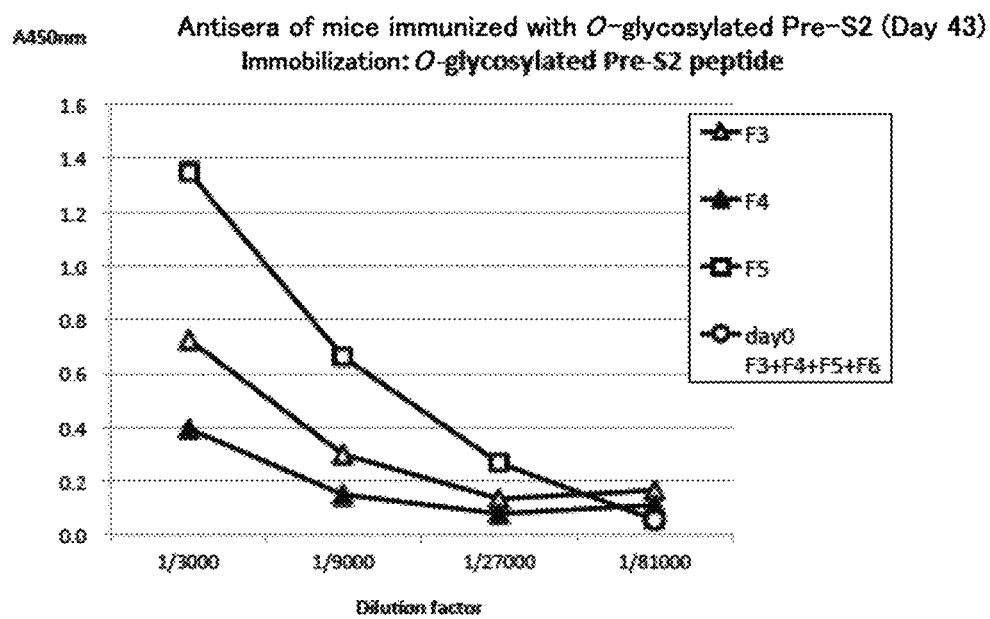

As shown in FIG. 19, a reactivity (increase in antibody titer) was confirmed for the immunogen O-glycosylated PreS2 peptide in the antisera (serial dilution) of mice immunized with the O-glycosylated PreS2 peptide.

[Differences in ELISA Depending on Immunized Mice (Sera, Glyco-PreS2) (FIG. 19)]

The reactivity for the O-glycosylated PreS2 peptide was analyzed by ELISA using sera (F3, F4, F5) on Day 43 after immunization with the O-glycosylated PreS2 peptide. Differences in antibody titers were observed in the antisera (F3, F4, F5) from immunization with the O-glycosylated PreS2 peptide, but all showed a reaction for the glycosylated, O-glycosylated PreS2 peptide. This suggests that antibodies (antisera) obtained by immunization with a glycosylated PreS2 antigen are reproducible, including antigen recognition (reactivity).

From the confirmation results by ELISA of increases in antibody titers in these mouse sera, it was confirmed that a serogroup recognizing almost the entire region of the HBsAgs was successfully acquired. The antigen recognition of the antibodies obtained by immunization with the various antigens is summarized in Table 5.

TABLE 5

Comparison of Acquired Sera and Antisera

| Immunogen | PreS1 | PrPS2 | S | S (patient) | M (patient) | L (patient) | Inhibition of HBV Infection |
|---|---|---|---|---|---|---|---|
| S | — | — | +++ | ++ | ± | ± | ○ |
| Glyco-L | +++ | +++ | ± | ± | ± | ++ | ○ |
| S + Gyeo-L | +++ | ++ | +++ | ++ | + | ++ | Not Tested |
| PreS2 | — | +++ | — | — | ± | ++ | Not Tested |
| Glyco-PreS2 | — | ± | — | — | +++ | ± | ○ |

Co-immunization with the Glyco-L-HBsAg and S-HBsAg enables the acquisition of antibodies that recognize a wide range of regions. Moreover, it was shown that antibodies specifically recognizing the M-HBsAg could be acquired with a PreS2 glycopeptide, and that antibodies recognizing all of the HBs components can be obtained by the above.

An HBV-infection inhibitory activity was confirmed in the antisera from immunization with the Glyco-L-HBsAg, S-HBsAg, or the PreS2 glycopeptide. In particular, since neutralizing antibodies that inhibit HBV infection were induced by the Glyco-L-HBsAg and PreS2 glycopeptide, it was found that the glycosylated antigens efficiently induce neutralizing antibodies which inhibit HBV infection compared with the conventional, unglycosylated antigen.

[Hybridoma Generation]

Antibody producing cells which produce anti-HBsAg antibodies can be obtained by various methods from the individual mice in which an increase in antibody titer was recognized.

By carrying out cell fusion of antibody-producing cells with myeloma cells, hybridomas that produce anti-HBsAg monoclonal antibodies can be generated. The cell fusion operation is performed with a cell fusion promoter (PEG1500) according to a conventional method (described below), by using immunized mouse-derived splenocytes and mouse myeloma cells (P3U1 cells), washing the respective cells with RPMI media, and then mixing the cells. The operation is preferably performed with the splenocytes and mouse myeloma cells (P3U1) at a mixing ratio of 8:1, but conditions also vary with the immunizing antigen, so it is better to carry out the operation at a ratio determined by the respective appropriate preliminary studies. After cell fusion, culturing is performed in a HAT medium as a selective medium (a medium in which, to RPMI1640 medium, 100 units/mL penicillin, 100 μg/mL streptomycin, and 10% fetal bovine serum (FBS), $10^{-4}$ M hypoxanthine, $1.5 \times 10^{-5}$ M thymidine, and $4 \times 10^{-7}$ M aminopterin were added), and selective culturing is performed so that only the fused cells survive. Cells growing in the selective medium after about 10 days following the start of culture are selected as hybridomas, and then monoclonal cells are obtained by limiting dilution. Specifically, a cell solution (concentration) is seeded in a 96-well culture plate in such a manner that a serial dilution is generated from high to low concentrations, a hybridoma cell group derived from a limited number of cells is selected, and (positive wells in the 96-well plate including) clones which produce antibodies to various HBsAg are selected by the screening described below.

[Screening Method]

The presence or absence of the target anti-HBsAg monoclonal antibody in the culture supernatant of the grown hybridomas was screened by enzyme-linked immunosorbent assay (ELISA). A portion of the culture supernatant contained in the wells in which the hybridomas were cultured is collected, and binding activity to the recombinant HBs protein used as the immunogen (and binding activity to an antigen other than the immunizing antigen as a negative control, or to an antigen that normally does not bind) is used as an indicator. Various HBsAg were immobilized (100 μL/well at 1 μg/mL) to 96-well plates, and after blocking, 100 μL of the culture supernatant was added and allowed to react for 1 hour at 37° C. Positive clones are selected by ELISA screening and limiting dilution (specifically, the 96-well culture plates are seeded at a concentration of about 0.3 cells per well). It is better to obtain wells that are positive at the time of primary screening and further develop them by limiting dilution to further narrow down the cells. From this secondary screening onwards, hybridoma cells that produce monoclonal antibodies against the target HBsAg can be obtained by repeated screening according to the circumstances and selecting hybridoma clones that are ultimately single anti-HBs monoclonal antibody-producing cells.

[Collection of Antibodies Produced from Hybridomas]

These hybridoma cell lines can be suitably cultured at 37° C. using a medium in which 10% FBS is added to RPMI1640. Antibodies are purified and obtained from the culture supernatant (about 100 mL to 1 L, appropriately selected depending on the required amount) of the obtained hybridoma cells.

The anti-HBsAg monoclonal antibodies can be collected by conventional techniques, and when purification of an antibody is necessary, purification can be performed using known methods such as ion exchange chromatography, affinity chromatography using Protein A, Protein G, etc., gel chromatography, and ammonium sulfate salting-out.

[Generation of Recombinant Anti-HBsAg Antibody: Acquisition of Antibody-Producing B Cells]

Hybridoma generation is a general method for obtaining antibodies, but there are several means in antibody obtaining methods. Here, a method for directly obtaining a gene of an antibody that exhibits binding to an antigen was used. To acquire antibody cDNA, spleens were harvested from individual mice confirmed to have increased antibody titers, and about $1 \times 10^7$ B-cell populations were stimulated with immunogens, seeded in wells, and B cells were collected from wells in which antibodies reactive with the antigens were detected by fluorescence microscope (reference Jin et al. Nat. Med. (2009) 15: 1088-1092). RNA from respective cells was prepared and subjected to reverse transcription-PCR (RT-PCR) using immunoglobulin gene (IgG heavy and light chains)-specific primers. cDNAs containing the variable regions were amplified. E. coli was transformed by introducing plasmid DNA containing homologous sequences, and antibody-producing plasmids were generated. The obtained antibody-producing plasmid was transfected into HEK293T cells, etc., and reactivity to the antigen was confirmed again using a culture supernatant containing the antibody. Sequences were confirmed only for plasmid DNAs with antigen reactivity, resulting as confirmed antibody cDNA.

Plasmid DNA sequencing was performed with a capillary sequencer (Thermo Fisher Scientific), after reaction in a thermal cycler (BioRad) using BigDye Terminator v3.1

(Thermo Fisher Scientific) and CMV promotor primers and removal of unreacted reagents by FastGene Dye Terminator Removal Kit (Nippon Genetics). The obtained DNA sequences were subjected to homology searches and compared with existing DNA sequences.

Immunization with the Glyco-L-HBsAg resulted in the successful acquisition of antibody cDNAs from nine B cells recognizing PreS1 regions (FIGS. 20A and B).

[Variable Region Sequences of Antibody cDNA (PreS1) (FIGS. 20A and B)]

FIG. 20 shows IgG heavy chain amino acid sequences (A) and IgG light chain amino acid sequences (B) of antibodies that recognize PreS1. From comparisons of the variable region amino acid sequences, the sequences were divided into three groups. In FIG. 20A, the 06G-aa.seq is shown as SEQ ID NO: 5, 14G-aa.seq is shown as SEQ ID NO: 7, and 25G-aa.seq is shown as SEQ ID NO: 9. In FIG. 20B, 06K-aa.seq is shown as SEQ ID NO: 6, 14K-aa.seq is shown as SEQ ID NO: 8, and 25K-aa.seq is shown as SEQ ID NO: 10.

Antibody-producing B cells were similarly collected from the splenocytes of mice immunized with the Glyco-PreS2 peptide to prepare RNA. Only one antibody-producing plasmid (F5 clone #4) reacting with the immunogen was acquired. A whole transcriptome analysis was performed by preparing m RNA from the splenocytes of a separate mouse (F3) immunized in the same period.

The spenocytes (about 1×10⁷ cells) of the mouse (F3) immunized with the Glyco-PreS2 peptide were centrifuged, washed with PBS, and then collected. Total RNA was prepared using RNeasy Plus Mini Kit (Qiagen) and concentrations were measured using NanoDrop (Thermo Fisher Scientific). Dynabeads mRNA DIRECT Kit (Thermo Fisher Scientific) was used to purify mRNA, which was quantified using an Agilent 2100 bioanalyzer. Libraries for the whole transcriptome were prepared using Ion Total RNA-Seq Kit v2 (Thermo Fisher Scientific). The libraries were amplified and analyzed using an Ion OneTouch 2.0 system and Ion-PGM (Thermo Fisher Scientific) to obtain sequences. Sequence data were analyzed using CLC Genomics Workbench (Qiagen) to extract sequences homologous to the F5 #4 clone, and consensus sequences were obtained (FIG. 21).

[Variable Region Sequences of Antibody cDNA (Glyco-PreS2, NGS) (FIGS. 21A and B)]

FIG. 21 shows (A) a cDNA sequence (SEQ ID NO: 1) and an amino acid sequence (SEQ ID NO: 3) of an IgG heavy chain of F5 clone #4 obtained as a result of immunizing with Glyco-PreS2 and rapid screening of B cells (F5 #4). Also shown are amino acid sequences homologous to F5 clone #4 from among RNA sequences of splenocytes of the separate mouse (F3) (F3 RNA, F3 RNA2). The figure also shows (B) a cDNA sequence (SEQ ID NO: 2) and an amino acid sequence (SEQ ID NO: 4) of an IgG light chain of F5 clone #4.

Mapping with F5 clone #4 confirmed highly homologous sequences in F3 mRNA, so it is believed that the activity confirmed by ELISA in the F3 serum is from antibodies similar to that of F5 clone #4 (FIGS. 21A and B).

The antibody cDNA (heavy chain (G) and light chain (K)) incorporated into expression vectors were prepared with GenElute™ HP Endotoxin-Free Plasmid Maxiprep Kit (Sigma-Aldrich) and transfected into HEK293T cells using Lipofectamine LTX Reagent (Thermo Fisher Scientific). Antibodies were purified from the culture solutions 3 days after changing to a protein-free medium. Mouse IgG antibodies were collected using ProG beads, eluted with 0.1 M glycine (pH 2.5), neutralized with 3M Tris-Cl (pH 8.5), and then buffer-exchanged with PBS. The purified antibodies were separated with 12.5% SDS-PAGE and confirmed by silver staining as described above (FIG. 22).

[Electrophoresis of Purified Antibody (Quantification of Antibody Amount) (FIG. 22)]

Figure 22:
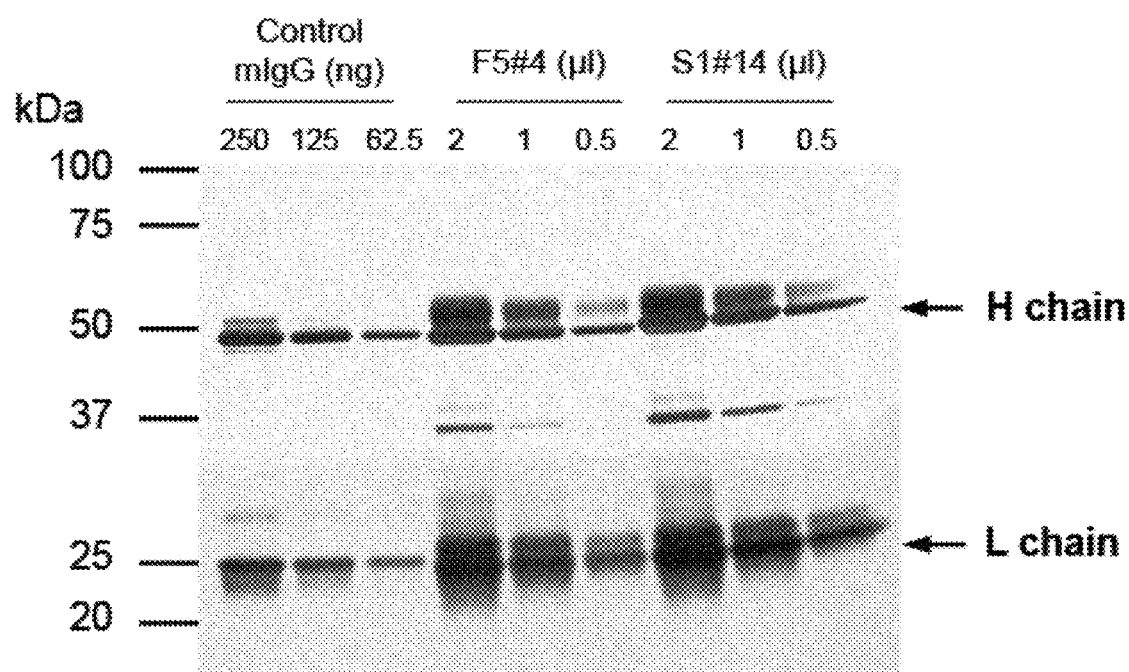

FIG. 22 shows the results obtained by SDS-PAGE and silver-staining for antibodies prepared by expressing antibody cDNAs. Clones acquired by Glyco-PreS2 immunization (F5 #4), clones acquired by Glyco-L-HBsAg immunization (S1 #14), commercially available murine IgGs (mIgG) were run as controls.

[Analysis of Antigenic Epitope Region Recognized by Each Antibody Clone]

Figure 23:
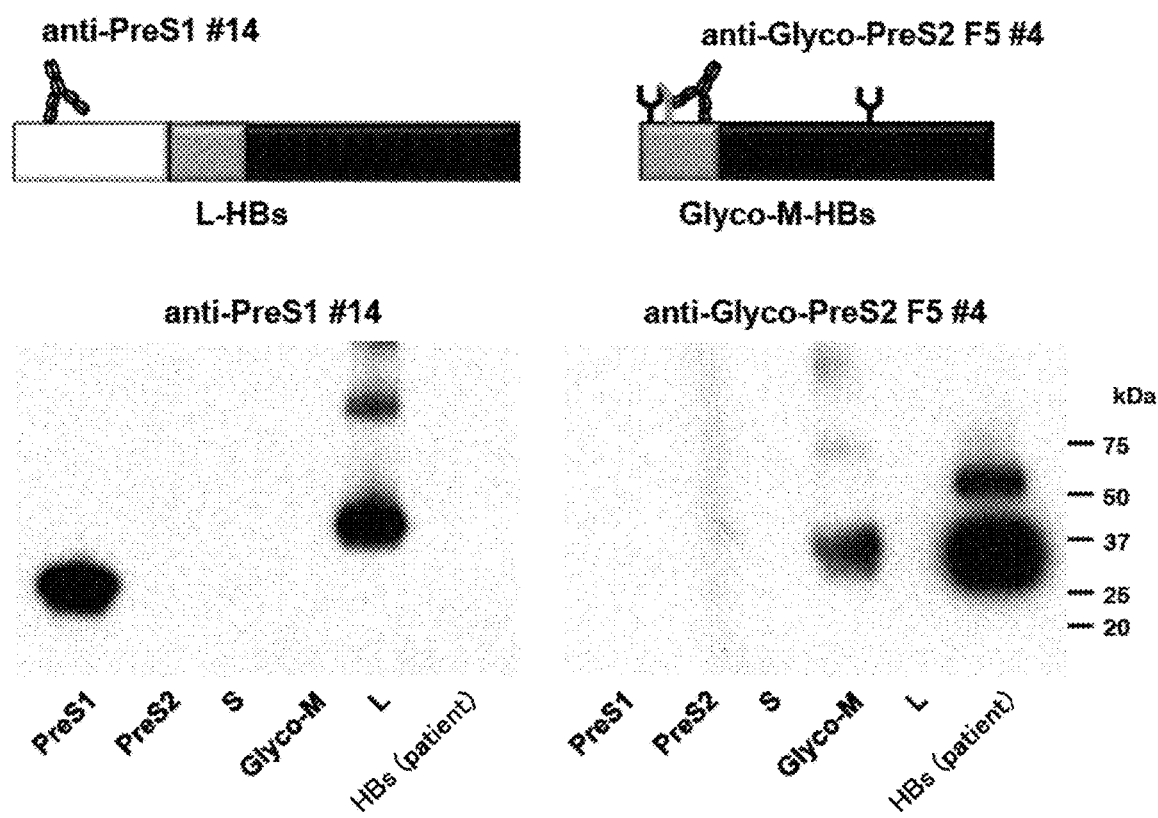

Western blotting was performed in the same manner as in FIG. 16 described above. The PreS1 peptide (*E. coli*), PreS2 peptide (*E. coli*), S-HBsAg (yeast), Glyco-M-HBsAg (HEK293), L-HBsAg (yeast), and HBsAg-(patient serum) were electrophoresed using 12.5% polyacrylamide gel under SDS-PAGE reducing conditions and transferred onto PVDF membranes. After blocking with PBS containing 10% skim milk, they were allowed to react with primary antibodies (respective clones of the anti-HBsAg-antibodies) for 1 hour at room temperature. After washing the PVDF membranes, they were allowed to react with a secondary antibody (0.5 μg/mL of an HRP-labeled anti-mouse IgG antibody) for 1 hour at room temperature. These PVDF membranes were washed and then detected by chemiluminescence with Western blotting detection reagents (Perkin Elmer) (FIG. 23).

[Western Blot (Purified Antibody, Anti-PreS1, Anti-Glyco-PreS2) (FIG. 23)]

The antibody (S1 #14) acquired by Glyco-L-HBsAg immunization shown in FIG. 22 and the antibody (F5 #4) acquired by Glyco-PreS2 immunization are believed to respectively recognize the PreS1 region (white) and the glycosylated PreS2 region (gray) but not the S region (black). For these antibodies, their reactivity to a tagged PreS1 (*E. coli*), tagged PreS2 (*E. coli*), S-HBsAg (yeast), Glyco-M-HBsAg (HEK293T), L-HBsAg (yeast), and patient serum-derived HBsAg was detected by Western blotting.

S1 #14 strongly recognized PreS1 and L-HBsAg (yeast) and barely recognized the patient-derived HBsAg. Meanwhile, it was found that F5 #4 strongly recognized the Glyco-M-HBsAg and patient-derived HBsAg, but did not recognize PreS2 and L-HBsAg (yeast) at all. The results were slightly different from those obtained with post-immunization sera (FIG. 16 and FIG. 18), which is believed to be attributed to being monoclonal antibodies.

Figure 24:
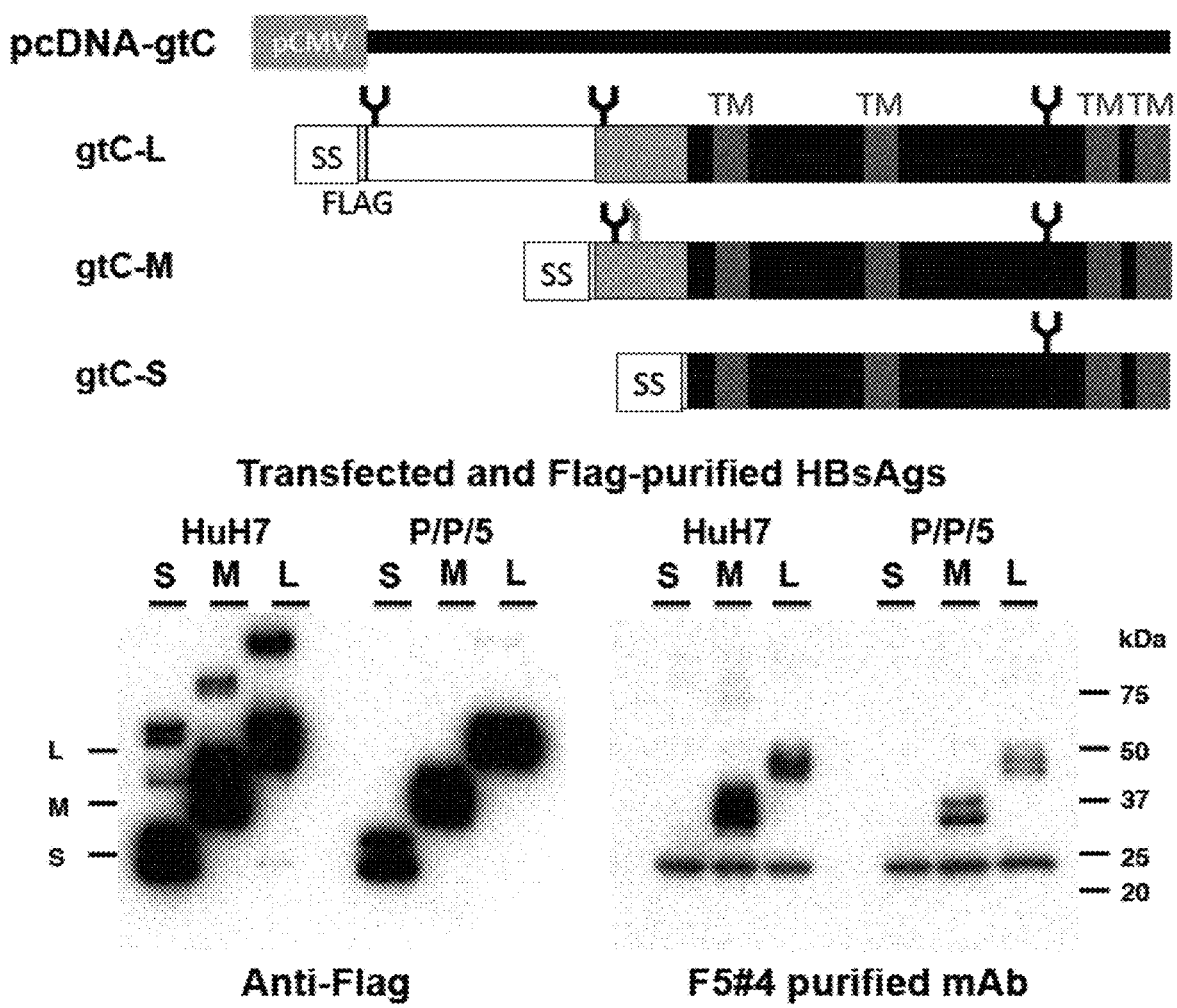

In order to express the HBsAgs of genotype C in hepatic cancer cells, the DNA encoding S-HBs, M-HBs, L-HBs was inserted into the expression vector pFLAG-CMV3 (Sigma-Aldrich). The HBsAgs thus expressed were FLAG-tagged at the N-terminus, allowing them to be purified and detected with anti-FLAG antibodies. The constructed expression plasmids of S-HBs, M-HBs, and L-HBs were transfected into the hepatic cancer cell line HuH7 and PLC/PRF/5 cells, respectively, using Lipofectamine 2000 (Thermo Fisher Scientific), and the culture supernatants were collected 48 hour later. The HBsAgs contained in the culture supernatants were purified using an anti-FLAG M2 antibody (Sigma-Aldrich). In order to confirm the reactivity of the F5 #4 antibody to the purified antigens, the purified HBsAgs were electrophoresed using 12.5% SDS-PAGE gel under reducing conditions and transferred to PVDF membranes. After blocking with PBS containing 10% skim milk, the F5 #4 antibody and an anti-FLAG antibody as a control were allowed to react for 1 hour at room temperature. After the PVDF membranes were washed, they were allowed to react with a secondary antibody (0.5 µg/mL of an HRP-labeled anti-mouse IgG antibody) for 1 hour at room temperature. These PVDF membranes were washed and then detected by chemiluminescence with Western blotting detection reagents (Perkin Elmer) (FIG. 24).

[Wester Blot (Purified F5 #4 Antibody, S, M, L Expressed in Cells) (FIG. 24)]

Genotype C HBsAgs (S-, M-, L-) were Flag-tagged and expressed in liver cancer cells (HuH7 and PLC/PRF/5 cells). The PreS1 region (white), PreS2 region (gray), and S regions (black) are N-glycosylated, respectively, and the PreS2 region of the M-HBsAg predominantly is O-glycosylated (see the schematic in the upper panel of FIG. 24, Table 3, and FIG. 7). Detection with an anti-Flag antibody shows that S-, M-, and L-HBsAgs antigens are recovered in almost the same amount (FIG. 24, lower left panel). Meanwhile, the purified F5 #4 antibody strongly recognizes the M-HBsAg and weakly recognizes the L-HBsAg. However, S-HBsAg is not recognized (FIG. 24, lower right panel).

O-glycan modification was observed only in a small proportion of PreS2 in the L-HBsAg in patient sera, and differences were observed in HuH7 and PLC/PRF/5 cells, so it is believed that these differences were due to the expression level of glycan genes expressed in the respective cells.

In order to express M-HBs of genotype C without the O-glycan, a mutant with threonine 37, to which the O-glycan is attached, converted to alanine was generated. Primers with the adenine in the threonine codon (ACT) changed to guanine (GCT) were designed, and the mutation was introduced by PCR. Moreover, DNA encoding M-HBs of genotype A was inserted into the expression vector pFLAG-CMV3 and used as a negative control. Sialic acid-deficient (− SLC35A1) cells and galactose-deficient (− SLC35A2) cells of HEK293 cells were generated by introducing inactivating mutations into a CMP-sialic acid transporter gene (SLC35A1) and a UDP-galactose transporter gene (SLC35A2) respectively, by genome editing using GeneArt CRISPR Nuclease Vector Kit (Thermo Fisher Scientific). Plasids were constructed with the target sequences to be mutated (SLC35A1: 5'-TGAACAGCATA-CACTAACGAgtttt-3' (SEQ ID NO: 39), SLC35A2: 5'-GCGTGTCCACATACTGCACCgtttt-3' (SEQ ID NO: 40)) cloned into the GeneArt CRISPR Nuclease CD4 Vector, and were transfected into HEK293 cells using Lipofectamine 2000 (Thermo Fisher Scientific). After 24-48 hours, using CD4 Enrichment Kit (Thermo Fisher Scientific), the cells into which the plasmids were introduced were selected and a plurality of single clones were isolated by limiting dilution. Using the isolated single clone strains, FACS analysis was performed with the SNA and MALII lectins that recognize sialic acid, and strains with reduced lectin signals were selected. The genomic DNA was extracted from those cells, the sequences around the target site were amplified by PCR, and direct sequencing was carried out to confirm that genome editing occurred at the target site. These cells were transfected with genotype C M-HBs, genotype C M-HBs without the O-glycan, or genotype A M-HBs, with the method described above, and each M-HBs was purified from the culture supernatant as described above in FIG. 24 and subjected to Western blot analysis (FIG. 25).

[Western Blot (Purified F5 #4 Antibody, Glyco-M Expressed in Cells) (FIG. 25)]

Figure 25:
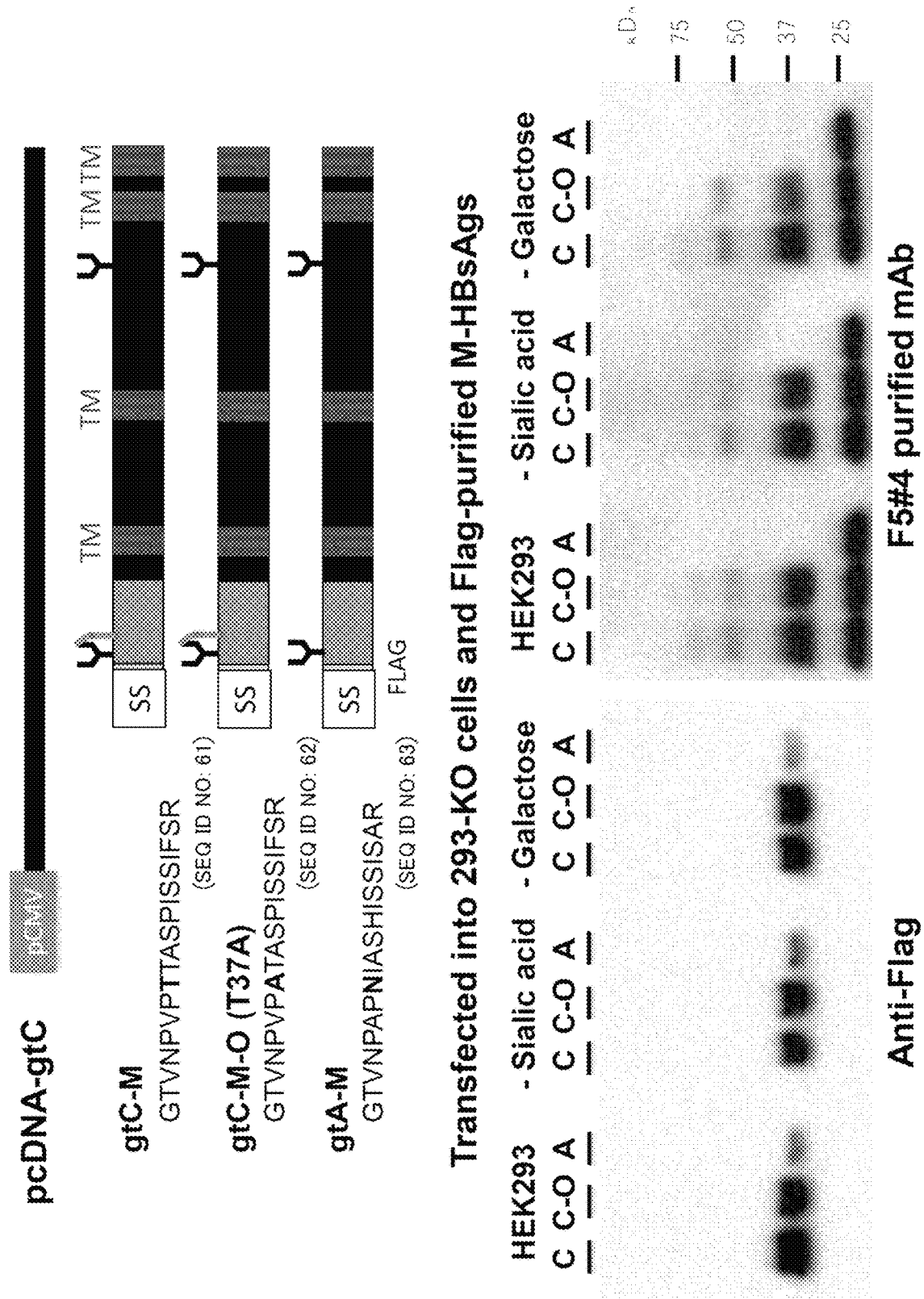

The schematic in the upper panel of FIG. 25 shows that M-HBsAgs of genotype C and genotype A were Flag-tagged and expressed in HEK293 cells, sialic acid-deficient cells (−SLC35A1), and galactose-deficient cells (−SLC35A2). The PreS2 region (gray) of genotype C is O-glycosylated, whereas the PreS2 region of genotype A is not O-glycosylated. The results in FIG. 25 show O-glycans attached to two threonines (T37 and T38), and an M-HBsAg with T37 mutated to alanine (T37A) was also expressed. Genotype C (C) and T37A mutant (C—O) M-HBsAgs were recovered in almost the same amounts (detected by an anti-Flag antibody, FIG. 25, lower left panel). The purified F5 #4 antibody detected C and C—O expressed in HEK293 cells and sialic acid-deficient cells (− Sialic acid) similarly. Meanwhile, since the detected levels of C and C—O expressed in the galactose-deficient cells (− Galactose) differ, the antigen recognition of F5 #4 antibody is believed to include galactose in the O-glycan (FIG. 25, lower right panel).

[Antibody-Antibody ELISA Measurement System Using Anti-HBs Antibody Obtained in the Present Invention]

(Detection of Total HBs Molecules by an Antibody-Antibody ELISA Measurement System)

The HBsAgs can also be detected by an antibody-antibody ELISA measuring system using the anti-HBs monoclonal antibodies. The established anti-HBs monoclonal antibodies were each immobilized to ELISA plates, and it is possible to examine whether the same or a separate anti-HBs antibody can be used on the detection side in the ELISA measurement system. Antibody combinations can generally be used either on the ELISA plate immobilization side or the detection side (liquid phase side), and a detection system is constructed with a combination of antibodies that are more sensitive. Generally, the detection system is constructed with a combination in which the sensitivity is high and the background noise is low.

First, each antibody (for immobilization) was diluted with PBS to 4 µg/mL, and 100 µL/well was added to an ELISA microplate. After each antibody is adsorbed to the plate overnight at 4° C., the solution was discarded and the wells were washed with PBS-T (PBS, 0.05% Tween-20). A blocking solution (PBS with 3% BSA) was then added at 300 µL/well to carry out blocking. After the blocking solution was discarded and the wells were washed, sample (various HBsAgs, HBV virus particles) solutions were added at 100 µL to each well. After 2 hours of reaction at 37° C., the solution in the well was discarded, the wells were washed with PBS-T, and then a biotin-labeled anti-HBs antibody (R&D biotinylated anti-HBs pAb Cat #BAF329) prepared at 2 µg/mL was reacted at room temperature for 1 hour. Thereafter, the solutions were discarded and washed, and then 100 µL of a horseradish peroxidase (HRP)-labeled streptavidin (Jackson) solution was added to each well and allowed to react for 1 hour at room temperature. After the reaction solution was discarded and washed, color development of 1StepUltra TMB substrate (Pierce) was measured at an absorbance of 450 nm. In addition to detection by the ELISA system using a monoclonal antibody-polyclonal antibody (or antiserum), other than the polyclonal antibody, a monoclonal antibody may be used as another combination. In such cases, it is desirable to use detectable combinations and select combinations of higher sensitivity.

Following references (Hamada-Tsutsumi et al. *PLoS ONE* (2015) 10: e0118062.), the antibodies developed in the present invention were confirmed to inhibit HBV-infection.

Experiments involving infection of hepatocytes with HBV are generally not achieved in human hepatic cancer cells or mouse hepatocytes. Primary cells of human hepatocytes or cells from human liver chimeric mice (PXB cells, Phoenix Bio) were cultured and HBV was added to the culture medium to induce HBV infection. For infection inhibition experiments, HBV was first mixed with antibodies or antigen-induced sera to allow the antibodies to bind to HBV and then added to the cells. Mouse sera and IgG were used as negative controls, and mouse antibodies or sera induced by the current vaccine, anti-HBs antibodies (HBIG) purified from human blood, etc. were used as positive controls.

[Experimental Protocol for HBV Infection Inhibition (FIG. 26)]

Figure 26:
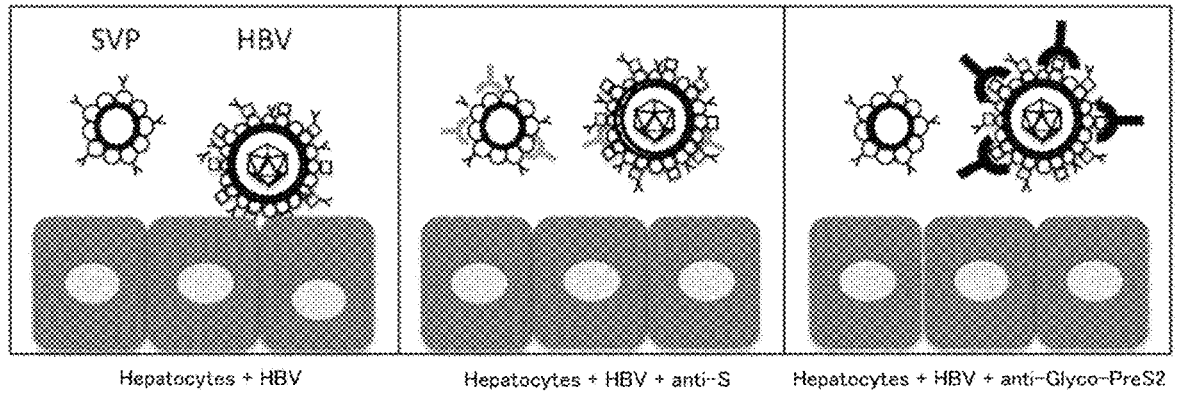

FIG. 26 shows an experimental protocol for HBV infection inhibition with antibodies and antisera. Cells (PXB cells) from human liver chimeric mice, antibodies, and antisera, and genotype C HBV amplified in mice as a source of infection were used. HBV mixed with the antibodies or antisera for 2 hours was added to the culture medium of PXB cells at 5 genome/cell. The cells were washed over the following two days, and the supernatants were collected later on Days 8, 13, 18, and 23 to measure HBV DNA and HBsAg level.

Lower panel of FIG. 26: Images of HBV infection inhibition experiments. Hepatocytes were cultured and HBV was added. The added HBV also contains the subviral particles SVP (FIG. 26, left). S-HBsAg are expressed in SVP, and vaccine-induced antibodies (anti-S) also react to SVP. However, the antibodies (anti-PreS2) in the present invention mainly react to HBV, rather than to SVP, and efficiently inhibit infection. It is clear that most of the subviral particles consist only of the S-HBsAg.

In the method shown in FIG. 26, the HBV infection inhibitory activity of the F5 antibody according to Glyco-PreS2 of the present invention was compared with that of a commercially available HBIG (purified antibody from S-antigen vaccinees).

The two antibodies (F5 antibody and HBIG) were separated by SDS-PAGE and silver-stained to analyze the purity and concentration of the antibodies. The same amounts of the antibodies were used to perform experiments on the inhibition of infection of PXB cells with HBV (genotype C). PXB cells ($7 \times 10^4$ cells/well) were seeded on 96-well collagen-coated plates and were cultured with HBV at 5 GEq/cell ($3.5 \times 10^5$ copies/well). The F5 antibody or HBIG (0-1000 ng) and HBV were pre-incubated for 2 hours at 37° C. They were subsequently allowed to infect the PXB cells without using PEG, and the infection-inhibiting activities of the antibodies were compared. After infection at 37° C. for 48 hours, the culture supernatants containing HBV-antibody were removed and replaced with new media, and culturing was performed along the time axis shown in FIG. 26. The culture supernatants on Day 8 and Day 13 post-infection were collected, and HBV DNA was purified in 100 µL of culture supernatants containing HBV released from infected PXB cells (same procedure as the separation of HBV by the Jacalin lectin). The amount of HBV DNA in the culture supernatants is quantified by real-time quantitative PCR as in FIG. 5B.

[Experiment of HBV Infection Inhibition (HBV DNA) (FIG. 27)]

Figure 27:
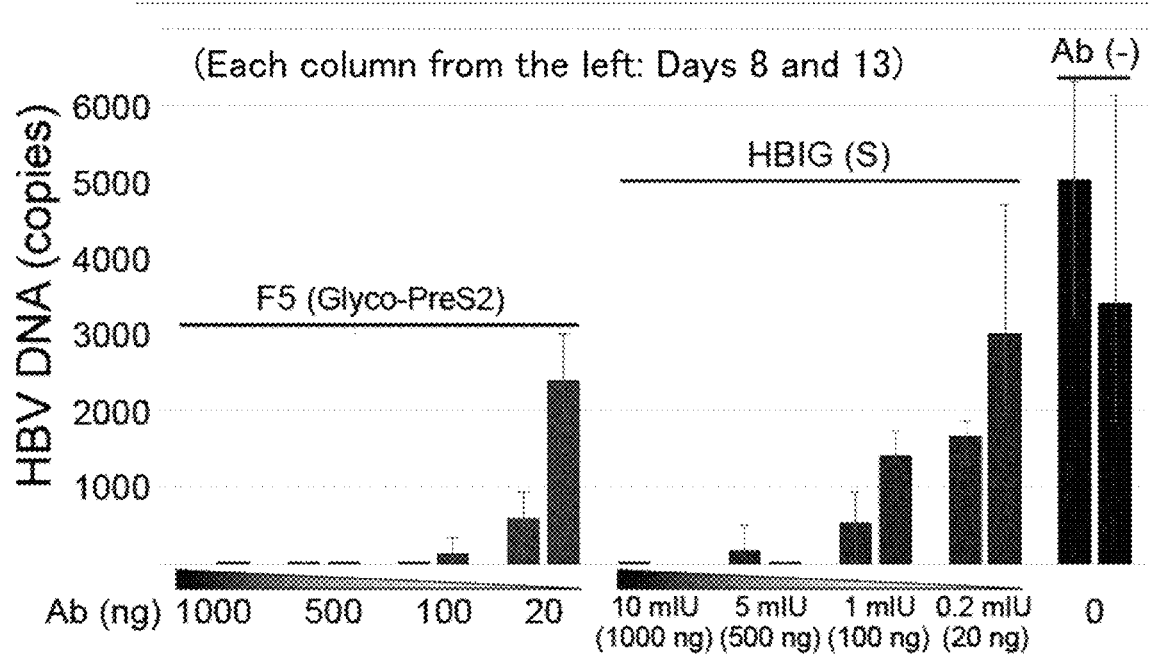
Figure 28:
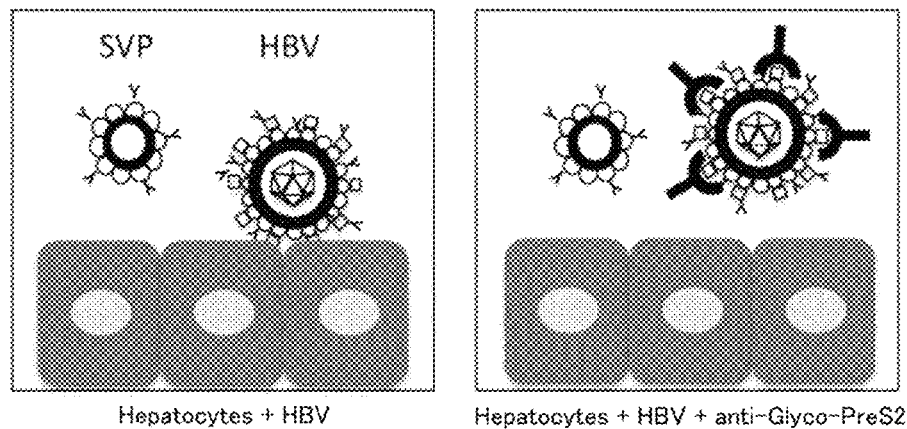

FIG. 27 shows the results of an HBV infection experiment using PXB cells and genotype C HBV. HBV was incubated with the F5 antibody or HBIG (0-1000 ng) to allow adsorption, and the infection inhibiting activities were compared. HBV released from hepatocytes after infection was quantified by measuring HBV DNA by real-time PCR.

The F5-antibody exhibited sufficient inhibition of the HBV infection even at 100 ng, whereas HBIG 100 ng did not sufficiently inhibit the HBV infection (FIG. 27). These results suggest that the F5 antibody has a similar or greater inhibiting activities than HBIG of blood preparations, which have used in mother-to-child transmission and needlestick accidents. That is to say, the glycopeptide capable of inducing the present antibody can be expected to provide effects as a vaccine.

Thus, the present invention provides techniques and products for acquiring examination systems that can recognize glycosylated antigens, vaccines that can induce antibodies capable of recognizing glycosylated antigens, or neutralizing antibodies that recognize glycosylated antigens and that exhibit infection-inhibiting activities, so as to provide a broad coverage of the above cases that currently need to be addressed.

Moreover, the experimental procedures in the present invention will be explained individually.

[Glycan Analysis of HBV (HBsAg)]

In order to analyze the presence or absence of glycans and other post-translational modifications in the envelope proteins of HBV (L-, M-, and S-HBsAgs), purified HBsAgs obtained from sera were used to examine a glycoproteomic analysis using a mass spectrometer and the glycosylation sites on the purified HBsAgs were determined. Further, the glycan structures were determined by MS/MS analysis.

[Construction of New HBsAg Measurement System]

HBV in vivo is present with a much greater proportion of non-infectious (nucleic acid-free) subviral particles than infectious (nucleic acid-containing) virus particles (called Dane particles), and the current HBsAg measurement systems cannot accurately measure only the infectious Dane particles. Moreover, an analysis of the HBsAgs on the surface of HBV suggests that the antibody population established following vaccination with the existing vaccine poorly reacts to glycosylated HBsAgs, which may be related to occult infection. Therefore, by comparing with the results of Western blotting for purified HBsAgs of human anti-HBsAg antibodies derived from B cell clones induced by vaccination, new detection methods of HBsAgs by a combination of a glycan-recognizing lectin and an antibody were investigated. In the present invention, it is possible to construct a new detection system which is suitable for the identification of Dane particles and is not affected by the glycan on the S-HBsAg.

[Construction of New HBV DNA Measurement System]

Although the safety of blood donation is ensured by screening with nucleic acid tests (NAT), HBV infection is established at a low copy at or below the detection limit, so incidents of infection through blood transfusions still take place compared with HCV and HIV. That is, techniques to concentrate Dane particles are essential to increase the accuracy of HBV detection. A system for measuring Dane particle quantity was constructed by using the sera of HBV-infected patients with different liver backgrounds, such as treatment histories, HBV DNA copy numbers, genotypes, etc., and using a probe lectin specific for a glycan of Dane particles. Effectiveness was demonstrated in the selection and concentration of Dane particles and in trace detection systems using this lectin probe. Moreover, it is possible to develop systems for concentrating and measuring a Dane particulate quantity using the novel antibodies developed in the present invention.

[Synthesis and Large-Scale Purification of HBsAg with Glycan Modification]

The current S-HBsAg, used as a vaccine, is not glycan-modified. In order to determine peptides or HBsAgs suitable as vaccines, a detailed analysis of glycosylation sites and glycan structures on PreS1, PreS2, and S was first performed to obtain the basic information for vaccine development. Glycosylated HBsAg (yeast) and peptides (transglycosylation or enzymatic methods) were prepared (glycosylated L-HBsAg, glycosylated M-HBsAg, PreS1 peptide, PreS2 peptide, glycosylated PreS2 peptide, etc.). Mice were vaccinated (immunized) therewith, blood was collected over time, and increases in antibody titers were confirmed by ELISA, resulting in the successful acquisition of serogroups that recognize almost the entire region of the HBsAg. Moreover, these antigens were confirmed to be effective as vaccines (antigens) that increase antibody titers.

[Infection Inhibiting Effect by Induced Anti-HBs Antibody]

Since inhibiting activities were also confirmed, this is expected to lead to the development of new vaccines. Moreover, from the differences in antibody titers and antibody populations increased by the immunization with the L-HBsAg and the S-HBsAg, an improvement in the vaccination method resulted in the acquisition of a wide range of antibodies with a small number of doses. Further, since the rapid screening of B cells from murine splenocytes led to the successful cloning of several antibody cDNA, it is also possible to use mixed monoclonal antibodies as alternatives to HBIG as neutralizing antibodies (drugs used as urgent treatments immediately after infection incidents).

Sequence Listing

The invention claimed is:

1. An anti-hepatitis B virus antigen antibody, comprising:

three CDR sequences at positions 45 to 52, 70 to 77 and 116 to 129 of the amino acid sequence set forth in SEQ ID NO: 3 and three CDR sequences at positions 46 to 56, 74 to 76 and 113 to 121 of the amino acid sequence set forth in SEQ ID NO: 4; or three CDR sequences at positions 44 to 51, 70 to 76 and 115 to 121 of the amino acid sequence set forth in SEQ ID NO: 5 and three CDR sequences at positions 46 to 56, 74 to 76 and 113 to 121 of the amino acid sequence set forth in SEQ ID NO: 6; or three CDR sequences at positions 45 to 51, 70 to 79 and 118 to 128 of the amino acid sequence set forth in SEQ ID NO: 7 and three CDR sequences at positions 47 to 58, 76 to 78 and 115 to 123 of the amino acid sequence set forth in SEQ ID NO: 8; or three CDR sequences at positions 45 to 51, 70 to 79 and 118 to 128 of the amino acid sequence set forth in SEQ ID NO: 9 and three CDR sequences at positions 47 to 52, 70 to 72 and 109 to 117 of the amino acid sequence set forth in SEQ ID NO: 10.

2. The anti-hepatitis B virus antigen antibody according to claim 1, comprising the amino acid sequences set forth in SEQ ID NOs: 3 and 4, or the amino acid sequences set forth in SEQ ID NOs: 5 and 6, or the amino acid sequences set forth in SEQ ID NOs: 7 and 8, or the amino acid sequences set forth in SEQ ID NOs: 9 and 10.

3. A nucleic acid encoding the amino acid sequences of the anti-hepatitis B virus antigen antibody according to claim 1.

4. The nucleic acid according to claim 3, comprising the nucleotide sequence set forth in SEQ ID NO: 1 or 2.

5. An expression vector comprising the nucleic acid according to claim 3.

6. An anti-hepatitis B virus pharmaceutical composition, comprising the antibody according to claim 1.

7. A method for detecting a Dane particle of hepatitis B virus, comprising using the antibody according to claim 1 to detect the Dane particle of hepatitis B virus.

8. The method according to claim 7, further comprising using a lectin.

9. A kit for detecting a Dane particle of hepatitis B virus, comprising the antibody according to claim 1.

* * * * *

UNITED STATES PATENT AND TRADEMARK OFFICE
CERTIFICATE OF CORRECTION

| | |
|---|---|
| PATENT NO. | : 11,571,473 B2 |
| APPLICATION NO. | : 16/972367 |
| DATED | : February 7, 2023 |
| INVENTOR(S) | : Hisashi Narimatsu et al. |

It is certified that error appears in the above-identified patent and that said Letters Patent is hereby corrected as shown below:

On the Title Page

Item (73) - Assignees, please correct this section to read as follows:
NATIONAL INSTITUTE OF ADVANCED INDUSTRIAL SCIENCE AND TECHNOLOGY, Tokyo (JP); UNIVERSITY OF TOYAMA, Toyama (JP)

Signed and Sealed this
Eleventh Day of April, 2023

Katherine Kelly Vidal
*Director of the United States Patent and Trademark Office*

SEQUENCE LISTING

```
<160> NUMBER OF SEQ ID NOS: 64

<210> SEQ ID NO 1
<211> LENGTH: 552
<212> TYPE: DNA
<213> ORGANISM: Mus musculus

<400> SEQUENCE: 1
atgggatgga gatggatcct tcttttcctc ctgtcaggaa ctgcaggtgt ccactgccag     60
gttcagctgc agcagtccgg acctgagctg gtgaagcctg gggctttagt gaagatatcg    120
tgcaaggctt ctggttacac cttcacaagc tacgatataa actgggtgaa gcagaggcct    180
ggacagggac ttgagtggat tggatggatt tatcctggag atggtcgtac taagtacaat    240
gagaaattca agggcaaggc cacactgact gcagacaaat cctccagcac agcctatatg    300
cagctcagca gcctgacttc tgagaactct gcagtctatt tttgtgtaag atcacacgat    360
agtaattacg gggcctggtt tccttactgg ggccaaggga ctctggtcac tgtctctgca    420
gccaaaacga cacccccatc tgtctatcca ctggcccctg gatctgctgc ccaaactaac    480
tccatggtga ccctgggatg cctggtcaag ggctatttcc ctgagccagt gacagtgacc    540
tggaactctg ga                                                        552

<210> SEQ ID NO 2
<211> LENGTH: 450
<212> TYPE: DNA
<213> ORGANISM: Mus musculus

<400> SEQUENCE: 2
atgaagttgc ctgttaggct gttggtgctg atgttctgga ttcctgcttc cagaagtgat     60
gtattgatga cccaaactcc actctccctg cctgtcagtc ttggaaatca agcctccatc    120
tcttgcagat ctagtcagaa cattgtacat agtaatggaa acacctattt agaatggtac    180
ctgcagaaac caggccagtc tccaaagctc ctgatctaca aagtttctaa ccgattttct    240
ggggtccccg acaggttcag tggcagtgga tcagggacag atttcacact caagatcagc    300
agagtggagg ctgaggatct gggagtttat tactgctttc aaggttcaca tgttccgctc    360
acgttcggta ctgggaccaa gctggagctg aaacgggctg atgctgcacc aactgtatcc    420
atcttcccac catccagtga gcagttaaca                                     450

<210> SEQ ID NO 3
<211> LENGTH: 184
<212> TYPE: PRT
```

<213> ORGANISM: Mus musculus

<400> SEQUENCE: 3

```
Met Gly Trp Arg Trp Ile Leu Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Ser Tyr Asp Ile Asn Trp Val Lys Gln Arg Pro Gly Gln Gly Leu
    50                  55                  60

Glu Trp Ile Gly Trp Ile Tyr Pro Gly Asp Gly Arg Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asn Ser Ala Val
            100                 105                 110

Tyr Phe Cys Val Arg Ser His Asp Ser Asn Tyr Gly Ala Trp Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly
            180
```

<210> SEQ ID NO 4
<211> LENGTH: 150
<212> TYPE: PRT
<213> ORGANISM: Mus musculus

<400> SEQUENCE: 4

```
Met Lys Leu Pro Val Arg Leu Leu Val Leu Met Phe Trp Ile Pro Ala
1               5                   10                  15

Ser Arg Ser Asp Val Leu Met Thr Gln Thr Pro Leu Ser Leu Pro Val
            20                  25                  30

Ser Leu Gly Asn Gln Ala Ser Ile Ser Cys Arg Ser Ser Gln Asn Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Leu Thr Phe Gly Thr Gly Thr Lys Leu
        115                 120                 125

Glu Leu Lys Arg Ala Asp Ala Ala Pro Thr Val Ser Ile Phe Pro Pro
    130                 135                 140

Ser Ser Glu Gln Leu Thr
145                 150
```

<210> SEQ ID NO 5
<211> LENGTH: 131
<212> TYPE: PRT
<213> ORGANISM: Mus musculus

<400> SEQUENCE: 5

Met Lys Val Leu Ser Leu Leu His Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Thr Tyr Tyr Trp Asn Trp Ile Arg Gln Phe Pro Gly Asn Lys Leu
    50                  55                  60

Glu Trp Met Gly Tyr Ile Ser Tyr Asp Gly Ser Thr Asn Tyr His Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Ala Glu Asp Thr Ala Thr Tyr
            100                 105                 110

Tyr Cys Ser Arg Gly Ile Thr Tyr Tyr Trp Gly Gln Gly Thr Thr Leu
        115                 120                 125

Thr Val Ser
    130

<210> SEQ ID NO 6
<211> LENGTH: 131
<212> TYPE: PRT
<213> ORGANISM: Mus musculus

<400> SEQUENCE: 6

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Ser Thr His Ile Pro His Thr Phe Gly Gly Gly Thr Lys Leu
        115                 120                 125

Glu Ile Lys
    130

<210> SEQ ID NO 7
<211> LENGTH: 138
<212> TYPE: PRT
<213> ORGANISM: Mus musculus

<400> SEQUENCE: 7

Met Tyr Leu Gly Leu Asn Cys Val Phe Ile Val Phe Leu Leu Lys Gly
1               5                   10                  15

```
Val Gln Ser Glu Val Lys Leu Glu Glu Ser Gly Gly Gly Leu Val Gln
            20                  25                  30

Pro Gly Gly Ser Met Lys Phe Thr Cys Val Ala Ser Gly Phe Thr Phe
        35                  40                  45

Ser Asn Tyr Trp Met Asn Trp Val Arg Arg Ser Pro Glu Lys Gly Leu
    50                  55                  60

Glu Trp Val Ala Glu Ile Arg Leu Lys Ser Asp Asn Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Gly Glu Asp Thr
            100                 105                 110

Ala Ile Tyr Tyr Cys Thr Ser Pro Thr Ser Gly Thr Pro Phe Ala Tyr
        115                 120                 125

Trp Gly Gln Gly Thr Leu Val Ile Val Ser
    130                 135

<210> SEQ ID NO 8
<211> LENGTH: 133
<212> TYPE: PRT
<213> ORGANISM: Mus musculus

<400> SEQUENCE: 8

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Pro
            20                  25                  30

Val Ser Val Gly Glu Lys Val Thr Met Ser Cys Arg Ser Ser Gln Ser
        35                  40                  45

Leu Leu Tyr Ser Asn Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Ile Tyr
            100                 105                 110

Tyr Cys Gln Gln Tyr Tyr Thr Tyr Pro Trp Thr Phe Gly Gly Gly Thr
        115                 120                 125

Lys Leu Glu Ile Lys
    130

<210> SEQ ID NO 9
<211> LENGTH: 138
<212> TYPE: PRT
<213> ORGANISM: Mus musculus

<400> SEQUENCE: 9

Met Tyr Leu Gly Leu Asn Cys Val Phe Ile Val Phe Leu Leu Lys Gly
1               5                   10                  15

Val Gln Ser Glu Val Asn Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Asn Asn Tyr Trp Met Asn Trp Val Arg Gln Ser Pro Glu Lys Gly Leu
    50                  55                  60
```

```
Glu Trp Val Ala Glu Ile Arg Val Glu Ser Asn Asp Tyr Ala Thr His
 65                  70                  75                  80

Tyr Ala Glu Ser Val Lys Gly Arg Phe Thr Ile Ser Arg Asp Asp Ser
                 85                  90                  95

Lys Ser Ser Val Tyr Leu Gln Met Asn Asn Leu Arg Ala Glu Asp Thr
                100                 105                 110

Gly Ile Tyr Tyr Cys Thr Ser Pro Thr Ala Gly Thr Pro Phe Ala Tyr
            115                 120                 125

Trp Gly Gln Gly Ile Leu Val Thr Val Ser
        130                 135

<210> SEQ ID NO 10
<211> LENGTH: 127
<212> TYPE: PRT
<213> ORGANISM: Mus musculus

<400> SEQUENCE: 10

Met Glu Ser His Thr Gln Ala Phe Val Phe Ala Phe Leu Trp Leu Ser
  1               5                  10                  15

Gly Val Asp Gly Asp Ile Val Met Thr Gln Ser Gln Lys Phe Met Ser
                 20                  25                  30

Thr Ser Val Gly Asp Arg Val Ser Ile Thr Cys Lys Ala Ser Gln Asn
             35                  40                  45

Val Gly Thr Ala Val Ala Trp Tyr Gln Gln Lys Pro Gly Gln Ser Pro
         50                  55                  60

Lys Leu Leu Ile Tyr Ser Ala Ser Asn Arg Tyr Thr Gly Val Pro Asp
 65                  70                  75                  80

Arg Phe Thr Gly Ser Gly Ser Gly Thr Asp Phe Thr Leu Thr Ile Ser
                 85                  90                  95

Asn Met Gln Ser Glu Asp Leu Ala Asp Tyr Phe Cys Gln Gln Tyr Ser
                100                 105                 110

Ser Tyr Pro Tyr Thr Phe Gly Gly Gly Thr Lys Leu Glu Ile Lys
            115                 120                 125

<210> SEQ ID NO 11
<211> LENGTH: 55
<212> TYPE: PRT
<213> ORGANISM: Hepatitis B virus

<400> SEQUENCE: 11

Met Gln Trp Asn Ser Thr Thr Phe His Gln Ala Leu Leu Asp Pro Arg
  1               5                  10                  15

Val Arg Gly Leu Tyr Leu Pro Ala Gly Gly Ser Ser Ser Gly Thr Val
                 20                  25                  30

Asn Pro Val Pro Thr Thr Ala Ser Pro Ile Ser Ser Ile Phe Ser Arg
             35                  40                  45

Thr Gly Asp Pro Ala Pro Asn
         50                  55

<210> SEQ ID NO 12
<211> LENGTH: 32
<212> TYPE: PRT
<213> ORGANISM: Hepatitis B virus

<400> SEQUENCE: 12

Val Arg Gly Leu Tyr Phe Pro Ala Gly Gly Ser Ser Ser Gly Thr Val
  1               5                  10                  15
```

Asn Pro Val Pro Thr Thr Ala Ser Pro Ile Ser Ser Ile Phe Ser Arg
            20                  25                  30

<210> SEQ ID NO 13
<211> LENGTH: 400
<212> TYPE: PRT
<213> ORGANISM: Hepatitis B virus

<400> SEQUENCE: 13

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Arg Thr Cys Thr Ile Pro Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
        355                 360                 365

Ile Trp Met Met Trp Tyr Trp Gly Pro Ser Leu Tyr Asn Ile Leu Ser
370 375 380

Pro Phe Leu Pro Leu Leu Pro Ile Phe Phe Cys Leu Trp Val Tyr Ile
385 390 395 400

<210> SEQ ID NO 14
<211> LENGTH: 400
<212> TYPE: PRT
<213> ORGANISM: Hepatitis B virus

<400> SEQUENCE: 14

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Val Leu Thr Thr Val Pro Val Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Leu Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro

```
                    340                 345                 350
Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Asn Ile Leu Ser
        370                 375                 380

Pro Phe Leu Pro Leu Leu Pro Ile Phe Phe Cys Leu Trp Val Tyr Ile
385                 390                 395                 400
```

<210> SEQ ID NO 15
<211> LENGTH: 32
<212> TYPE: PRT
<213> ORGANISM: Artificial Sequence
<220> FEATURE:
<223> OTHER INFORMATION: synthetic construct

<400> SEQUENCE: 15

```
Val Arg Gly Leu Tyr Leu Pro Ala Gly Gly Ser Ser Gly Thr Val
1               5                   10                  15

Asn Pro Val Pro Thr Thr Ala Ser Pro Ile Ser Ser Ile Phe Ser Arg
            20                  25                  30
```

<210> SEQ ID NO 16
<211> LENGTH: 21
<212> TYPE: PRT
<213> ORGANISM: Artificial Sequence
<220> FEATURE:
<223> OTHER INFORMATION: synthetic construct

<400> SEQUENCE: 16

```
Ser Ser Ser Gly Thr Val Asn Pro Val Pro Thr Thr Ala Ser Pro Ile
1               5                   10                  15

Ser Ser Ile Phe Ser
            20
```

<210> SEQ ID NO 17
<211> LENGTH: 13
<212> TYPE: PRT
<213> ORGANISM: Artificial Sequence
<220> FEATURE:
<223> OTHER INFORMATION: synthetic construct

<400> SEQUENCE: 17

```
Thr Val Asn Pro Val Pro Thr Thr Ala Ser Pro Ile Ser
1               5                   10
```

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
cttcatcctg ctgctatgcc t                                         21

<210> SEQ ID NO 19
<211> LENGTH: 20
<212> TYPE: DNA
<213> ORGANISM: Artificial Sequence
<220> FEATURE:
<223> OTHER INFORMATION: synthetic construct

<400> SEQUENCE: 19
aaagcccagg atgatgggat                                           20

<210> SEQ ID NO 20
<211> LENGTH: 28
<212> TYPE: DNA
<213> ORGANISM: Artificial Sequence
<220> FEATURE:
<223> OTHER INFORMATION: synthetic construct

<400> SEQUENCE: 20
atgttgcccg tttgtcctct aattccag                                    28

<210> SEQ ID NO 21
<211> LENGTH: 26
<212> TYPE: PRT
<213> ORGANISM: Hepatitis B virus

<400> SEQUENCE: 21

Lys Gly Met Gly Thr Asn Leu Ser Val Pro Asn Pro Leu Gly Phe Phe
1               5                   10                  15

Pro Asp His Gln Leu Asp Pro Ala Phe Lys
            20                  25

<210> SEQ ID NO 22
<211> LENGTH: 25
<212> TYPE: PRT
<213> ORGANISM: Hepatitis B virus

<400> SEQUENCE: 22

Gly Met Gly Thr Asn Leu Ser Val Pro Asn Pro Leu Gly Phe Phe Pro
1               5                   10                  15

Asp His Gln Leu Asp Pro Ala Phe Lys
            20                  25

<210> SEQ ID NO 23
<211> LENGTH: 22
<212> TYPE: PRT
<213> ORGANISM: Hepatitis B virus

<400> SEQUENCE: 23

Asp Ser His Pro Gln Ala Met Gln Trp Asn Ser Thr Thr Phe His Gln
1               5                   10                  15

Ala Leu Leu Asp Pro Arg
            20

<210> SEQ ID NO 24
<211> LENGTH: 24
<212> TYPE: PRT
<213> ORGANISM: Hepatitis B virus

<400> SEQUENCE: 24

Asp Ser His Pro Gln Ala Met Gln Trp Asn Ser Thr Thr Phe His Gln
1               5                   10                  15

Ala Leu Leu Asp Pro Arg Val Arg
            20

<210> SEQ ID NO 25
<211> LENGTH: 16
<212> TYPE: PRT
<213> ORGANISM: Hepatitis B virus

<400> SEQUENCE: 25

Met Gln Trp Asn Ser Thr Thr Phe His Gln Ala Leu Leu Asp Pro Arg
1               5                   10                  15

<210> SEQ ID NO 26
<211> LENGTH: 19
<212> TYPE: PRT
<213> ORGANISM: Hepatitis B virus

<400> SEQUENCE: 26

Pro Thr Asp Gly Asn Cys Thr Cys Ile Pro Ile Pro Ser Ser Trp Ala
1               5                   10                  15

Phe Ala Lys

<210> SEQ ID NO 27
<211> LENGTH: 19
<212> TYPE: PRT
<213> ORGANISM: Hepatitis B virus

<400> SEQUENCE: 27

Pro Ser Asp Gly Asn Cys Thr Cys Ile Pro Ile Pro Ser Ser Trp Ala
1               5                   10                  15

Phe Ala Lys

<210> SEQ ID NO 28
<211> LENGTH: 19
<212> TYPE: PRT
<213> ORGANISM: Hepatitis B virus

<400> SEQUENCE: 28

Pro Ser Asp Gly Asn Cys Thr Cys Ile Pro Ile Pro Ser Ser Trp Ala
1               5                   10                  15

Phe Gly Lys

<210> SEQ ID NO 29
<211> LENGTH: 38
<212> TYPE: PRT
<213> ORGANISM: Hepatitis B virus

<400> SEQUENCE: 29

Thr Cys Thr Ile Pro Ala Gln Gly Thr Ser Met Phe Pro Ser Cys Cys
1               5                   10                  15

Cys Thr Lys Pro Ser Asp Gly Asn Cys Thr Cys Ile Pro Ile Pro Ser
            20                  25                  30

Ser Trp Ala Phe Ala Arg
            35

<210> SEQ ID NO 30
<211> LENGTH: 19
<212> TYPE: PRT
<213> ORGANISM: Hepatitis B virus

<400> SEQUENCE: 30

Pro Ser Asp Gly Asn Cys Thr Cys Ile Pro Ile Pro Ser Ser Trp Ala
1               5                   10                  15

Phe Ala Arg

<210> SEQ ID NO 31
<211> LENGTH: 32
<212> TYPE: PRT
<213> ORGANISM: Artificial Sequence
<220> FEATURE:
<223> OTHER INFORMATION: synthetic construct

<400> SEQUENCE: 31

```
Val Arg Gly Leu Tyr Phe Pro Ala Gly Gly Ser Ser Ser Gly Thr Val
1               5                   10                  15

Asn Pro Val Pro Thr Thr Ala Ser Pro Ile Ser Ser Ile Phe Ser Arg
            20                  25                  30
```

<210> SEQ ID NO 32
<211> LENGTH: 32
<212> TYPE: PRT
<213> ORGANISM: Artificial Sequence
<220> FEATURE:
<223> OTHER INFORMATION: synthetic construct

<400> SEQUENCE: 32

```
Val Arg Gly Leu Tyr Phe Pro Ala Gly Gly Ser Ser Ser Gly Thr Val
1               5                   10                  15

Asn Pro Ala Pro Asn Ile Ala Ser His Ile Ser Ser Ile Ser Ala Arg
            20                  25                  30
```

<210> SEQ ID NO 33
<211> LENGTH: 32
<212> TYPE: PRT
<213> ORGANISM: Artificial Sequence
<220> FEATURE:
<223> OTHER INFORMATION: synthetic construct

<400> SEQUENCE: 33

```
Val Arg Gly Leu Tyr Leu Pro Ala Gly Gly Ser Ser Ser Gly Thr Val
1               5                   10                  15

Asn Pro Val Pro Thr Thr Val Ser His Ile Ser Ser Ile Phe Ser Arg
            20                  25                  30
```

<210> SEQ ID NO 34
<211> LENGTH: 32
<212> TYPE: PRT
<213> ORGANISM: Artificial Sequence
<220> FEATURE:
<223> OTHER INFORMATION: synthetic construct

<400> SEQUENCE: 34

```
Val Arg Ala Leu Tyr Phe Pro Ala Gly Gly Ser Ser Ser Gly Thr Val
1               5                   10                  15

Ser Pro Ala Gln Asn Thr Val Ser Ala Ile Ser Ser Ile Leu Ser Lys
            20                  25                  30
```

<210> SEQ ID NO 35
<211> LENGTH: 34
<212> TYPE: PRT
<213> ORGANISM: Artificial Sequence
<220> FEATURE:
<223> OTHER INFORMATION: synthetic construct

<400> SEQUENCE: 35

```
Pro Asp His Gln Leu Asp Pro Ala Phe Gly Ala Asn Ser Asn Asn Pro
1               5                   10                  15

Asp Trp Asp Phe Asn Pro Asn Lys Asp His Trp Pro Glu Ala Asn Gln
            20                  25                  30

Val Gly
```

<210> SEQ ID NO 36
<211> LENGTH: 34
<212> TYPE: PRT
<213> ORGANISM: Artificial Sequence
<220> FEATURE:

<223> OTHER INFORMATION: synthetic construct

<400> SEQUENCE: 36

Pro Asp His Gln Leu Asp Pro Ala Phe Gly Ala Asn Ser Asn Asn Pro
1               5                   10                  15
Asp Trp Asp Phe Asn Pro Ile Lys Asp His Trp Pro Ala Ala Asn Gln
            20                  25                  30
Val Gly

<210> SEQ ID NO 37
<211> LENGTH: 34
<212> TYPE: PRT
<213> ORGANISM: Artificial Sequence
<220> FEATURE:
<223> OTHER INFORMATION: synthetic construct

<400> SEQUENCE: 37

Pro Asp His Gln Leu Asp Pro Ala Phe Arg Ala Asn Thr Ala Asn Pro
1               5                   10                  15
Asp Trp Asp Phe Asn Pro Asn Lys Asp Thr Trp Pro Asp Ala Asn Lys
            20                  25                  30
Val Gly

<210> SEQ ID NO 38
<211> LENGTH: 34
<212> TYPE: PRT
<213> ORGANISM: Artificial Sequence
<220> FEATURE:
<223> OTHER INFORMATION: synthetic construct

<400> SEQUENCE: 38

Pro Asp His Gln Leu Asp Pro Ala Phe Lys Ala Asn Ser Glu Asn Pro
1               5                   10                  15
Asp Trp Asp Leu Asn Pro His Lys Asp Asn Trp Pro Asp Ala His Lys
            20                  25                  30
Val Gly

<210> SEQ ID NO 39
<211> LENGTH: 25
<212> TYPE: DNA
<213> ORGANISM: Artificial Sequence
<220> FEATURE:
<223> OTHER INFORMATION: synthetic construct

<400> SEQUENCE: 39
tgaacagcat acactaacga gtttt                                         25

<210> SEQ ID NO 40
<211> LENGTH: 25
<212> TYPE: DNA
<213> ORGANISM: Artificial Sequence
<220> FEATURE:
<223> OTHER INFORMATION: synthetic construct

<400> SEQUENCE: 40
gcgtgtccac atactgcacc gtttt                                         25

<210> SEQ ID NO 41
<211> LENGTH: 30
<212> TYPE: PRT
<213> ORGANISM: Hepatitis B virus

<400> SEQUENCE: 41

```
Gly Leu Tyr Phe Pro Ala Gly Ser Ser Gly Thr Val Asn Pro
1               5                   10                  15

Val Pro Thr Thr Ala Ser Pro Ile Ser Ser Ile Phe Ser Arg
                20                  25                  30

<210> SEQ ID NO 42
<211> LENGTH: 400
<212> TYPE: PRT
<213> ORGANISM: Hepatitis B virus
<220> FEATURE:
<221> NAME/KEY: misc_feature
<222> LOCATION: (257)..(257)
<223> OTHER INFORMATION: Xaa can be any naturally occurring amino acid

<400> SEQUENCE: 42

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala His Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Leu Pro Ala Gly
130                 135                 140

Gly Ser Ser Ser Gly Thr Val Ser Pro Ala Gln Asn Thr Val Ser Ala
145                 150                 155                 160

Ile Ser Ser Ile Leu Ser Thr Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
        195                 200                 205

Trp Trp Thr Ser Leu Ser Phe Leu Gly Gly Thr Pro Val Cys Leu Gly
210                 215                 220

Gln Asn Ser Gln Ser Pro Ile Ser Ser His Ser Pro Thr Cys Cys Pro
225                 230                 235                 240

Pro Ile Cys Pro Gly Tyr Arg Trp Met Tyr Leu Arg Arg Phe Ile Ile
                245                 250                 255

Xaa Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320
```

```
Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Met Pro Leu Leu Pro Ile Phe Phe Cys Leu Trp Val Tyr Ile
385                 390                 395                 400

<210> SEQ ID NO 43
<211> LENGTH: 400
<212> TYPE: PRT
<213> ORGANISM: Hepatitis B virus

<400> SEQUENCE: 43

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp Gln Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
    290                 295                 300
```

Thr Ser Met Phe Pro Ser Cys Cys Thr Lys Pro Ser Asp Gly Asn
305                 310             315                 320

Cys Thr Cys Ile Pro Ile Pro Ser Ser Trp Ala Phe Ala Arg Phe Leu
                325             330                 335

Trp Glu Trp Ala Ser Val Arg Phe Ser Trp Leu Ser Leu Leu Val Pro
            340                 345             350

Phe Val Gln Trp Phe Val Gly Leu Ser Pro Thr Val Trp Leu Ser Val
        355                 360             365

Ile Trp Met Met Trp Tyr Trp Gly Pro Ser Leu Tyr Asn Ile Leu Ser
    370             375             380

Pro Phe Leu Pro Leu Leu Pro Ile Phe Phe Cys Leu Trp Val Tyr Ile
385             390             395                 400

<210> SEQ ID NO 44
<211> LENGTH: 281
<212> TYPE: PRT
<213> ORGANISM: Hepatitis B virus

<400> SEQUENCE: 44

Met Gln Trp Asn Ser Thr Thr Phe His Gln Ala Leu Leu Asp Pro Arg
1               5                   10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ser Ile Phe Ser Arg
        35                  40                  45

Thr Gly Asp Pro Ala Pro Asn Met Glu Ser Thr Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ala Pro Thr Cys Pro Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Leu Pro Gly Thr Ser Thr Thr Ser Thr Gly Pro Cys
                165                 170                 175

Arg Thr Cys Thr Ile Pro Ala Gln Gly Thr Ser Met Phe Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Arg Phe Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Ala Ile Trp Met Met Trp Tyr Trp
                245                 250                 255

Gly Pro Ser Leu Tyr Asn Ile Leu Ser Pro Phe Leu Pro Leu Leu Pro
            260                 265                 270

Ile Phe Phe Cys Leu Trp Val Tyr Ile 275             280

<210> SEQ ID NO 45
<211> LENGTH: 400
<212> TYPE: PRT
<213> ORGANISM: Hepatitis B virus

<400> SEQUENCE: 45

Met Gly Gly Tyr Ser Ser Lys Pro Arg Lys Gly Met Gly Thr Asn Leu
1               5                   10                  15

Ser Val Pro Asn Pro Leu Gly Phe Leu Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp Pro Trp Pro Glu Ala Trp Gln Val Gly Ala Gly Ala Phe Gly
50                  55                  60

Pro Gly Phe Thr Pro Pro His Gly Ser Leu Leu Gly Trp Ser Pro Gln
65                  70                  75                  80

Ala Gln Gly Ile Leu Thr Thr Val Pro Ala Thr Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
            115                 120                 125

Gln Ala Leu Leu Asp Pro Arg Val Arg Gly Leu Tyr Phe Pro Ala Gly
        130                 135                 140

Gly Ser Ser Ser Gly Thr Ala Asn Pro Val Pro Thr Thr Ala Ser Pro
145                 150                 155                 160

Ile Ser Ser Ile Phe Ser Arg Thr Gly Asp Pro Val Pro Lys Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Ala Cys Pro Gly
210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Thr Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Lys Phe Leu
                325                 330                 335

Trp Glu Trp Ala Ser Val Arg Phe Ser Trp Leu Ser Leu Leu Ala Pro
            340                 345                 350

Phe Val Gln Trp Phe Val Gly Leu Ser Pro Thr Val Trp Leu Ser Val
        355                 360                 365

```
Ile Trp Met Met Trp Tyr Trp Gly Pro Ser Leu Tyr Asn Ile Leu Ser
    370                 375                 380

Pro Phe Leu Pro Leu Leu Pro Ile Phe Phe Cys Leu Trp Val Tyr Ile
385                 390                 395                 400

<210> SEQ ID NO 46
<211> LENGTH: 400
<212> TYPE: PRT
<213> ORGANISM: Hepatitis B virus

<400> SEQUENCE: 46

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His His Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Lys Ala Asn Gln Val Arg Ala Gly Ala Phe Gly
    50                  55                  60

Pro Gly Phe Thr Pro Pro His Cys Ser Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Ser Asn Arg Gln Ser Gly Lys Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Thr Leu Gln Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Ile Gly Asp Pro Ala Leu Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Thr Thr Val Cys Leu Gly
    210                 215                 220

Gln Asn Ser Gln Ser Pro Ile Ser Asn His Ser Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Arg Thr Cys Thr Thr Pro Ala Gln Gly
    290                 295                 300

Thr Ser Met Tyr Pro Ser Cys Cys Cys Thr Lys Pro Ser Asp Gly Asn
305                 310                 315                 320

Cys Thr Cys Ile Pro Ile Pro Ser Ser Trp Ala Phe Gly Lys Phe Leu
                325                 330                 335

Trp Glu Trp Ala Ser Ala Arg Phe Ser Trp Leu Ser Leu Leu Val Pro
            340                 345                 350
```

```
Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Ser Ile Leu Ser
    370                 375                 380

Pro Phe Leu Pro Leu Leu Pro Ile Phe Phe Cys Leu Trp Val Tyr Ile
385                 390                 395                 400
```

<210> SEQ ID NO 47
<211> LENGTH: 138
<212> TYPE: PRT
<213> ORGANISM: Mus musculus

<400> SEQUENCE: 47

```
Met Tyr Leu Gly Leu Asn Cys Val Phe Ile Val Phe Leu Leu Lys Gly
1               5                   10                  15

Val Gln Ser Glu Val Asn Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Lys Ser Asp Asn Tyr Ala Thr His
65                  70                  75                  80

Phe Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Pro Glu Asp Thr
            100                 105                 110

Gly Ile Tyr Tyr Cys Thr Ser Pro Thr Ala Gly Thr Pro Phe Ala Tyr
        115                 120                 125

Trp Gly Gln Gly Thr Leu Val Thr Val Ser
    130                 135
```

<210> SEQ ID NO 48
<211> LENGTH: 138
<212> TYPE: PRT
<213> ORGANISM: Mus musculus

<400> SEQUENCE: 48

```
Met Tyr Leu Gly Leu Asn Cys Val Phe Ile Val Phe Leu Leu Lys Gly
1               5                   10                  15

Val Gln Ser Glu Val Lys Val Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Lys Ser Asn Asn Tyr Ala Thr His
65                  70                  75                  80

Tyr Ala Glu Tyr Ala Lys Gly Arg Phe Thr Ile Ser Arg Asp Asp Ser
                85                  90                  95

Lys Ser Thr Val Tyr Leu Gln Met Asn Asn Leu Arg Ala Glu Asp Thr
            100                 105                 110

Gly Ile Tyr Tyr Cys Thr Ser Pro Thr Ser Gly Thr Pro Phe Ala Tyr
        115                 120                 125

Trp Gly Gln Gly Thr Leu Val Thr Val Ser
    130                 135
```

<210> SEQ ID NO 49
<211> LENGTH: 138
<212> TYPE: PRT
<213> ORGANISM: Mus musculus

<400> SEQUENCE: 49

Met Tyr Leu Gly Leu Asn Cys Val Phe Ile Val Phe Leu Leu Lys Gly
1               5                   10                  15

Val Gln Ser Glu Val Lys Val Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Lys Ser Asn Asn Tyr Ala Thr His
65                  70                  75                  80

Tyr Ala Glu Ser Ala Lys Gly Arg Phe Thr Ile Ser Arg Asp Asp Ser
                85                  90                  95

Lys Ser Thr Val Tyr Leu Gln Met Asn Asn Leu Arg Ala Glu Asp Thr
            100                 105                 110

Gly Ile Tyr Tyr Cys Thr Ser Pro Thr Ser Gly Thr Pro Phe Ala Tyr
        115                 120                 125

Trp Gly Gln Gly Thr Leu Val Thr Val Ser
        130                 135

<210> SEQ ID NO 50
<211> LENGTH: 138
<212> TYPE: PRT
<213> ORGANISM: Mus musculus

<400> SEQUENCE: 50

Met Tyr Leu Gly Leu Asn Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Thr Met Lys Leu Ser Cys Val Ala Ser Gly Phe Thr Phe
        35                  40                  45

Ser Asn Tyr Trp Met Asn Trp Val Arg Gln Ser Pro Asp Lys Gly Leu
    50                  55                  60

Glu Trp Val Ala Glu Ile Arg Leu Arg Ser Asp Asn Phe Ala Thr His
65                  70                  75                  80

Phe Ala Glu Ser Val Lys Gly Arg Phe Thr Ile Ser Arg Asp Asp Ser
                85                  90                  95

Lys Ser Ser Val Tyr Leu Gln Met Asn Ser Leu Arg Ser Glu Asp Thr
            100                 105                 110

Gly Ile Tyr Tyr Cys Thr Ser Pro Thr Ala Gly Thr Pro Phe Ala Tyr
        115                 120                 125

Trp Gly Gln Gly Thr Leu Val Thr Val Ser
        130                 135

<210> SEQ ID NO 51
<211> LENGTH: 138
<212> TYPE: PRT
<213> ORGANISM: Mus musculus

<400> SEQUENCE: 51

Met Tyr Leu Gly Leu Asn Cys Val Phe Ile Val Phe Leu Leu Lys Gly
1               5                   10                  15

Val Gln Ser Glu Val Arg Leu Glu Glu Ser Gly Gly Gly Leu Val Gln
            20                  25                  30

Pro Gly Gly Ser Met Lys Leu Ser Cys Val Ala Ser Gly Phe Thr Phe
            35                  40                  45

Ser Asn Tyr Trp Met Asn Trp Val Arg Gln Ser Pro Glu Lys Gly Leu
    50                  55                  60

Glu Trp Val Ala Glu Ile Arg Leu Thr Ser Asp Asn Phe Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Val Glu Asp Thr
            100                 105                 110

Gly Ile Tyr Tyr Cys Thr Ser Pro Thr Ala Gly Thr Pro Phe Ala Tyr
        115                 120                 125

Trp Gly Gln Gly Thr Leu Val Thr Val Ser
    130                 135

<210> SEQ ID NO 52
<211> LENGTH: 138
<212> TYPE: PRT
<213> ORGANISM: Mus musculus

<400> SEQUENCE: 52

Met Tyr Leu Gly Leu Asn Cys Val Phe Ile Val Phe Leu Leu Lys Gly
1               5                   10                  15

Val Gln Gly Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
            35                  40                  45

Thr Asn Tyr Trp Met Asn Trp Val Arg Gln Ser Pro Glu Lys Gly Leu
    50                  55                  60

Glu Trp Val Ala Glu Ile Arg Val Lys Ser His Asn Tyr Ala Thr His
65                  70                  75                  80

Tyr Ala Glu Ser Val Thr Gly Arg Phe Thr Ile Ser Arg Asp Asp Ser
                85                  90                  95

Arg Ser Ser Val Tyr Leu Gln Met Asn Asn Leu Arg Ala Glu Asp Thr
            100                 105                 110

Gly Ile Tyr Tyr Cys Thr Ser Pro Thr Ala Gly Thr Pro Phe Ala Tyr
        115                 120                 125

Trp Gly Gln Gly Thr Leu Val Thr Val Ser
    130                 135

<210> SEQ ID NO 53
<211> LENGTH: 133
<212> TYPE: PRT
<213> ORGANISM: Mus musculus

<400> SEQUENCE: 53

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Lys Ala Glu Asp Leu Ala Val Tyr
             100                 105                 110

Tyr Cys Gln Gln Tyr Tyr Ser Tyr Pro Phe Thr Phe Gly Ser Gly Thr
             115                 120                 125

Lys Leu Glu Ile Lys
    130

<210> SEQ ID NO 54
<211> LENGTH: 133
<212> TYPE: PRT
<213> ORGANISM: Mus musculus

<400> SEQUENCE: 54

Met Asp Ser Gln Ala Gln Val Leu Met Leu Leu Leu Leu Trp Val Ser
 1               5                  10                  15

Gly Thr Cys Gly Asp Ile Val Met Ser Gln Ser Pro Ser Ser Leu Ala
             20                  25                  30

Val Ser Val Gly Glu Lys Val Thr Met Ser Cys Lys Ser Ser Gln Ser
         35                  40                  45

Val Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Lys Ala Glu Asp Leu Ala Val Tyr
             100                 105                 110

Tyr Cys Gln Gln Tyr Tyr Ser Tyr Pro Leu Thr Phe Gly Ala Gly Thr
             115                 120                 125

Lys Leu Glu Ile Lys
    130

<210> SEQ ID NO 55
<211> LENGTH: 133
<212> TYPE: PRT
<213> ORGANISM: Mus musculus

<400> SEQUENCE: 55

Met Asp Ser Gln Ala Gln Val Leu Met Leu Leu Leu Leu Trp Val Ser
 1               5                  10                  15

Gly Thr Cys Gly Asp Ile Val Met Ser Gln Ser Pro Ser Pro Gln Thr
             20                  25                  30

Val Ser Val Gly Glu Lys Val Thr Met Ser Cys Lys Ser Ser Gln Ser
         35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

```
Phe Thr Leu Thr Ile Ser Ser Val Lys Ala Glu Asp Leu Ala Val Tyr
                100                 105                 110

Tyr Cys Gln Gln Tyr Tyr Thr Tyr Pro Trp Thr Phe Gly Gly Gly Thr
            115                 120                 125

Lys Leu Glu Ile Lys
        130

<210> SEQ ID NO 56
<211> LENGTH: 133
<212> TYPE: PRT
<213> ORGANISM: Mus musculus

<400> SEQUENCE: 56

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Trp Thr Phe Gly Gly Gly Thr
            115                 120                 125

Lys Leu Glu Ile Lys
        130

<210> SEQ ID NO 57
<211> LENGTH: 133
<212> TYPE: PRT
<213> ORGANISM: Mus musculus

<400> SEQUENCE: 57

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
            35                  40                  45

Leu Leu Tyr Ser Asn Asn Gln Lys Asn Tyr Leu Ala Trp Tyr Arg Gln
    50                  55                  60

Lys Pro Gly Gln Ser Pro Lys Leu Leu Ile Tyr Trp Ala Ser Ile Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Arg Ala Glu Asp Leu Ala Val Phe
                100                 105                 110

Phe Cys Gln Gln Tyr Tyr Lys Tyr Pro Trp Thr Phe Gly Gly Gly Thr
            115                 120                 125

Lys Leu Glu Ile Lys
        130
```

<210> SEQ ID NO 58
<211> LENGTH: 133
<212> TYPE: PRT
<213> ORGANISM: Mus musculus

<400> SEQUENCE: 58

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Trp Thr Phe Gly Gly Gly Thr
        115                 120                 125

Lys Leu Asp Ile Lys
        130

<210> SEQ ID NO 59
<211> LENGTH: 117
<212> TYPE: PRT
<213> ORGANISM: Mus musculus

<400> SEQUENCE: 59

Met Gly Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Ile Ser Cys Lys Ala Ser Gly Tyr Thr Phe
            35                  40                  45

Thr Ser Tyr Trp Met Asp Trp Val Lys Gln Arg Pro Gly Gln Gly Leu
    50                  55                  60

Glu Trp Ile Gly Trp Ile Tyr Pro Gly Asp Gly Asp Thr Asn Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Arg Ala Arg
        115

<210> SEQ ID NO 60
<211> LENGTH: 117
<212> TYPE: PRT
<213> ORGANISM: Mus musculus

<400> SEQUENCE: 60

Met Gly Trp Arg Trp Ile Leu Leu Phe Leu Leu Ser Gly Thr Ala Gly
1               5                   10                  15

Val His Ser Gln Val Gln Leu Gln Gln Ser Gly Pro Glu Leu Val Lys

```
                20                  25                  30
Pro Gly Ala Ser Val Lys Met Ser Cys Lys Ala Ser Gly Tyr Thr Phe
            35                  40                  45

Thr Thr Tyr Asp Ile Asn Trp Val Lys Gln Arg Pro Gly Gln Gly Leu
    50                  55                  60

Glu Trp Ile Gly Trp Ile Tyr Pro Gly Asp Gly Ser Thr Lys Leu Asn
65                  70                  75                  80

Glu Ser Phe Lys Gly Lys Ala Ser Leu Thr Ala Asp Lys Ser Ser Ser
                85                  90                  95

Thr Ala Tyr Leu His Leu Ser Ser Leu Pro Ser Glu Asn Ser Ala Val
            100                 105                 110

Tyr Phe Cys Ala Arg
        115

<210> SEQ ID NO 61
<211> LENGTH: 19
<212> TYPE: PRT
<213> ORGANISM: Hepatitis B virus

<400> SEQUENCE: 61

Gly Thr Val Asn Pro Val Pro Thr Thr Ala Ser Pro Ile Ser Ser Ile
1               5                   10                  15

Phe Ser Arg

<210> SEQ ID NO 62
<211> LENGTH: 19
<212> TYPE: PRT
<213> ORGANISM: Hepatitis B virus

<400> SEQUENCE: 62

Gly Thr Val Asn Pro Val Pro Ala Thr Ala Ser Pro Ile Ser Ser Ile
1               5                   10                  15

Phe Ser Arg

<210> SEQ ID NO 63
<211> LENGTH: 19
<212> TYPE: PRT
<213> ORGANISM: Hepatitis B virus

<400> SEQUENCE: 63

Gly Thr Val Asn Pro Ala Pro Asn Ile Ala Ser His Ile Ser Ser Ile
1               5                   10                  15

Ser Ala Arg

<210> SEQ ID NO 64
<211> LENGTH: 489
<212> TYPE: PRT
<213> ORGANISM: Artificial Sequence
<220> FEATURE:
<223> OTHER INFORMATION: synthetic construct

<400> SEQUENCE: 64

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
```

```
            50                  55                  60
Phe Ile Asn Thr Thr Ile Ala Ser Ile Ala Ala Lys Glu Glu Gly Val
 65                  70                  75                  80

Ser Leu Asp Lys Arg Glu Ala Glu Ala Met Gly Gly Trp Ser Ser Lys
                 85                  90                  95

Pro Arg Gln Gly Met Gly Thr Asn Leu Ser Val Pro Asn Pro Leu Gly
                100                 105                 110

Phe Phe Pro Asp His Gln Leu Asp Pro Ala Phe Gly Ala Asn Ser Asn
                115                 120                 125

Asn Pro Asp Trp Asp Phe Asn Pro Asn Lys Asp His Trp Pro Glu Ala
                130                 135                 140

Asn Gln Val Gly Ala Gly Ala Phe Gly Pro Gly Phe Thr Pro Pro His
145                 150                 155                 160

Gly Gly Leu Leu Gly Trp Ser Pro Gln Ala Gln Gly Val Leu Thr Thr
                165                 170                 175

Val Pro Val Ala Pro Pro Ala Ser Thr Asn Arg Gln Ser Gly Arg
                180                 185                 190

Gln Pro Thr Pro Ile Ser Pro Leu Arg Asp Ser His Pro Gln Ala
                195                 200                 205

Met Gln Trp Asn Ser Thr Thr Phe His Gln Ala Leu Leu Asp Pro Arg
    210                 215                 220

Val Arg Gly Leu Tyr Leu Pro Ala Gly Gly Ser Ser Ser Gly Thr Val
225                 230                 235                 240

Asn Pro Val Pro Thr Thr Ala Ser Pro Ile Ser Ser Ile Phe Ser Arg
                245                 250                 255

Thr Gly Asp Pro Ala Pro Asn Met Glu Asn Thr Thr Ser Gly Phe Leu
                260                 265                 270

Gly Pro Leu Leu Val Leu Gln Ala Gly Phe Phe Leu Leu Thr Arg Ile
                275                 280                 285

Leu Thr Ile Pro Gln Ser Leu Asp Ser Trp Trp Thr Ser Leu Asn Phe
                290                 295                 300

Leu Gly Gly Ala Pro Thr Cys Pro Gly Gln Asn Ser Gln Ser Pro Thr
305                 310                 315                 320

Ser Asn His Ser Pro Thr Ser Cys Pro Pro Ile Cys Pro Gly Tyr Arg
                325                 330                 335

Trp Met Cys Leu Arg Arg Phe Ile Ile Phe Leu Phe Ile Leu Leu Leu
                340                 345                 350

Cys Leu Ile Phe Leu Leu Val Leu Leu Asp Tyr Gln Gly Met Leu Pro
                355                 360                 365

Val Cys Pro Leu Leu Pro Gly Thr Ser Thr Thr Ser Thr Gly Pro Cys
    370                 375                 380

Lys Thr Cys Thr Ile Pro Ala Gln Gly Thr Ser Met Phe Pro Ser Cys
385                 390                 395                 400

Cys Cys Thr Lys Pro Ser Asp Gly Asn Cys Thr Cys Ile Pro Ile Pro
                405                 410                 415

Ser Ser Trp Ala Phe Ala Arg Phe Leu Trp Glu Trp Ala Ser Val Arg
                420                 425                 430

Phe Ser Trp Leu Ser Leu Leu Val Pro Phe Val Gln Trp Phe Val Gly
                435                 440                 445

Leu Ser Pro Thr Val Trp Leu Ser Val Ile Trp Met Met Trp Tyr Trp
                450                 455                 460
```

```
-continued

Gly Pro Ser Leu Tyr Asn Ile Leu Ser Pro Phe Leu Pro Leu Leu Pro
465                 470                 475                 480

Ile Phe Phe Cys Leu Trp Val Tyr Ile
                485
```